US010851125B2

(12) United States Patent
Lapina et al.

(10) Patent No.: US 10,851,125 B2
(45) Date of Patent: Dec. 1, 2020

(54) CRYSTALLINE FORMS OF ETHYL ((S)-((((2R,5R)-5-(6-AMINO-9H-PURIN-9-YL)-4-FLUORO-2,5-DIHYDROFURAN-2-YL)OXY)METHYL)(PHENOXY) PHOSPHORYL(-L-ALANINATE

(71) Applicant: Gilead Sciences, Inc., Foster City, CA (US)

(72) Inventors: Olga Viktorovna Lapina, Newark, CA (US); Bing Shi, Redwood City, CA (US); Silas Wang, Foster City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 16/049,441

(22) Filed: Jul. 30, 2018

(65) Prior Publication Data

US 2019/0040092 A1 Feb. 7, 2019

Related U.S. Application Data

(60) Provisional application No. 62/539,822, filed on Aug. 1, 2017.

(51) Int. Cl.
| | | |
|---|---|---|
| *C07F 9/6561* | (2006.01) |
| *A61P 31/18* | (2006.01) |
| *A61K 31/675* | (2006.01) |
| *A61K 31/5365* | (2006.01) |
| *C07D 473/34* | (2006.01) |
| *C07H 19/20* | (2006.01) |
| *C07H 19/16* | (2006.01) |
| *A61K 31/5377* | (2006.01) |
| *A61K 31/635* | (2006.01) |
| *A61K 45/06* | (2006.01) |
| *C07D 417/12* | (2006.01) |
| *C07D 493/04* | (2006.01) |
| *C07D 498/14* | (2006.01) |

(52) U.S. Cl.
CPC ...... *C07F 9/65616* (2013.01); *A61K 31/5365* (2013.01); *A61K 31/5377* (2013.01); *A61K 31/635* (2013.01); *A61K 31/675* (2013.01); *A61K 45/06* (2013.01); *A61P 31/18* (2018.01); *C07D 417/12* (2013.01); *C07D 473/34* (2013.01); *C07D 493/04* (2013.01); *C07D 498/14* (2013.01); *C07H 19/16* (2013.01); *C07H 19/20* (2013.01); *C07B 2200/13* (2013.01)

(58) Field of Classification Search
CPC .................................................. C07F 9/65616
See application file for complete search history.

(56) References Cited

U.S. PATENT DOCUMENTS

| | | |
|---|---|---|
| 4,120,689 A | 10/1978 | Gerard |
| 4,198,355 A | 4/1980 | Schmitt |
| 4,649,041 A | 3/1987 | Peters et al. |
| 4,665,074 A | 5/1987 | Amschler |
| 4,816,570 A | 3/1989 | Farquhar |
| 4,918,179 A | 4/1990 | Watanabe |
| 4,968,788 A | 11/1990 | Farquhar |
| 5,260,440 A | 11/1993 | Hirai et al. |
| 5,378,474 A | 1/1995 | Morella et al. |
| 5,413,996 A | 5/1995 | Bodor |
| 5,455,339 A | 10/1995 | Chu |
| 5,459,256 A | 10/1995 | Marquez et al. |
| 5,466,793 A | 11/1995 | Honda et al. |
| 5,493,030 A | 2/1996 | Morgans et al. |
| 5,585,397 A | 12/1996 | Tung et al. |
| 5,633,279 A | 5/1997 | Morgans et al. |
| 5,654,286 A | 8/1997 | Hostetler |
| 5,656,745 A | 8/1997 | Bischofberger et al. |
| 5,663,159 A | 9/1997 | Starrett, Jr. et al. |
| 5,670,497 A | 9/1997 | Bold et al. |
| 5,744,600 A | 4/1998 | Mansuri et al. |
| 5,747,498 A | 5/1998 | Schnur et al. |
| 5,750,343 A | 5/1998 | Maag et al. |
| 5,750,493 A | 5/1998 | Sommadossi et al. |
| 5,792,756 A | 8/1998 | Starrett, Jr. et al. |
| 5,795,909 A | 8/1998 | Shashoua et al. |
| 5,804,559 A | 9/1998 | Budt et al. |
| 5,811,422 A | 9/1998 | Lam et al. |
| 5,874,577 A | 2/1999 | Chen et al. |
| 5,914,332 A | 6/1999 | Chen et al. |
| 5,962,684 A | 10/1999 | Vince et al. |
| 6,018,049 A | 1/2000 | Hajima et al. |
| 6,072,053 A | 6/2000 | Vince et al. |
| 6,174,888 B1 | 1/2001 | McQuire et al. |
| 6,290,994 B1 | 9/2001 | Lazaro Flores et al. |
| 6,312,662 B1 | 11/2001 | Erion et al. |
| 6,319,946 B1 | 11/2001 | Hale et al. |

(Continued)

FOREIGN PATENT DOCUMENTS

| | | |
|---|---|---|
| AU | 779816 | 10/2000 |
| CN | 101031306 | 9/2007 |

(Continued)

OTHER PUBLICATIONS

Healthline. Viral Disease 101 (2018) Web< https://www.healthline.corn/health/viral-diseases>.*

(Continued)

*Primary Examiner* — Emily A Bernhardt
*Assistant Examiner* — Laura M Daniel
(74) *Attorney, Agent, or Firm* — Fish & Richardson P.C.

(57) ABSTRACT

The present invention relates to novel forms of ethyl ((S)-((((2R,5R)-5-(6-amino-9H-purin-9-yl)-4-fluoro-2,5-dihydrofuran-2-yl)oxy)methyl)(phenoxy)phosphoryl)-L-alaninate, pharmaceutical formulations, and therapeutic uses thereof in treating viral infections (e.g., an HIV infection).

14 Claims, 25 Drawing Sheets

(56) References Cited

U.S. PATENT DOCUMENTS

| | | |
|---|---|---|
| 6,395,763 B1 | 5/2002 | Stamos et al. |
| 6,555,676 B2 | 4/2003 | Gosselin et al. |
| 6,581,606 B2 | 6/2003 | Kutzko et al. |
| 6,602,902 B2 | 8/2003 | Shashoua et al. |
| 6,608,027 B1 | 8/2003 | Tsantrizos et al. |
| 6,761,903 B2 | 7/2004 | Chen et al. |
| 6,767,900 B2 | 7/2004 | Ubasawa et al. |
| 6,844,349 B2 | 1/2005 | Kath et al. |
| 6,858,618 B2 | 2/2005 | Raza et al. |
| 6,872,827 B2 | 3/2005 | Webb et al. |
| 6,962,684 B2 | 11/2005 | Kawazu et al. |
| 7,084,123 B2 | 8/2006 | Fuiikura et al. |
| 7,169,766 B2 | 1/2007 | Sommadossi et al. |
| 7,273,715 B2 | 9/2007 | McDermott |
| 7,273,716 B2 | 9/2007 | McDermott |
| 7,276,717 B2 | 9/2007 | McDermott |
| 7,300,924 B2 | 11/2007 | Boojamra et al. |
| 7,319,148 B2 | 1/2008 | Marliere et al. |
| 7,358,261 B2 | 4/2008 | Carson et al. |
| 7,390,791 B2 | 6/2008 | Becker et al. |
| 7,407,965 B2 | 8/2008 | Chen et al. |
| 7,417,055 B2 | 8/2008 | Cannizzaro et al. |
| 7,427,624 B2 | 9/2008 | Chen et al. |
| 7,427,636 B2 | 9/2008 | Cannizzaro et al. |
| 7,429,564 B2 | 9/2008 | Arbit et al. |
| 7,429,565 B2 | 9/2008 | Boojamra et al. |
| 7,432,261 B2 | 10/2008 | Cannizzaro et al. |
| 7,432,273 B2 | 10/2008 | Fardis et al. |
| 7,452,901 B2 | 11/2008 | Boojamra et al. |
| 7,462,608 B2 | 12/2008 | Chen et al. |
| 7,470,724 B2 | 12/2008 | Cannizzaro et al. |
| 7,645,747 B2 | 1/2010 | Boojamra et al. |
| 7,649,015 B2 | 1/2010 | Arimili et al. |
| 7,871,991 B2 | 1/2011 | Boojamra et al. |
| 7,871,992 B2 | 1/2011 | Jomaa et al. |
| 8,022,083 B2 | 9/2011 | Boojamra et al. |
| 8,318,701 B2 | 11/2012 | Boojamra et al. |
| 8,329,926 B2 | 12/2012 | Mackman et al. |
| 8,563,530 B2 | 10/2013 | Chang et al. |
| 8,658,617 B2 | 2/2014 | Graetz et al. |
| 8,697,861 B2 | 4/2014 | Boojamra et al. |
| 8,871,785 B2 | 10/2014 | Boojamra et al. |
| 8,951,986 B2 | 2/2015 | Graetz et al. |
| 8,987,437 B2 | 3/2015 | Yu et al. |
| 9,139,604 B2 | 9/2015 | Boojamra et al. |
| 9,296,779 B2 | 3/2016 | Yu et al. |
| 9,381,206 B2 | 7/2016 | Graetz et al. |
| 9,457,035 B2 | 10/2016 | Boojamra et al. |
| 9,579,332 B2 | 2/2017 | Boojamra et al. |
| 9,783,567 B2 | 10/2017 | Yu et al. |
| 9,783,568 B2 | 10/2017 | Graetz et al. |
| 10,196,419 B2 | 2/2019 | Yu et al. |
| 2001/0031773 A1 | 10/2001 | Camden |
| 2002/0051805 A1 | 5/2002 | Ueki et al. |
| 2002/0103378 A1 | 8/2002 | Ellis |
| 2002/0119443 A1 | 8/2002 | Becker et al. |
| 2002/0156133 A1 | 10/2002 | Bartholomaeus et al. |
| 2003/0045583 A1 | 3/2003 | Hadfield et al. |
| 2003/0109498 A1 | 6/2003 | Yuasa et al. |
| 2003/0149044 A1 | 8/2003 | Quallich et al. |
| 2004/0121316 A1 | 6/2004 | Birkus et al. |
| 2004/0157793 A1 | 8/2004 | Stuyver et al. |
| 2004/0167096 A1 | 8/2004 | Cheng et al. |
| 2005/0009043 A1 | 1/2005 | Becker et al. |
| 2005/0037925 A1 | 2/2005 | Tsukamoto et al. |
| 2005/0171126 A1 | 8/2005 | Torii et al. |
| 2005/0202054 A1 | 9/2005 | Faryniarz et al. |
| 2005/0215513 A1 | 9/2005 | Boojamra et al. |
| 2006/0069060 A1 | 3/2006 | Redkar et al. |
| 2006/0079478 A1 | 4/2006 | Boojamra et al. |
| 2006/0094870 A1 | 5/2006 | Torii et al. |
| 2006/0223794 A1 | 10/2006 | Bourghol Hickey et al. |
| 2006/0223820 A1 | 10/2006 | Brand et al. |
| 2006/0281759 A1 | 12/2006 | De Diego et al. |
| 2007/0049754 A1 | 3/2007 | Boojamra et al. |
| 2007/0149479 A1 | 6/2007 | Fischer et al. |
| 2007/0149552 A1 | 6/2007 | Ku et al. |
| 2007/0191482 A1 | 8/2007 | Choi et al. |
| 2007/0225249 A1 | 9/2007 | Shi |
| 2008/0207620 A1 | 8/2008 | Desai et al. |
| 2008/0221213 A1 | 9/2008 | Christgau |
| 2008/0226731 A1 | 9/2008 | Vasanthavada et al. |
| 2008/0279932 A1 | 11/2008 | Reber et al. |
| 2009/0012037 A1 | 1/2009 | Boojamra et al. |
| 2009/0163449 A1 | 6/2009 | Wempe |
| 2009/0202470 A1 | 8/2009 | Boojamra et al. |
| 2009/0275535 A1 | 11/2009 | Boojamra et al. |
| 2010/0093667 A1 | 4/2010 | Graetz et al. |
| 2010/0104532 A1 | 4/2010 | Chen et al. |
| 2010/0143301 A1 | 6/2010 | Desai et al. |
| 2011/0144050 A1 | 6/2011 | Graetz et al. |
| 2011/0288053 A1 | 11/2011 | Boojamra et al. |
| 2012/0296076 A1 | 11/2012 | Yu et al. |
| 2013/0090299 A1 | 4/2013 | Boojamra et al. |
| 2013/0090302 A1 | 4/2013 | Boojamra et al. |
| 2013/0165489 A1 | 6/2013 | Cocklin et al. |
| 2013/0316969 A1 | 11/2013 | Boojamra et al. |
| 2014/0221356 A1 | 8/2014 | Jin et al. |
| 2014/0221378 A1 | 8/2014 | Miyazaki et al. |
| 2014/0221380 A1 | 8/2014 | Miyazaki et al. |
| 2014/0227224 A1 | 8/2014 | Graetz et al. |
| 2014/0288294 A1 | 9/2014 | Boojamra et al. |
| 2015/0182547 A1 | 7/2015 | Graetz et al. |
| 2016/0340379 A1 | 11/2016 | Yu et al. |
| 2016/0355543 A1 | 12/2016 | Graetz et al. |
| 2017/0088576 A1 | 3/2017 | Boojamra et al. |
| 2017/0210770 A1 | 7/2017 | Boojamra et al. |
| 2018/0079773 A1 | 3/2018 | Yu et al. |
| 2018/0085387 A1 | 3/2018 | Bischofberger et al. |
| 2018/0086784 A1 | 3/2018 | Boojamra et al. |
| 2019/0315785 A1 | 10/2019 | Boojamra et al. |
| 2019/0345190 A1 | 11/2019 | Boojamra et al. |
| 2019/0359644 A1 | 11/2019 | Yu et al. |

FOREIGN PATENT DOCUMENTS

| | | |
|---|---|---|
| DE | 4138584 | 5/1993 |
| EA | 014685 | 12/2010 |
| EP | 0347852 | 12/1989 |
| EP | 0369409 | 5/1990 |
| EP | 0441192 | 1/1991 |
| EP | 0428109 | 5/1991 |
| EP | 0465297 | 1/1992 |
| EP | 0468119 | 1/1992 |
| EP | 0468866 | 1/1992 |
| EP | 0531597 | 3/1993 |
| EP | 0632048 | 1/1995 |
| EP | 0786455 | 6/1997 |
| EP | 0267050 | 5/1998 |
| EP | 0852233 | 7/1998 |
| EP | 0919562 | 6/1999 |
| EP | 1295879 | 3/2003 |
| EP | 1778249 | 5/2007 |
| EP | 1832582 | 9/2007 |
| EP | 2305680 | 4/2011 |
| GB | 835785 | 5/1960 |
| JP | 02-178295 | 7/1990 |
| JP | 2003005439 | 1/1991 |
| JP | H04330086 | 11/1992 |
| JP | 2007-238624 | 9/1994 |
| JP | 2007-502329 | 2/2007 |
| JP | 06-507883 | 9/2007 |
| RU | 2106353 | 3/1998 |
| RU | 2188203 | 8/2002 |
| WO | WO 1988/06158 | 8/1988 |
| WO | WO 1991/19721 | 12/1991 |
| WO | WO 1992/00988 | 1/1992 |
| WO | WO 1992/03452 | 3/1992 |
| WO | WO 1992/13869 | 8/1992 |
| WO | WO 1992/18520 | 10/1992 |
| WO | WO 1993/12123 | 6/1993 |
| WO | WO 1993/24510 | 12/1993 |
| WO | WO 1994/21604 | 9/1994 |
| WO | WO 1995/07920 | 3/1995 |

(56) References Cited

FOREIGN PATENT DOCUMENTS

| | | |
|---|---|---|
| WO | WO 1996/14314 | 5/1996 |
| WO | WO 1996/15111 | 5/1996 |
| WO | WO 1996/20156 | 12/1996 |
| WO | WO 1997/01558 | 1/1997 |
| WO | WO 1998/04569 | 2/1998 |
| WO | WO 1998/11906 | 3/1998 |
| WO | WO 1998/15563 | 4/1998 |
| WO | WO 1999/33815 | 4/1998 |
| WO | WO 1999/029702 | 6/1999 |
| WO | WO 1999/22815 | 7/1999 |
| WO | WO 1999/43691 | 9/1999 |
| WO | WO 1999/62921 | 12/1999 |
| WO | WO 2000/04033 | 1/2000 |
| WO | WO 2000/52015 | 9/2000 |
| WO | WO 2000/56734 | 9/2000 |
| WO | WO 2001/13957 | 3/2001 |
| WO | WO 2001/17982 | 3/2001 |
| WO | WO 2001/19320 | 3/2001 |
| WO | WO 2001/039724 | 6/2001 |
| WO | WO 2001/39724 | 6/2001 |
| WO | WO 2001/46204 | 6/2001 |
| WO | WO 2001/64693 | 9/2001 |
| WO | WO 2001/96329 | 12/2001 |
| WO | WO 2001/96354 | 12/2001 |
| WO | WO 2001/096354 | 12/2001 |
| WO | WO 2002/03997 | 1/2002 |
| WO | WO 2002/06292 | 1/2002 |
| WO | WO 2002/08241 | 1/2002 |
| WO | WO 2002/14344 | 2/2002 |
| WO | WO 2002/048165 | 6/2002 |
| WO | WO 2002/057425 | 7/2002 |
| WO | WO 2002/019443 | 8/2002 |
| WO | WO 2002/100415 | 12/2002 |
| WO | WO 2002/103008 | 12/2002 |
| WO | WO 2003/028737 | 4/2003 |
| WO | WO 2003/050129 | 6/2003 |
| WO | WO 2003/059255 | 7/2003 |
| WO | WO 2003/064383 | 8/2003 |
| WO | WO 2003/066005 | 8/2003 |
| WO | WO 2003/080078 | 10/2003 |
| WO | WO 2003/090690 | 11/2003 |
| WO | WO 2003/090691 | 11/2003 |
| WO | WO 2003/091264 | 11/2003 |
| WO | WO 2004/096233 | 11/2004 |
| WO | WO 2004/096234 | 11/2004 |
| WO | WO 2004/096235 | 11/2004 |
| WO | WO 2004/096236 | 11/2004 |
| WO | WO 2004/096237 | 11/2004 |
| WO | WO 2004/096285 | 11/2004 |
| WO | WO 2004/096286 | 11/2004 |
| WO | WO 2004/096287 | 11/2004 |
| WO | WO 2004/96818 | 11/2004 |
| WO | WO 2004/100960 | 11/2004 |
| WO | WO 2005/000786 | 1/2005 |
| WO | WO 2005/002626 | 1/2005 |
| WO | WO 2005/011709 | 2/2005 |
| WO | WO 2005/012324 | 2/2005 |
| WO | WO 2005/039552 | 5/2005 |
| WO | WO 2005/042772 | 5/2005 |
| WO | WO 2005/042773 | 5/2005 |
| WO | WO 2005/044279 | 5/2005 |
| WO | WO 2005/044308 | 5/2005 |
| WO | WO 2005/047898 | 5/2005 |
| WO | WO 2005/063258 | 7/2005 |
| WO | WO 2005/063751 | 7/2005 |
| WO | WO 2005/064008 | 7/2005 |
| WO | WO 2006/015261 | 2/2006 |
| WO | WO 2006/015262 | 2/2006 |
| WO | WO 2006/020276 | 2/2006 |
| WO | WO 2006/051261 | 5/2006 |
| WO | WO 2006/110157 | 10/2006 |
| WO | WO 2007/014352 | 2/2007 |
| WO | WO 2007/109005 | 9/2007 |
| WO | WO 2008/010921 | 1/2008 |
| WO | WO 2008/100447 | 8/2008 |
| WO | WO 2009/062285 | 5/2009 |
| WO | WO 2010/005986 | 1/2010 |
| WO | WO 2010/130034 | 11/2010 |
| WO | WO 2011/003018 | 1/2011 |
| WO | WO 2012/003497 | 1/2012 |
| WO | WO 2012/003498 | 1/2012 |
| WO | WO 2012/145728 | 10/2012 |
| WO | WO 2012/159047 | 11/2012 |
| WO | WO 2013/006738 | 1/2013 |
| WO | WO 2013/006792 | 1/2013 |
| WO | WO 2013/091096 | 6/2013 |
| WO | WO 2013/159064 | 10/2013 |
| WO | WO 2014/055603 | 4/2014 |
| WO | WO 2014/055618 | 4/2014 |
| WO | WO 2014/100323 | 6/2014 |
| WO | WO 2015/040640 | 3/2015 |
| WO | WO 2018/144390 | 8/2018 |

OTHER PUBLICATIONS

Abdel-Meguid et al., "Inhibition of Human Immunodeficiency Virus-1 Protease by a C2-Symmetric Phosphinate: Synthesis and Crystallographic Analysis," Biochemistry, 32(31), 1993, 1543-1572.

Alexander et al. "Investigation of (Oxodioxolenyl)methyl Carbamates as Nonchiral Bioreversible Prodrug Moieties for Chiral Amines" J. Med. Chem, Jan. 1996, 39(2), 480-486.

Allen et al., CI-1040 (PDI84352), a Targeted Signal Transduction Inhibitor ofMEK (MAPKK), Seminars in Oncology, Oct. 2003, 30(5), Supp. 16, 105-116.

Anan'Eva et al. "(2-Iodoethyl) Phosphoric Derivatives" J. Gen. Chem USSR, 1983, 53(3): 480-483.

Anderson et al., "2-Chloro-4(R), 5(R)-dimethyl-2-oxo-1,3,2-dioxaphospholane, a New Chiral Derivatizing Agent," J. Org. Chem, 1984, 49,1304-1305.

Anonymous. (Oct. 31, 2006). CAS Registry No. 182550-46-5, Search Date: Apr. 20, 2011.

Asante-Appiah, E. et al. "HIV-1 Integrase: Structural Organization, Conformational Changes, and Catalysis" Advances in Virus Research 52:351-363 (1999).

Avert. (2010). "HIV and AIDS Vaccine," located at <http://www.avert.org/aids-vaccine.htm>, last visited on Sep. 16, 2013, 11 pages.

Avila et al., "Phosphonium Ion Fragmentations Relevant to Organophosphonate Biodegradation", J. Am. Chem. Soc., 111, 8969-8970 (1989).

Ballatore et al., "Synthesis and Evaluation of Novel Amidate Prodrugs of PMEA and PMPA", Bioorganic & Medicinal Chemistry Letters, 11, 1053-1056 (2001).

Balsiger, R.W. et al. "Synthesis of Potential Anticancer Agents. XVIII. Analogs of Carbamoyl Phosphate" J. Orn. Chem. 24, 434-436 (1959).

Balthazor, T.M. et al. "Nickel-Catalyzed Arbuzov Reaction: Mechanistic Observations" J. Oriz. Chem. 45, 5425-5426 (1980).

Bantia, Shanta et al., "Purine nucleoside phosphorylase inhibitor BCX-1777 (Immucillin-H)—a novel potent and orally active immunosuppressive agent", International Immunooharmacoloizv. vol. 1, 1199-1210, (2001).

Barre-Sinoussi, F. "HIV as the Cause of AIDS" Lancet 348, 31-35 (1996).

Beauchamp, Lilia M., et al., "Guanine, Pyrazolo[3,4-d]pyrimidine, and Triazolo [4,5-d]pyrimidine(8-Azaguanine) Phosphonate Acyclic Derivatives as Inhibitors of Purine Nucleoside Phosphorylase", Journal of Medicinal Chemistry, vol. 39, 949-956, (1996).

Benzaria, S. et al. "Synthesis, In Vitro Antiviral Evaluation, and Stability Studies of Bis(S-acyl-2-thioethyl) Ester Derivatives of 9-[2-(Phosphonomethoxy)ethyl]adenine (PMEA) as Potential PMEA Prodrugs with Improved Oral Bioavailability" J. Med. Chem. 39, 4958-4965 (1996).

Berge, S.M. et al. "Pharmaceutical Salts", Journal of Pharmaceutical Sciences. vol. 66, No. 1, 1-19 (1977).

Beusen, D.D. et al. "Solid-State Nuclear Magnetic Resonance Analysis of the Conformation of an Inhibitor Bound to Thermolysin" J. Med. Chem. 38(14), 2742-2747 (1995).

(56) References Cited

OTHER PUBLICATIONS

Birkus et al., "Cathepsin A is the Major Hydrolase Catalyzing the Intracellular Hydrolysis of the Antiretroviral Nucleotide Phosphonoamidate Prodrugs GS-7340 and GS-9131," Antimicrob. Agents Chemother., 51(2):543-550 (2007).
Boojamra et al., "Synthesis and anti-HIV activity of GS-9148 (2'-Fd4AP), a novel nucleoside phosphonate HIV reverse transcriptase inhibitor", Bioorganic & Medicinal Chemistry Letters, 18, 1120-1123 (2008).
Borhani et al., "A-420983: a potent, orally active inhibitor of Ick with efficacy in a model of transplant rejection", Bioorganic & Medicinal Chemistry Letters, vol. 14, 2613-2616, (2004).
Bowker, M.J. "A Procedure for Salt Selection and Optimization", Handbook of Pharmaceutical Salts: Prooerties Selection and Use. Chapter 7, 161-189 (2002).
Bundgaard, Design of Prodrugs, 70-74, (1985).
Bundgaard, H. et al. "Design and Application of Prodrugs", Textbook of Drug Design and Develonment, 113-191 (1991).
Burger, A. et al. "Monoesters and Ester-Amidates of Aromatic Phosphoric Acids", J. AM. Chem. Society 79, 3575-3579 (1957).
Bzowska, Agnieszka et al., "Purine nucleoside phosphorylases: properties, functions, and clinical aspects", Pharmacology & Therapeutics, 88:349-425, (2000).
Campagne, J. et al. "(1H-Benzotriazol-1-yloxy)tris(dimethylamino)phosphonium Hexafluorophosphate- and (1H-Benzotriazol-1-yloxy)tripyrrolidinophosphonium Hexafluorophosphate-Mediated Activation . . . " J. Org. Chem. 60(16), 5214-5223 (1995).
Campagne, J. et al. "Synthesis of Mixed Phosphonate Diester Analogues of Dipeptides Using BOP or PyBOP Reagents" Tetrahedron Letters 34(42), 6743-6744 (1993).
Campbell, D. "The Synthesis of Phosphonate Esters, an Extension of the MitsunobuReaction" J. Orn. Chem. 57, 6331-6335 (1992).
Carter, H.E. et al. "Carbobenzoxy Chloride and Derivatives" Org. Synth. Coll. 3, 167-169 (1965).
Casara, P.J. et al. "Synthesis of Acid Stable 5'-0-Fluoromethyl Phosphonates of Nucleosides, Evaluation as Inhibitors of Reverse Transcriptase" BioOrg. Med. Chem. Letters 2(2), 145-148 (1992).
Casteel, D. et al. "Steric and Electronic Effects in the Aryl Phosphate to Arylphosphonate Rearrangement" Synthesis, 691-693 (1991).
Cavalier, J. et al. "New Highly Diastereoselective Synthesis of Phosphoramidates. A Route to Chiral Methyl p-Nitrophenyl Alkyphosphonates" Svnlett 1, 73-75 (1998).
CDC: Centers for Disease Control and Prevention: Pre-Exposure Prophylaxis (PrEP). (2013), located at <http://www.cdc.gov/hiv/prep/>, last visited on Sep. 15, 2013, 4 pages.
Cen et al., "Efficient Syntheses of Clofarabine and Gemcitabine from 2-Deoxyribonolactone", Nucleosides, Nucleotides and Nucleic Acids, 29, 113-122 (2010).
Chapman, H. et al., "Practical Synthesis, Separation, and Stereochemical Assignment of the PMPA Pro-Drug GS-7340", Nucleosides. Nucleotides & Nucleic Acids, vol. 20, Nos. 4-7, 621-628, (2001).
Chen, S. et al. "Design, Synthesis, and Biochemical Evaluation of Phosphonate and Phosphonamidate Analogs of Glutathionylspermidine as Inhibitors of Glutathionylspermidine Synthetase/Amidase from *Escherichia coli*" J. Med. Chem. 40(23), 3842-3850 (1997).
Chong, Y. et al. "2'-Fluoro-4'-thio-2',3'-unsaturated nucleosides: anti-HIV activity, resistance profile, and molecular modeling studies," Nucleosides, Nucleotides & Nucleic Acids 22(5-8):611-615. (May-Aug. 2003).
Chong, Y. et al. "Stereoselective Synthesis and Antiviral Activity of D-2',3' -Didehydro-2',3' -dideoxy-2' -fluoro-4' -thionucleosides" J. Med. Chem. 45, 4888-4898 (2002).
Chong, Y., et al., "Effects of fluorine substitution of cytosine analogues on the binding affinity to HIV-1 reverse transcriptase", Bioorganic & Medicinal Chemistry Letters, 14, 437-440, (2004).
Choo, H. et al. (Jan. 30, 2003). "Synthesis, Anti-HIV Activity, and Molecular Mechanism of Drug Resistance of L-2',3'-Didehydro-2',3'-Dideoxy-2'-Fluoro-4'-Thionucleosides," J. Med.Chem. 46(3):389-398.

Cihlar et al. (2008) "Design and Profiling of GS-9148, a Novel Nucleotide Analog Active Against Nucleoside-Resistant Variants of Human Immunodeficiency Virus Type 1, and Its Orally Bioavailable Phosphonoamidate Prodrug, GS-9131," Antimicrobial Agents and Chemotherapy, p. 655-665.
Cihlar et al. (2009) "Novel Nucleotide Human Immunodeficiency Virus Reverse Transcriptase Inhibitor GS-9148 with a Low Nephrotoxic Potential: Characterization of Renal Transport and Accumulation", Antimicrob Agents Chemother; 53(1):150-156.
Cihlar, T. (2008) "Amidate Prod rugs of Nucleoside Phosphonates: From Design to in Vivo Proof of Concept", Collection Symposium Series, 10:45-53.
Clark et al., "Mycophenolic Acid Analogues as Potential Agents Against West Nile Virus Infection", Dept. of Chemistry, Pharmasset, 1860 Montreal Road, Tucker, GA, 30084, 1 page, (2003).
Coe, D.M. et al. "Synthesis of Some Mimics of Nucleoside Triphosphates" J. Chem. Soc., Chem. Commun., 312-314 (1991).
Coleman, R. et al. "Synthesis of the aziridino [1,2-a] pyrrolidine Substructure of the Antitumor Agents Azinomycin A and B" J. Orn:. Chem. 57(22), 5813-5815 (1992).
Conklyn et al., "The JAK3 inhibitor CP-690550 selectively reduces NK and CD8+ cell numbers in cynomolgus monkey blood following chronic oral dosing", Journal of Leukocyte Biology. vol. 76, 1-8, (2004).
Corey, E.J. et al. "Selective Cleavage of Allyl Ethers Under Mild Conditions by Transition Metal Reagents" J. Orn. Chem. 38(18), 3224 (1973).
Crowell et al. (2017) "Highlights from the 24th Conference on Retroviruses and Opportunistic Infections Feb. 13-16, 2017, Seattle, Washington, USA" Journal of Virus Eradication 3:101-108.
D'Addona, D. et al. "Preparation of carbamates from amines and alcohols under mild conditions", Tetrahedron Letters, 42, 5227-5229 (2001).
Davies, L.C. et al. "Dinucleotide Analogues as Inhibitors of Thymidine Kinase, Thymidylate Kinase, and Ribonucleotide Reductase", J. Med. Chem. 31, 1305-1308 (1988).
De Clercq, "New Developments in Anti-HIV Chemotherapy", Current Medicinal Chemistry. vol. 8. No. 13, 1543-1572, (2001).
De Clercq, E. "New Developments in the Chemotherapy of Lentivirus (Human Immunodeficiency Virus) Infections: Sensitivity/Resistance ofHIV-1 to Nonnucleoside HIV-I-specific Inhibitors", Annals of the NY Academy of Sciences 724, 438-456 (1994).
De Clereq, "Highlights in the Development of New Antiviral Agents", Mini Reviews in Medicinal Chemistry. vol. 2 No. 2, 163-175, (2002).
De Lombaert, S. et al. "N-Phosphonomethyl Dipeptides and Their Phosphonate Prodrugs, a New Generation of Neutral Endopeptidase (NEP, EC 3.4.24.11) Inhibitors" J. Med. Chem. 37, 498-511 (1994).
Dvorakova et al., "Synthesis of 2'-Aminomethyl Derivatives of N-(2-(Phosphonomethoxy)ethyl) Nucleotide Analogues as Potential Antiviral Agents", J. Med. Chem., vol. 38, No. 17, 3263-3268, (1996).
Effenberger, F. et al. "2(1H)-Pyridon als Austrittsgruppe bei Acylierungsreaktionen Anwendungen in der Peptidchemie" Chem. Ber. 118, 468-482 (1985).
Efimov, V.A. et al. "Synthesis of DNA Analogues with Novel Carboxamidomethyl Phosphonamide and Glycinamide Internucleoside Linkages" Bioorganic & Medicinal Chemistry Letters 8, 1013-1018 (1998).
Eisenberg, E.J. et al. "Metabolism of GS-7340, A Novel Phenyl Monophosphoramidate Intracellular Prodrug of PMP A in Blood", Nucleosides, Nucleotides and Nucleic Acids 20(4-7), 1091-1098 (2001).
Elder et al., "The utility of sulfonate salts in drug development," Journal of Pharmaceutical Sciences, 2010, 99(7):2948-2961.
Esposito, D. et al. "HIV Integrase Structure and Function", Advances in Virus Research 52, 319-333 (1999).
Evans, "Exploring Structure—Activity Relationships of Transition State Analogues of Human Purine Nucleoside Phosphorylase", J. Med. Chem., vol. 46, No. 15, 3412-3423, (2003).
Farquhar, D. et al. "Biologically Reversible Phosphate-Protective Groups" J Pharm. Sci. 72, 324-325 (1983).

(56) References Cited

OTHER PUBLICATIONS

Frankel, A. et al., "HIV-1 Fifteen Proteins and an RNA", Annu. Rev. Biochem 67, 1-25 (1998).
Freeman, S. et al. "3 Prodrug Design for Phosphates and Phosphonates", Progress in Medicinal Chemistry 34, 112-147 (1997).
Fry et al., "Alkylations Using Methyltrialkoxyphosphonium Tetrafluoborate Salts. Synthetic and Mechanistic Aspects of Methyl, Ethyl, 2-Propyl, and 2-Octyl Group Transfers", J. Org. Chem., 49, 4877-4880 (1984).
Galeotti, N. et al. "A Straightforward Synthesis of Alpha—Amino Phosphonate Monoesters Using BroP or TPyCIU" Tetrahedron Letters 37(23), 3997-3998 (1996).
Gao et al. (2016) "L-Aspartic and L-Glutamic Acid Ester-Based Protides of Anticancer Nucleosides: Synthesis and Antitumoral Evaluation", Bioorganic & Medicinal Chemistry Letters, 26: 2142-2146.
Gobec et al., "Phosphonate inhibitors of antiget 85C, a crucial enzyme involved in the biosynthesis of the *Mycobacterium tuberculosis* cell wall", Bioorganic and Medicinal Chemistry Letters vol. 14, 3559-3562, (2004).
Griffin, B. et al. "D-Glucopyranose 6-Deoxy-6-phosphoric Acid" J. AM Chem. Society 78(10), 2336-2338 (1956).
Gumina et al., "Advances in antiviral agents for hepatitis B virus", Antiviral Chemistry & Chemotherapy, 12(1):93-117, (2001).
Hakimelahi, G. et al. "Design, Synthesis, and Structure-Activity Relationship of Novel Dinucleotide Analogs as Agents Against Herpes and Human . . . " J. Med. Chem. 38, 4648-4659 (1995).
Hanaoka, K. et al. (Jul. 19, 1999). "Antitumor Activity and Novel DNA-Self-Strand-Breaking Mechanism of CNDAC (1-(2-C-Cyano-2-Deoxy-13-D-Arabino-Pentofuranosyl) Cytosine) and its N4-Palmitoyl Derivative (CS-682)," Int. J. Cancer, 82(2):226-236.
Hansen, J. et al. "Partially Protected Polyamines", SYNTHESIS, 404-405 (1982).
Hartmann et al., "Toxicity associated with high dosage 9-[(2R,5R-2,5-dihydro-5-phosphonomethoxy)-2-furanyl]adenine therapy and attempts to abourt early FIV infection", Antiviral Research 36, 11-25, (1997).
Hegedus et al., "Synthesis of 4'-Methyl and 4'-cyano Carbocyclic 2',3'-Didehydro Nucleoside Analogues via 1,4-Addition to Substituted Cyclopentenones", J. Org. Chem., vol. 69, No. 24, 8492-8495, (2004).
Herczegh et al., "Osteoadsorptive bisphosphonate derivatives of fluoroquinolone antibacterials", J. Med. Chem., vol. 45, 2338-2341, (2002).
Herdewijn, P. et al. "3'-Substituted 2', 3'-Dideoxynucleoside Analogues as Potential Anti-HIV (HTLV-111/LAV) Agents", J. Med. Chem. 30, 1270-1278 (1987).
Hersh et al., "Synthesis and Structural Characterization of Trivalent Amino Acid Derived Chiral Phosphorus Compounds", J. Org. Chem., 69, 2153-2163 (2004).
Hildebrand, C. et al. "Sodium Salt Glycosylation in the Synthesis of Purine 2'-Deoxyribonucleosides; Studies oflsomer Distribution" J. Org. Chem. 57, 1808-1813 (1992).
Hirabayashi et al., "Bone-Specific Drug Delivery Systems", Clinical Pharacokinetics, vol. 42, No. 15, 1320-1330, (2003).
Holy et al., Synthesis ofN-(2-Phosphonylmethoxyethyl) Derivatives of Heterocyclic Bases Collect. Czech. Chem. Commun., vol. 54, 2190-2210 (1989).
Hostetler, "Nucleotides for topical treatment of psoriasis", CAS:127:185859, 2 pages, (1997).
Hottiger, M. et al. "Human Immunodeficiency Virus Type 1 Reverse Transcriptase", Biol. Chem. 377, 97-120 (1996).
Howell, H. et al. "Antiviral Nucleosides. A Stereospecific, Total Synthesis of 2'-Fluoro-2'-deoxy-beta-D-arabinofuranosyl Nucleosides" J. Org. Chem. 53, 85-88 (1988).
Huang et al., "Impact of solid state properties on developability assessment of drug candidates," Advances Drug Delivery Reviews, 2004, 56(3):321-334.

Jacob III, Peyton "Resolution of (Racemic)-5-Bromonornicotine. Synthesis of (R)- and (S)-Nornicotine of High Enantiomeric Purity" J. Org. Chem. 47, 4165-4167 (1982).
Jahne et al., "Preparation of Carbocyclic Phosphonate Nucleosides", Tetrahedron Letters. 33(37), 5335-5338 (1992).
Jain et al., "Characterization of Pharmacological Efficacy of VX-148, a New, Potent Immunosuppressive Inosine 5'-Monophosphate Dehydrogenase Inhibitor", Journal of Pharmacology and Experimental Therapeutics. vol. 302. No. 3, 1272-1277, (2002).
Jeong, L.S. et al. "Design, Synthesis, and Biological Evaluation of Fluoroneplanocin A as the Novel Mechanism-Based Inhibitor of S-Adenosylhomocysteine Hydrolase" Journal of Medicinal Chemistry 46(2), 201-203 (2003).
Karpenko et al., "Synthesis and Antitherpetic Activity of Acyclovir Phosphonates", Nucleosides, Nucleotides & Nucleic Acids, vol. 22, No. 3, 319-328, (2003).
Kato et al., "Enantio- and diastereoselective syntheis of 4'-.alpha.-substituted carbocvclic nucleosides", Tetrahedron: Asvmmetry. vol. 9, 911-914, (1998).
Kato et al., Stereoselective synthesis of 4' -.alpha.-alkycicathovir derivatives based on an asymmetric synthesis or chemo-enzymatic procedure, Chemical & Pharmaceutical Bulletin, vol. 49, No. 9, 1256-1264, (1999).
Katz, R. et al. "The Retroviral Enzymes" Annu. Rev. Biochem. 63, 133-173 (1994).
Kazimierczuk, Z. et al. "Synthesis of 2'-Deoxytubercidin, 2'-Deoxyadenosine, and Related 2'-Deoxynucleosides via a Novel Direct Stereospecific Sodium Salt Glycosylation Procedure" J. Am. Chem. Soc. 106, 6379-6382 (1984).
Khamnei, S. et al. "Neighboring Group Catalysis in the Design of Nucleotide Prodrugs" J. Med. Chem. 39, 4109-4115 (1996).
Khandazhinska YA, A.L. et al. "Carbocyclic Dinucleoside Polyphosphonates: Interactions with HIV Reverse Transcriptase and Antiviral Activity" J. Med. Chem. 45, 1284-1291 (2002).
Kielbasinski et al., "Lipase-promoted kinetic resolution of racemic, P-chiral hydroxymethylphosphonates and phosphinates", Tetrahedron: Asymmetry 9, 3283-3287 (1998).
Kilpatrick et al., "Intravenous and oral pharmacokinetic study ofBCX-1777, a novel purine nucleoside phosphorylase transition-state inhibitor, In vivo effects onblood 2'-deoxyguanosine in primates", International Immunopharmacology, vol. 3, 541-548, (2003).
Kim et al. (2015) Synthesis and Biological Evaluation of 9-Deazaadenine 5'-Deoxy-6',6'-Defluoro-Carbocyclic C-Nucleoside Phosphoric Acid Derivatives, Nucleosides, Nucleotides and Nucleic Acids, 34: 10, 708-728, Http://dx.doi.org/10.1080/15257770.2015.1071847.
Kim et al., "Regiospecific and Highly Stereoselective Electrophilic Addition to Furanoid Glycals: Synthesis of Phosphonate Nucleotide Analogues with Potent Activity against HIV", J. Org Chem . . . vol. 56. No. 8, 2642-2647, (1991).
Kim, C., et al. (1992) "Synthesis and Anti-HIV Activity of 9-[(2R,5R)-2,5-Dihydro-5-(Phosphonomethoxy)-2-Furanyl]-2,6-Diaminopurine", Bioogranic & Medicinal Chemistry Letters, 2(4):307-310.
Kinsky et al., "Circumvention of the methotrexate transport system by methotrexate-phosphatidylethanolamine derivatives effect of fatty acid chain length", Biochimica et Bionhvsica Acta vol. 921, 96-103, (1987).
Kinsky et al., "Effect of liposomes sensitized with methotrexate-.gamma.-dimyristoylphosphatidylethanolamine on cells that are resistant to methotrexate", Biochimica et Biophysica Acta, vol. 885, 129-135, (1986).
Kinsky et al "Inhibition of cell proliferation by putative metabolites and nondegradable analogs of methotrexate-.gama.-dimyristoylphosphatidylethanolamine", Biochimica et Biphysica Acta. vol. 917. No. 2, 211-218, (1987).
Ko et al., "Efficient synthesis of novel carbocyclic nucleosides via sequential Claisen rearrangement and ring-closing metathesis", Tetrahedron Letters. vol. 43, 6399-6402, (2002).
Kojima, T. et al. (Apr. 2006). "Crystalline Form Information From Multiwell Plate Salt Screening by Use of Raman Microscopy," Pharm. Res. 23(4):806-812.
Konakahara, T. et al. "A Convenient Method for the Synthesis of Activated NMethylcarbamates" Synthesis, 103-106 (1993).

(56) References Cited

OTHER PUBLICATIONS

Krayevsky et al., "5'-Hydrogenphosphonates and 5'-Methylphosphonates of Sugar Modified Pyrimidine Nucleosides as Potential Anti-HIV-1 Agents", Nucleosides & Nucleotides 1 H2-4), 177-196, (1992).
Krowczynki, L. "Drug Interaction," Chapter 17 in Outline of Clinical Pharmacy, 1982, pp. 323-342.
Krowczyr'lski, L. (1977). "Excipients for Manufacturing of Drug Forms," Chapter 4 in Outline of Drua Form Technoloav: A Textbook for Pharmacy Students, 3rd Edition.
Kumamoto, H. et al. (May 31, 2002). "Simple Entry to 3'-Substituted Analogues of Anti-HIV Agent Stavudine Based on an Anionic 0 --> C Stannyl Migration," J. Org. Chem. 67(11):3541-3547.
Kunz, H. et al. "71. Synthesis of the Glycopeptide Partial Sequence A80-A84 of Human Fibroblast Interferon" Helvetica Chimica Acta 68, 618-622 (1985).
LaFlamme et al. (2007) "Novel 2'-Fluoro Substituted Nucleotide HIV Reverse Transcriptase Inhibitor GS-9148 Exhibits Low Potential for Mitochondrial Toxicity in Vitro", 47th Interscience Conference on Antimicrobial Agents and Chemotherapy, Chicago.
Lee et al., "Structure-Activity Relationships of 2'-Fluoro-2',3'-unsaturated Dnucleosides as Anti-HIV-I Agents", J. Med. Chem., 45, 1313-1320, (2002).
Lee, K. et al. "Synthesis and Anti-HIV and Anti-HBV Activities of2'-Fluoro-2',3'-unsaturated L-Nucleosides" J. Med. Chem. 42, 1320-1328 (1999).
Lee, S. et al. "Large-Scale Aspects of Salt Formation: Processing of Intermediates and Final Products", Handbook of Pharmaceutical Salts: Properties, Selection, and Use, Chapter 8, 191-220 (2002).
Leff et al., "Antidiabetic PP AR.gamma Ligands. An update on Compounds in development", Curr. Med. Chem.—Imun., Endoc. & Metab. Agents, vol. 2, No. 1, 33-47, (2002).
Lewandowicz et al., "Achieving the Ultimate Physiological Goal in Transition State Analogue Inhibitors for Purine Nucleoside Phosphorylase", The Journal of Biological Chemistry, vol. 278, No. 34, 31454-31468, (2003).
Lochmuller, C.H. et al. "Chromatographic Resolution of Enantiomers Selective Review" Journal of Chromatography 113, 283-302 (1975).
Lu X et al. "Palladium-Catalyzed Reaction of Aryl Polyfluoroalkanesulfonates with 0, 0-Dialkyl Phosphonates" Synthesis, 726-727 (1987).
Ludewig et al., "Preparation of diester and onoster salts of phosphorous acid frm phosphorus (III) oxide and secondary, tertiary and aromatic alcohols," Zeitschrift fuer Chemie, 1984, 24(8): 290-291.
Ma, T. et al. "Synthesis and Anti-Hepatitis B Virus Activity of 9-(2-Deoxy-2-fluoro- Beta-L-arabinofuranosyl)ourine Nucleosides" J. Med. Chem. 40, 2750-2754 (1997).
Mackman et al. "Discovery of GS-9131: Design, synthesis and optimization of amidate prodrugs of the novel nucleoside phosphonate HIV reverse transcriptase (RT) inhibitor GS-9148", Bioorganic & Medicinal Chemistry. vol. 18, 3606-3617, (2010).
Maffre-Lafon, D. et al. "Solid Phase Synthesis of Phosphonopeptides from Fmoc Phosphonodipeptides" Tetrahedron Letters 35(24), 4097-4098 (1994).
Margolin et al., "AMP Deaminase as a Novel Practical Catalyst in the Synthesis of 6-0xopurine Ribosides and Their Analogs", Journal of Organic Chemistry, 59(24), 7214-7218 (1994).
Marquez, V.E. et al. "Acid-Stable 2'-Fluoro Purine Dideoxynucleosides as Active Agents against HIV" J. Med. Chem. 33, 978-985 (1990).
Maruyama et al., (1994) "Synthesis and Anti-HIV Activity of 6-Substituted Purine 2'-Deoxy-2'-fluororibosides," Nucleosides and Nucleotides, 13:1-3, 527-537.
Maynard, J. A. et al. "Organophosphorus Compounds II. Preparation of Phosphoric Acid Esters Using the Dicyclohexylcarbodiimide Reagent" Aust. J. Chem. 16, 609-612 (1963).
McKenna, C. et al. "Functional Selectivity in Phosphonate Ester Dealkylation with Bromotrimethylsilane" J.C.S. Chem. Comm. , 739 (1979).
Melvin, L.S. "An Efficient Synthesis of 2-Hydroxyphenylphosphonates" Tetrahedron Letters 22(35), 3375-3376 (1981).

Menendez-Arias, Luis et al., "Targeting HIV: antiretroviral therapy and development of drug resistance", TRENDS in Pharmacological Sciences, vol. 23, No. 8, 381-388, (2002).
Mikhailopulo, I. et al. "Pyrophosphoryl Derivatives of 1-(2-Deoxy-3-0-Phosphonomethyl-Beta- and -Alpha-D-erythro-Pentofuranosyl)Thymine: Synthesis and Substrate Properties Towards Some DNA Polymerases" Nucleosides, Nucleotides, and Nucleic Acids 19{10-12), 1885-1909 (2000).
Mikhailopulo, I.A. et al. (Jul. 25, 2003). "2'-Chloro-2',3'-Dideoxy-3'-Fluoro-d-Ribonucleosides: Synthesis, Stereospecificity, Some Chemical Transformations, and Conformational Analysis," J. Org. Chem. 68(15):5897-5908.
Mikhailopulo, I.A. et al. (May 12, 1993, e-pub. Jan. 25, 2006). "Synthesis of 2'-Azido-2',3'-Didehydro-2',3'-Dideoxythymidine," Liebigs Annalen der Chemie 5:513-519.
Mitchell, A. et al. "Bioreversible Protection for the Phospho Group: Bioactivation of the Di(4 acyloxybenzyl) Phosphoesters . . . " J. Chem. Soc. Perkin Trans 1, 2345-2353 (1992).
Mitsunobu, Oyo "The Use of Diethyl Azodicarboxylate and Triphenylphosphine in Synthesis and Transformation of Natural Products" Synthesis, 1-28 (1981).
Moon, HR et al "Synthesis of 2', 3' -didehydro-2',3' -dideoxy-2' -fluoro apionucleosides as potential antiviral agents" J. Chem. Soc., Perkin Trans. 1, 1800-1804 (2002).
Morgan, B. et al. "Structure-Based Design of an Inhibitor of the Zinc Peptidase Thermolysin" J. AM. Chem. Soc. 116(8), 3251-3260 (1994).
Morgans, et al., "5-Substituted derivatives of mycophenolic acid", CAS: 124:86709 (1995).
Morr, M. et al "Formation of Phostonic Acids During the Reduction of Azidonucleosidephosphonic Acids" Tetrahedron Letters 42, 8841-8843 (2001).
Muesing, M. et al. "Nucleic acid structure and expression of the human AIDS/lymphadenopathy retrovirus" NATURE 313(7), 450-458 (1985).
Musiol, H. et al. "Synthesis of Phosphonamidate Peptides" J. Org. Chem. 59(21):6144-6146 (1994).
Ohashi, K. et al. "Synthesis of Phosphonosphingoglycolipid Found in Marine Snail Turbo Cornutus" Tetrahedron Letters 29(10), 1189-1192 (1988).
Okamoto, Y. et al. "Optical resolution of dihydropyridine enantiomers by Highperformance liquid chromatography using phenylcarbamates . . . " Journal of Chromatography 513, 375-378 (1990).
Ono-Nita et al., "Novel Nucleoside Analogue MCC-478 (LY582563) Is Effective against Wild-Type or Lamivudine-Resistant Hepatitis B Virus", Antimicrobial Agents and Chemotherapy. vol. 46 No. 8, 2602-2605, (2002).
Pankiewicz et al., "Novel Mycophenolic Adenine Bis(phosphonate) Analogues As Potential Differentiation Agents against Human Leukemia", J. Med. Chem., vol. 45. No. 3, 703-712, (2002).
Paquet, Alenka "Introduction of 9-fluorenylmethyloxycarbonyl, trichloroethoxycarbonyl, and benzyloxycarbonyl amine protecting groups into . . . " Can. J. Chem. 60, 976-980 (1982).
Parang, Ket al. "Novel Approaches for Designing 6-0-Ester Prodrugs of 3'-Azido-2', 3'-Dideoxythymidine (AZT)" Current Medicinal Chemistry 7(10), 995-1039 (2000).
Patani, G., et al, (1996) "Bioisosferism: A Rational Approach in Drug Design", Chem. Rev. 96:3147-3176.
Patois, C. et al. "2-Alkyl-5, 5-dimethyl-1,3,2-dioxaphosphorinan-2-ones alpha-Lithiated Carbanions. Synthesis, Stability, and Conformation" J. Chem. Soc. Perkin Trans. (1), 1577-1581 (1990).
Pauwels et al., "Investigations on the Anti-HIV Activity of 2', 3'-Dideoxyadenosine Analogues with Modifications in Either the Pentose or Purine Moiety", Biochemical Pharmacology. vol. 37. No. 7, 1317-1325, (1988).
PCT International Search Report and Written Opinion in International Appln. No. PCT/US2018/044415, dated Jan. 8, 2019, 20 pages.
PCT Third Party Observation in International Appln. No. PCT/US2018/044415, dated Dec. 2, 2019, 16 pages.
Petrakis, K. et al. "Palladium-Catalyzed Substitutions of Initiates Derived from Tyrosine-Containing Peptides and Simpler Hydroxyarenes Forming . . . " J. Am. Chem. Soc. 109, 2831-2833 (1987).

(56) References Cited

OTHER PUBLICATIONS

Porche, D. J. "State of the Art: Antiretroviral and Prophylactic Treatments in HIV/AIDS", Nursing Clinics of North America 34, 95-112 (1999).
Prashad, Mahavir et al., "An Efficient and Large-Scale Enantioselective Synthesis of PNP405: A Purine Nucleoside Phosphorylase Inhibitor", J. Org. Chem .. vol. 67. No. 19, 6612-6617, (2002).
Puech, F. et al. "Intracellular delivery of nucleoside monophosphates through a reductase-mediated activation process" Antiviral Research 22, 155-174 (1993).
Pungente, M. et al. "Synthesis and Stereochemical Elucidation of a 14-Membered Ring Phosphonate", Organic Letters 3(5), 643-646 (2001).
Quast, H. et al. "Herstellung von Methylphosphonsaure-dichlorid" Synthesis, 490 (1974) [with English Language Translation, 3 pages.]
Ray et al., "Intracellular Metabolism of the Nucleotide Prodrug GS-9131, a Potent Anti-Human Immunodeficiency Virus Agent," Antimicrobial Agents and Chemotherapy, 2008, 52: 648-654.
Ray et al., "Role of Purine Nucleoside Phosphorylase in Interactions between 2', 3'-Dideoxyinosine and Allopurinal, Ganciclovir, or Tenofovir", Antimicrobial Agents and Chemotherapy. vol. 48. No. 4, 1089-1095, (2004).
Redmore, Derek "Phosphorus Derivatives of Nitrogen Heterocycles. 2. Pyridinephosphonic Acid Derivatives" J. Org. Chem. 35(12), 4114-4117 (1970).
Roach et al. "Fluorescence Detection of Alkylphosphonic Acids Using p-(9-Anthroyloxy)phenacyl Bromide" Analytical Chem. 59, 1056-1059 (1987).
Roberts, Stanley M., "Development of the route to the new anti-AIDS drug abacavir: A highlight of academic/industry laison", Drugs. 1(8):896-899, (1998).
Rosenberg, I. et al. "Synthesis of Potential Prodrugs and Metabolites of 9-(S)-(3-Hydroxy-2-Phosphonylmethoxypropyl) Adenine" Collect. Czech. Chem. Commun. 52, 2792-2800 (1987).
Rosowsky et al., "Methotrexate Analogues, 32, Chain Extension, .alpha.-Carboxyl Replacement by Sulfonate and Phosphonate: Effect on Enzyme Binding and Cell-Growth Inhibition", J. Med. Chem., vol. 31, No. 7, 1326-1331, (1988).
Rosowsky et al., "Methotrexate Analogues-27", Biochemical Pharmacology. vol. 35, No. 19, 3327-3333, (1986).
Saady, M. et al. "Selective Monodeprotection of Phosphate, Phosphite, Phosphonate, and Phosphoramide Benzyl Esters" J. Orn. Chem. 60, 2946-2947 (1995).
Sarma et al., "Solid forms of pharmaceuticals: polymorphs, salts, and cocrystals," Korean Journal of Chemical Engineering, 2011, 28(2):315-322.
Sasaki, T. et al. (1971). "Chemistry of Cyanoacetylenes. Part X. Further Studies on the Reactions of Cyano-Ynamines with Hydrogen Halides and Bromine," J. Chem. Soc. C. 18:3056-3060.
Sato et al., "Synthesis and Hypnotic and Anti-Human Immunodeficiency Virus-1 Activities of N 3-Substituted 2'-Deoxy-2'-fluorouridines," Chem. Pharm. Bull. 42(3) 595-598 (1994).
Schon, I. et al. "9-Fluorenylmethyl Pentafluorophenyl Carbonate as a Useful Reagent for the Preparation ofN-9-Fluorenylmethyloxycarbonylamino ... " Synthesis 303-305 (1986).
Schultz, "Prodrugs of biologically active phosphate esters", Bioorganic & Medicinal Chemistry. vol. 11, 885-898, (2003).
Sekiya et al., "2-Amino-6-arylthio-9-[2-(phosphonomethoxy) ethyl] purine Bis(2,2,2-trifluoroethyl) Esters as Novel HBV-Specific Antiviral Reagents", Journal of Medicinal Chemistry, vol. 45, No. 14, American Chemical Society, 3138-3142, (2002).
Serafinowska, H. et al. "Synthesis and in Vivo Evaluation of Prodrugs of 9-[2-(Phosphonomethoxy)ethoxy]adenine" J. Med. Chem. 38, 1372-1379 (1995).
Sharma, S. et al. "Spermexatin and Spermaxatol: New Synthetic Spermidine-Based Siderophore Analogues" J. Med. Chem. 32, 357-367 (1989).
Shi et al., "Plasmodium falciparum Purine Nucleoside Phosphorylase", The Journal of Biological Chemistry. vol. 279 No. 18, 18103-18106, (2004).

Shirokova, E.A. "New Lipophilic Derivatives of AZT and d4T 5'-Phosphonates", Nucleosides, Nucleotides and Nucleic Acids 22(5-8), 981-985 (2003).
Siddiqui, A .Q. et al. "The Presence of Substituents on the Aryl Moiety of the Aryl Phosphoramidate Derivative of D4T Enhances Anti-HIV Efficacy in Cell Culture: A Structure-Activity Relationship" Journal of Medicinal Chemistry 42(3), 393-399 (1999).
Silverberg, L. et al. "A Simple, Rapid and Efficient Protocol for the Selective Phosphorylation of Phenols with Dibenzyl Phosphite" Tetrahedron Letters 37(6), 771-774 (1996).
Sintchak et al., "The structure of inosine 5'-monophosphate dehydrogenase and the design of novel inhibitors", Immunonharmachology. vol. 47, 163-184, (2000).
Smith, M. et al. "Development and significance of nucleoside drug resistance in infection caused by the human immunodeficiency virus type 1" Clin. Invest. Med. 17(3), 226-243 (1994).
Smith, R. et al. "A novel MyD-1 (SIRP-1) signaling pathway that inhibits LPSinduced TNF production by monocytes" Blood 102(7), 2532-2540 (2003).
Squires, "An introduction to nucleoside and nucleotide analogues", Antiviral Therapy. 6(Suppl.3), 1-14, (2001).
Srinivas et al., "Metabolism and In Vitro Antiretroviral Activities of Bis(Pivaloyloxymethyl) Prodrugs of Acyclic Nucleoside Phosphonates", Antimicrobial Agents and Chemotherapy. vol. 37. No. 10, American Society for Microbiology, 2247-2250, (1993).
Stahl, P.H. "Appendix," Handbook of Pharmaceutical Salts: Properties, Selection, and Use, 329-350 (2002).
Stahl, P.H. et al. "Monographs on Acids and Bases", Handbook of Pharmaceutical Salts: Prooerties Selection. and Use. Chapter 12, 265-327 (2002).
Stamm, H. et al. "Reactions with Aziridines XXI the (Michaelis-) Arbuson Reactionwith N-Acyl Aziridines and Other Amidoethylations at Phosphorus" Tetrahedron Letters 21, 1623-1626 (1980).
Sturtz et al., "A study of the delivery-targeting concept applied to antineoplasic drugs active on human osteosarcoma, I. Synthesis and biological activity in nude mice carrying human osteosarcoma xenografts of gem-bisphosphonic methotrexate analogues", Eur J. Med. Chem., vol. 27, No. 8, 825-833, (1992).
Sturtz et al., "Amethopterin (methotrexate) phosphonoglutamic acid analogs. Part II. Dihydrofolate reductase inhibition" CAS:101:143560, 1 page, (1984).
Sturtz et al., "Analogues phosphonoglutamiques d'amethopterine (methotrexate)",Eur. J. Med. Chem—Chim. Ther., vol. 19, No. 3, 267-273, (1984). [English Abstract on first page.]
Sturtz et al., "Su rune nouvelle approche de pharmacomodulation du methotrexate:synthese d'analogues gem-diphosphoniques d'amethopterine et de la N-10 deaza amethopterin", Medicinal Chemis!n'., C.R. Acad. Sci. Paris, vol. 10, No. 2, Academie des Sciences, 739-742, (1990). [English Abstract on first page.]
Sturtz et al., "Synthesis of gem-bisphosphonic methotrexate conjugates and their biological response towards Walker's osteosarcoma", Eur. J. Med. Chem., 28:899-903, (1993).
Sun, C. et al. "A General Synthesis of Dioxolenone Prodrug Moieties" Tetrahedron Letters 43, 1161-1164 (2002).
Szabo, T. et al. "Solid Phase Synthesis of 5'-Methylenephosphonate DNA" Nucls. & Nuclt 14(3-5), 871-874 (1995).
Taiwan Office Action in Taiwan Appln. No. 170126544, dated Apr. 18, 2019, 5 pages (with English translation).
Tang, T. et al. The tert-Butanesulfinyl Group: An Ideal Chiral Directing Group and Boe-Surrogate for the Asymmetric Synthesis and Applications of J. Org. Chem. 64, 12-13 (1999).
Tarrago-Litvak, L. et al. "The reverse transcriptase of HIV-1: from enzymology to therapeutic intervention" The FASEB Journal 8, 497-503 (1994).
Thomson, W. et al. "Synthesis and Bioactivation ofBis(aroyloxymethyl) and Mono(aroyloxymethyl) Esters of Benzylphosphonate and ... " J. Chem. Soc. Perkin Trans. 19, 2303-2308 (1993).
Toyota, A. et al. (Jun. 25, 1998). "a-Fluorination of 6-Phenylsulfinyl-2-Azabicyclo [2.2.1]heptan-3-0ne and Synthesis of 2'-Fluoro Substituted Calbovir," Tetrahedron Letters 39(26):4687-4690.
TRUVADA® label revision approved on Jul. 16, 2012, NDA No. 021752, Reference ID 3159758, 38 pages.

(56) References Cited

OTHER PUBLICATIONS

Van Der Laan, A.C. et al. "An Approach Towards the Synthesis of Oligomers Containing a N-2 Hydroxyethyl-aminomethylphosphonate Backbone: A Novel PNA Analogue" Tetrahedron Letters 37(43), 7857-7860 (1996).
Van Der Laan, A.C. et al. "Optimization of the Binding Properties of PNA-(5')-DNA Chimerae" Bioorn. Med. Chem. Letters 8, 663-668 (1998).
Vieira De Almeida, M. et al. "Synthesis of Deoxy Phosphatidylinositol Analogues and Phosphonate Isosters ofIns(1,4,5)P3" Tetrahedron Letters 55, 12997-13010 (1999).
Vielhaber, Bernd, Bericht vom 3rd International Workshop on Salvage Therapy for HIV-Infection, Deutsche Aids-Hilfe e.V. FaxReport zu HIV and AIDS, 12-14, (2000). [English translation of Abstract—4 pages].
Von Der Helm, K. "Retroviral Proteases: Structure, Function and Inhibition From a Non-Anticipated Viral Enzyme to the Target of a Most Promising HIV Therapy" Biol. Chem. 377, 765-774 (1996).
Waegell et al. "A420983, a novel, small molecule inhibitor of LCK prevents allograft rejection", Transplantation Proceedings, vol. 34, 1411-1417, (2002).
Wang et al. (2015) "Adenine: An Important Drug Scaffold for the Design of Antiviral Agents", Acta Pharmaceutica Sinica B, 5(5) :431-441.
Watanabe, Y. et al. "Dibenzyl Phosphorofluoridate, A New Phosphorylating Agent" Tetrahedron Letters 29(45), 5763-5764 (1988).
Wermuth, C.G. et al. "Selected Procedures for the Preparation of Pharmeaceutically Acceptable Salts", Handbook of Pharmaceutical Salts: Prouerties, Selection, and Use, Chanter 11, 249-263 (2002).
Wessig, P. et al. "A Convenient One-Pot Conversion ofN-Boc-B-Aminoalcohols into N-Boc-Aziridines" Svnlett 8, 893-894 (1997).
West, Solid-State Chemistry and Its Applications, John Wiley & Sons, 3 pages, (1984).
White et al. (2017) "GS-9131 is a Novel NRTI with Activity Against NRT1-Resistant HIV-1" Abstract.
White et al. (2017) "GS-9131 is a Novel NRTI with Activity Against NRT1-Resistant HIV-1" Oral Presentation at the Conference on Retroviruses and Opportunistic Infections (CROI), Seattle, WA.
White et al. (2017) "GS-9131 is a Novel NRTI with Activity Against NRT1-Resistant HIV-1" Poster Presented at the Conference on Retroviruses and Opportunistic Infections (CROD, Seattle, WA.
Wissner, A. et al. "Analogues of Platelet Activating Factor. 6 Mono- and Bis-Aryl Phosphate Antagonists of Platelet Activating Factor" J. Med. Chem. 35, 1650-1662 (1992).
Woltermann, C.J. et al. (Apr. 5, 2004). "A Stereoselective Synthesis of 9-(3-0-benzyl-5-0-Tetrahydropyranyl-13-D-Arabinofuranosyl)Adenine, a Potentially Useful Intermediate for. Ribonucleoside Synthesis," Tetrahedron 60(15):3445-3449.
Wroblewski et al., "Synthesis of (1 R,2S)- and (1S,2S)-3-(4-carbamoyl-1,2,3-triazol-1-yl )-1,2-dihydroxypropyl phosphonate-s", Tetrahedron: Asymmetry, vol. 15, 1457-1464, (2004).
Xu et al., "Cobicistat (GS-9350): A Potent and Selective Inhibitor of Human CYP3A as a Novel Pharmacoenhancer," ACS Med. Chem Lett., 2010, 1(5):209-13.
Yamada, K. et al. (2002). "Reactions of 1-Methoxy-3-(2-nitrovinyl)indole with Nucleophiles: An Interesting Solvent Effect and a Novel Preparation of 3-Substituted 1-Methoxyindoles," Heterocycles 57(7): 1231-1234.
Yamauchi, K. et al. "Synthesis of Peptides Analogues Containing (2-aminoethyl)phosphonic acid( ciliatine )" J. Orn:. Chem. 49(7), 1158-1163 (1984).
Zemlicka, J. et al. "Nucleosides. XV. Decarboxylative Elimination of 2'—Deoxynucleodise Uronic Acids" J. AM. Chem. Soc. 94(9), 3213-3218 (1972).
Zhou, W. et al. "Synthesis, Structure-Activity Relationships, and Drug Resistance of beta-D-3'-Fluoro-2',3'-Unsaturated Nucleosides as Anti-HIV Agents" J. Med. Chem.47, 3399-3408 (2004).

\* cited by examiner

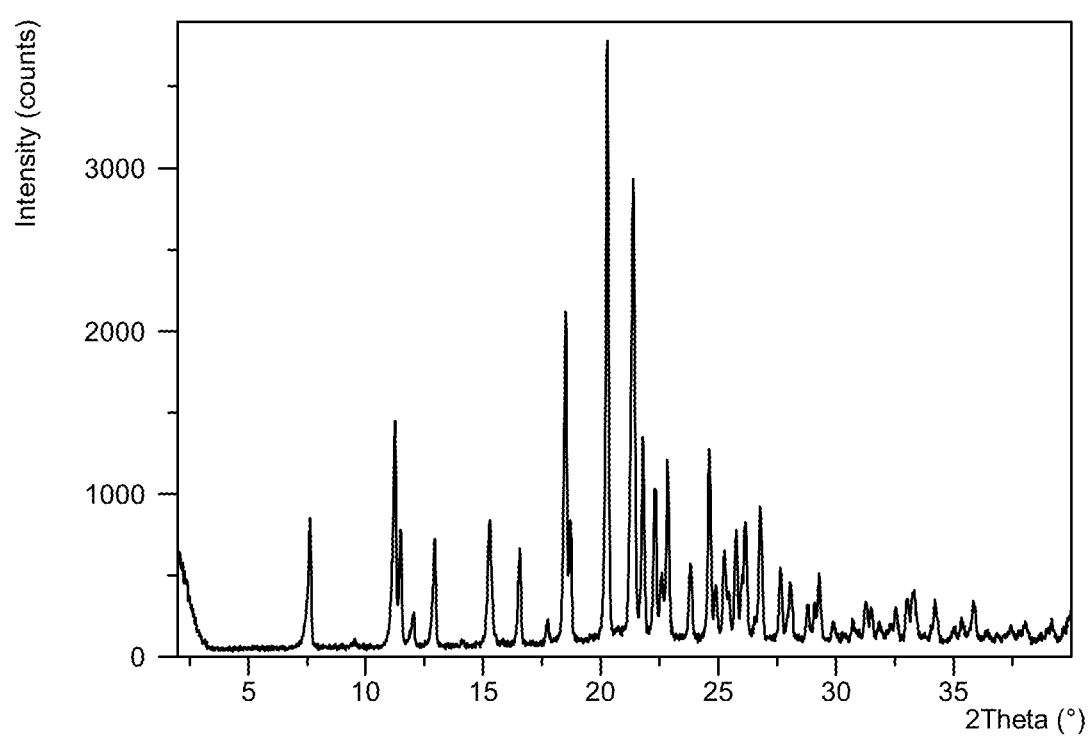
FIG. 1: XRPD pattern of the compound of Formula I Form I

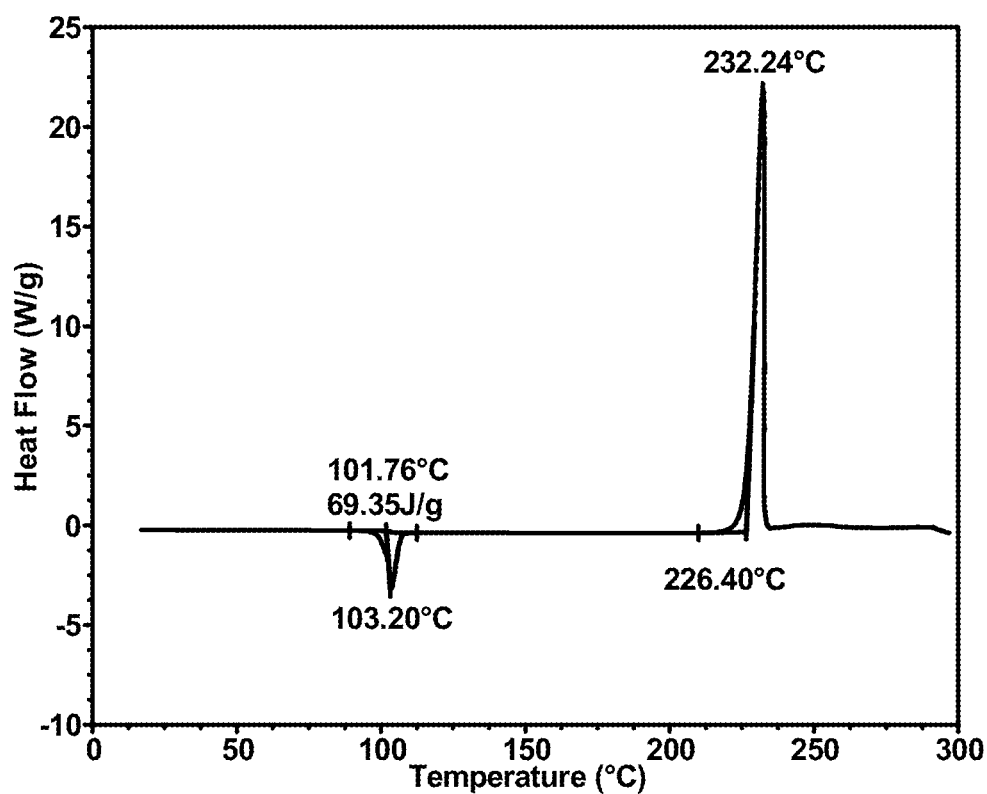
FIG. 2: DSC thermogram of the compound of Formula I Form I

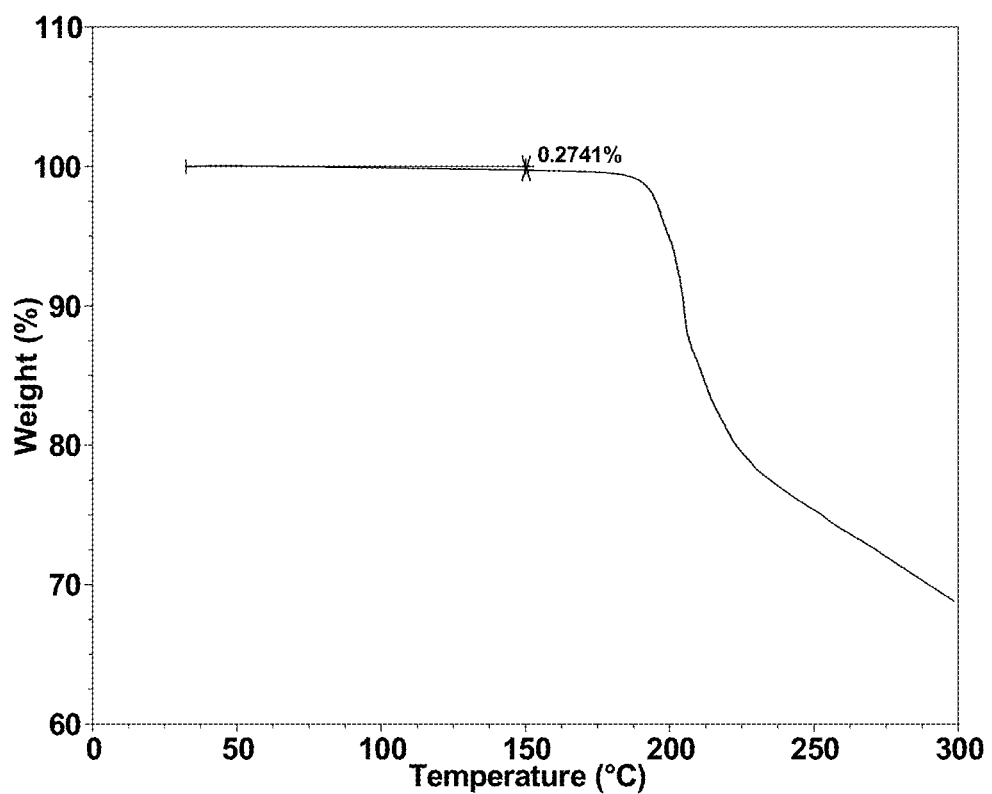
FIG. 3: TGA thermogram of the compound of Formula I Form I

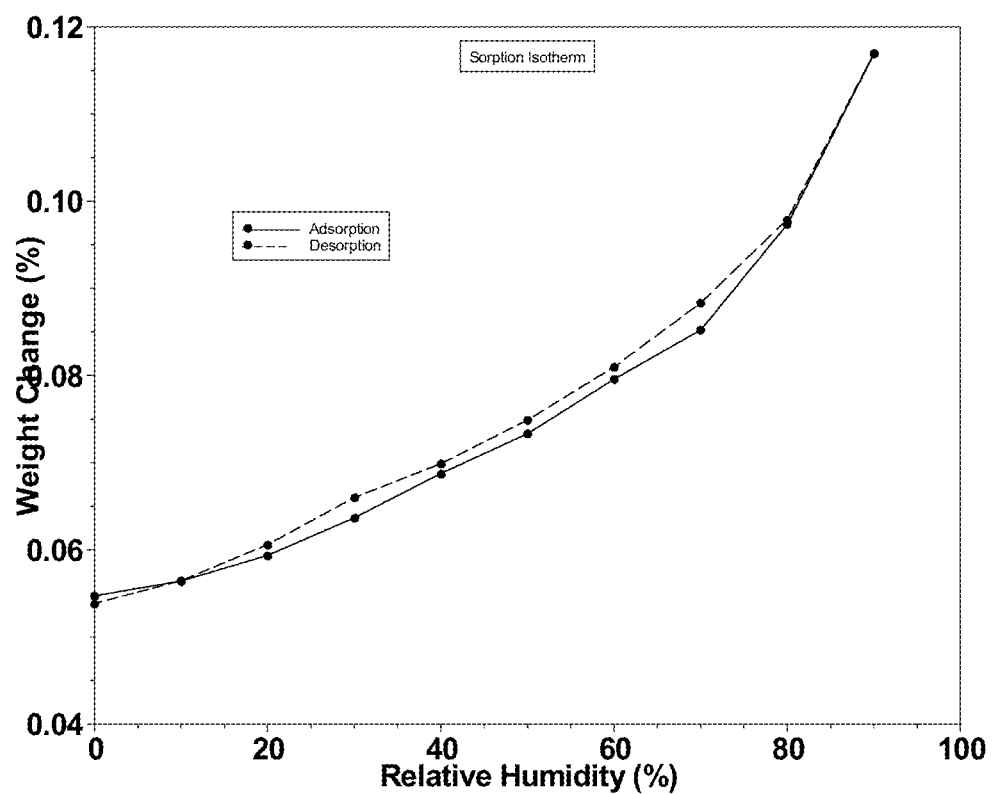
FIG. 4: DVS isotherm of the compound of Formula I Form I

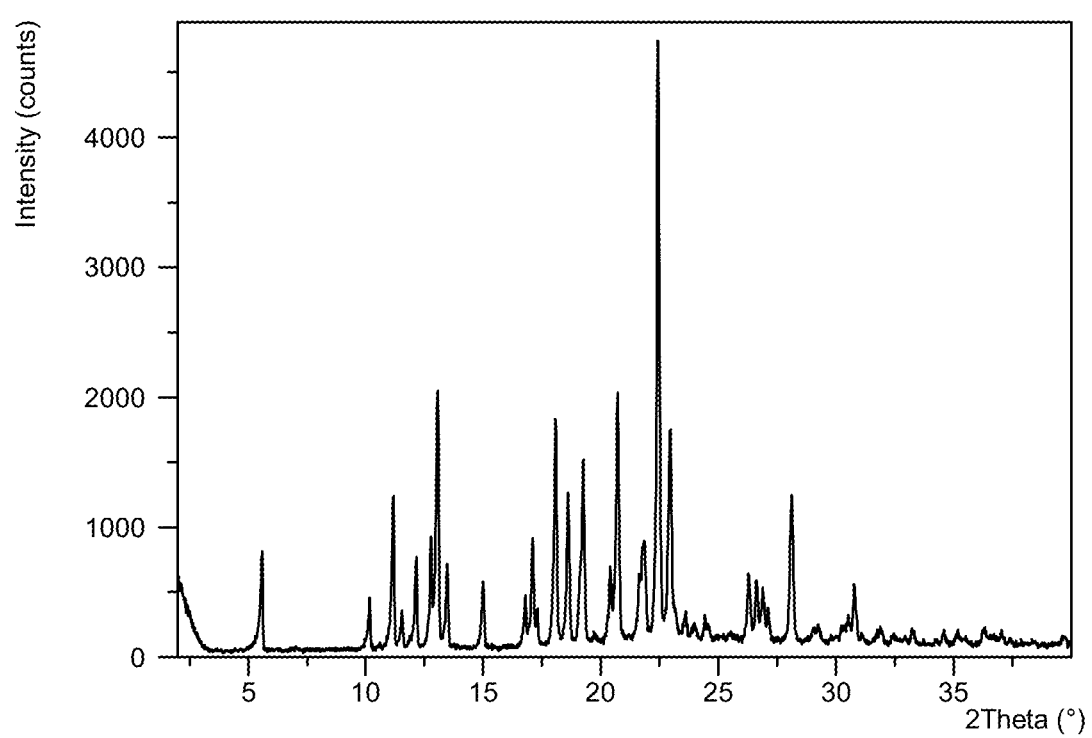
FIG. 5: XRPD pattern of the compound of Formula I Form II

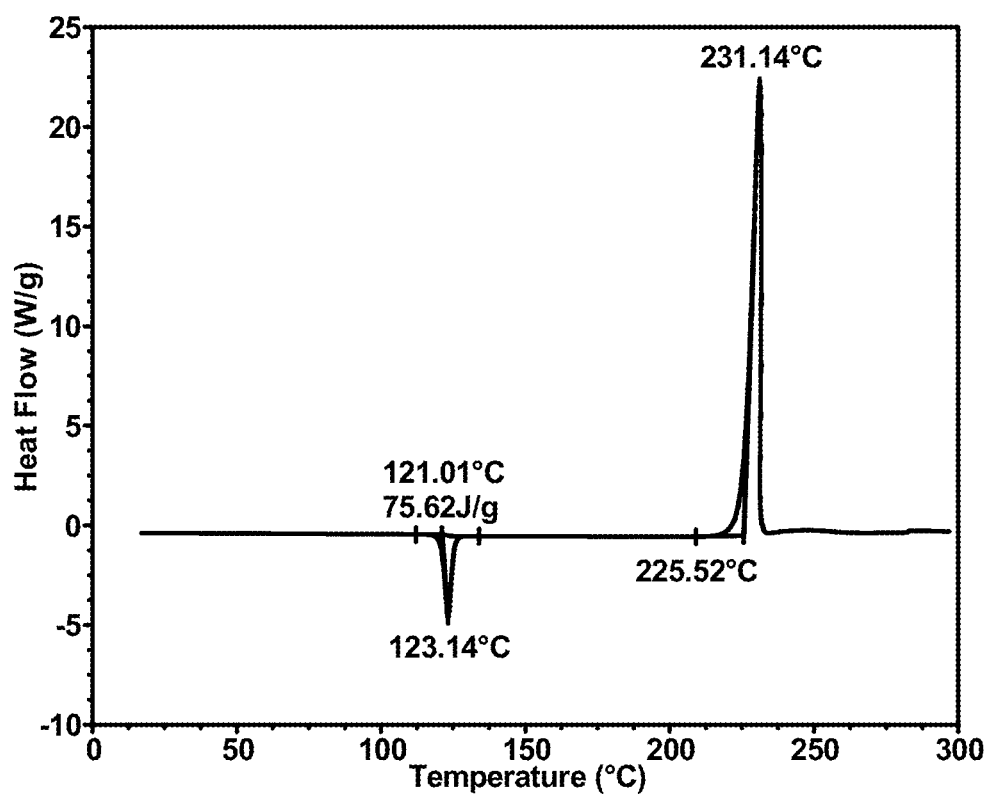
FIG. 6: DSC thermogram of the compound of Formula I Form II

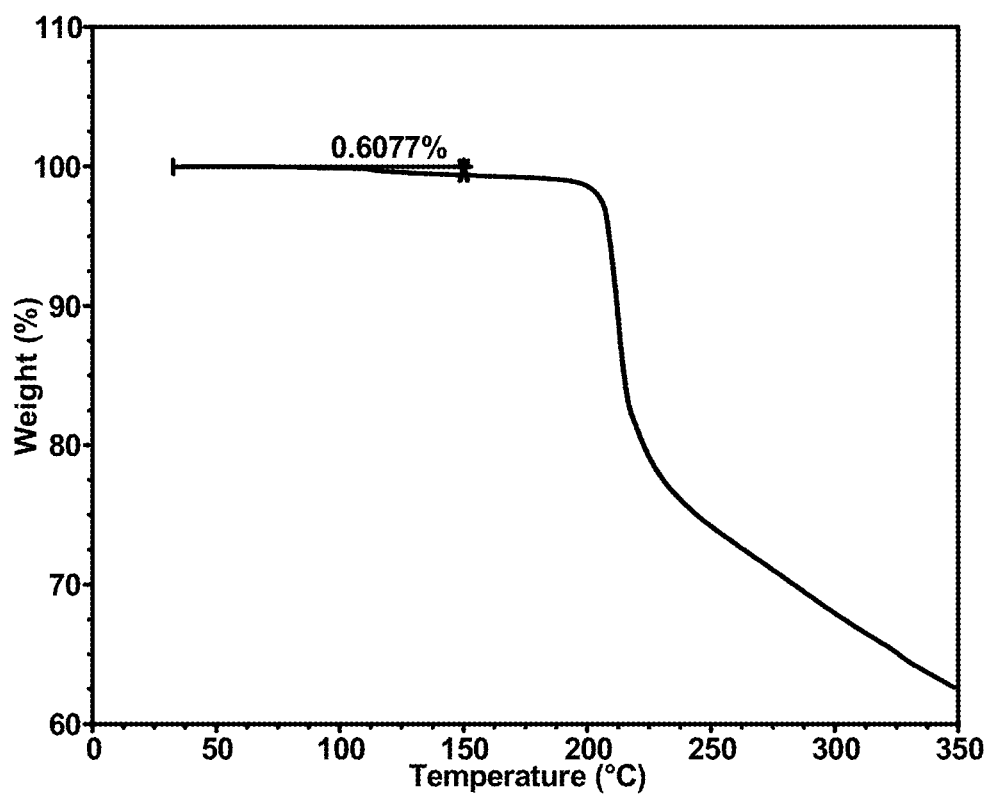
FIG. 7: TGA thermogram of the compound of Formula I Form II

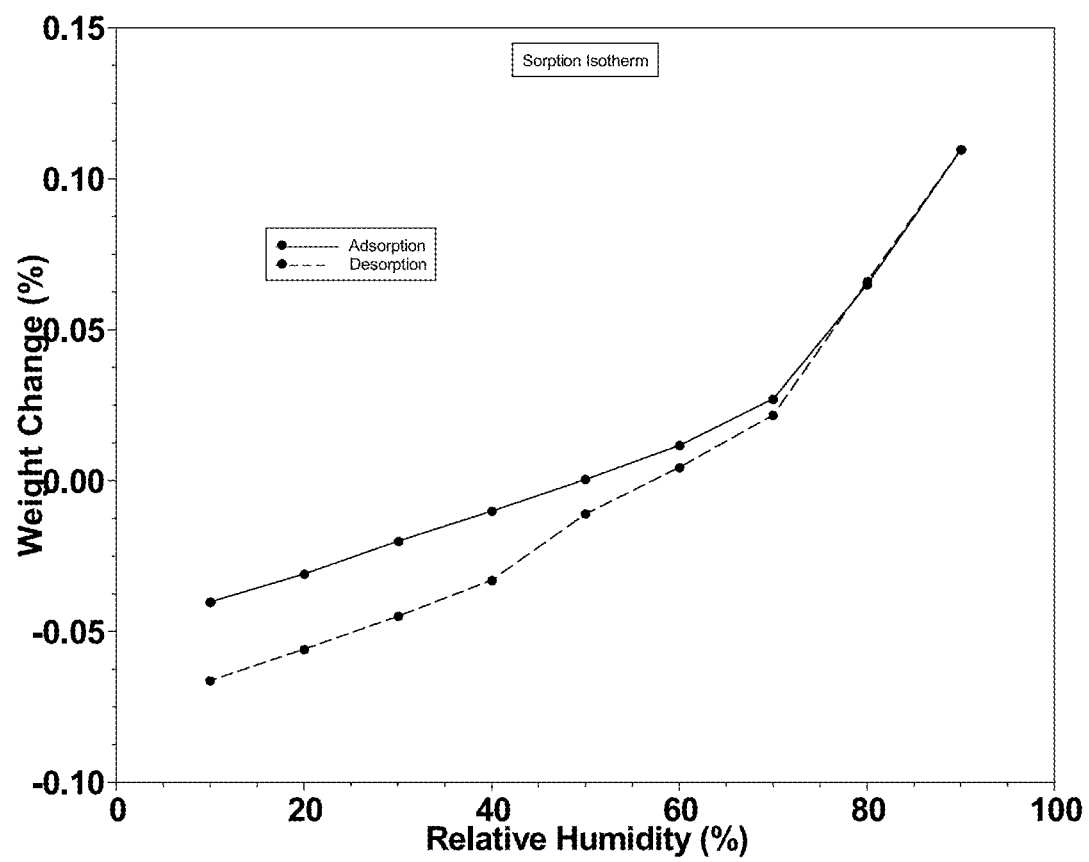
FIG. 8: DVS spectrum of the compound of Formula I Form II

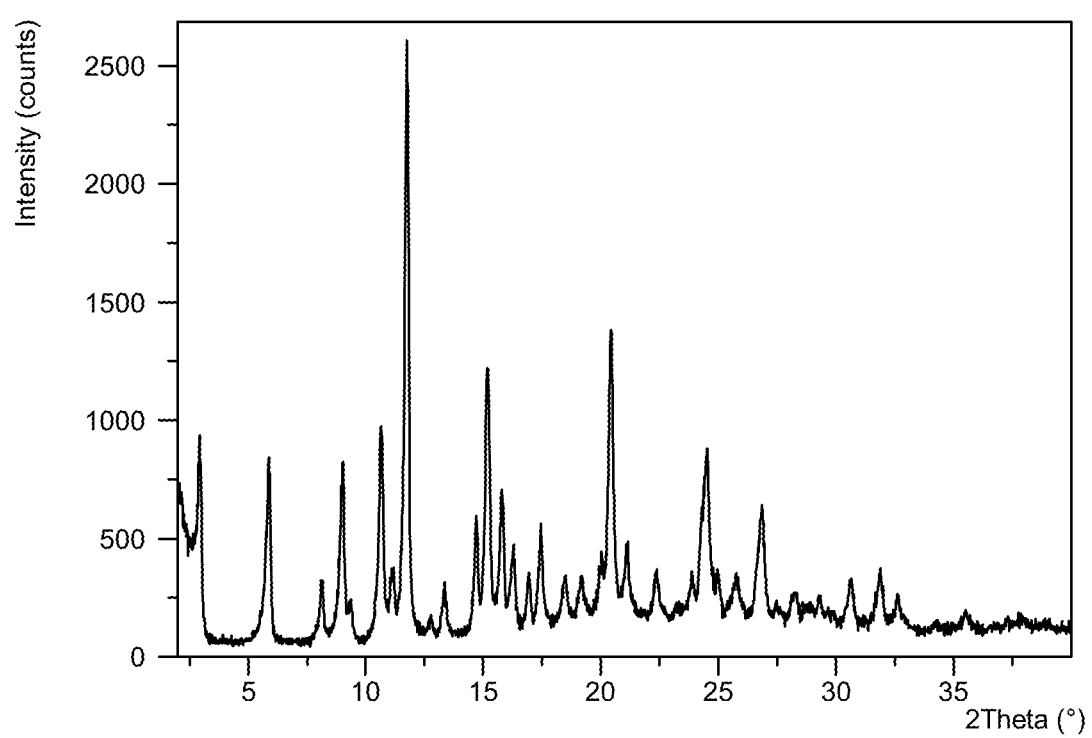
FIG. 9: XRPD pattern of the compound of Formula I Vanillate Form I

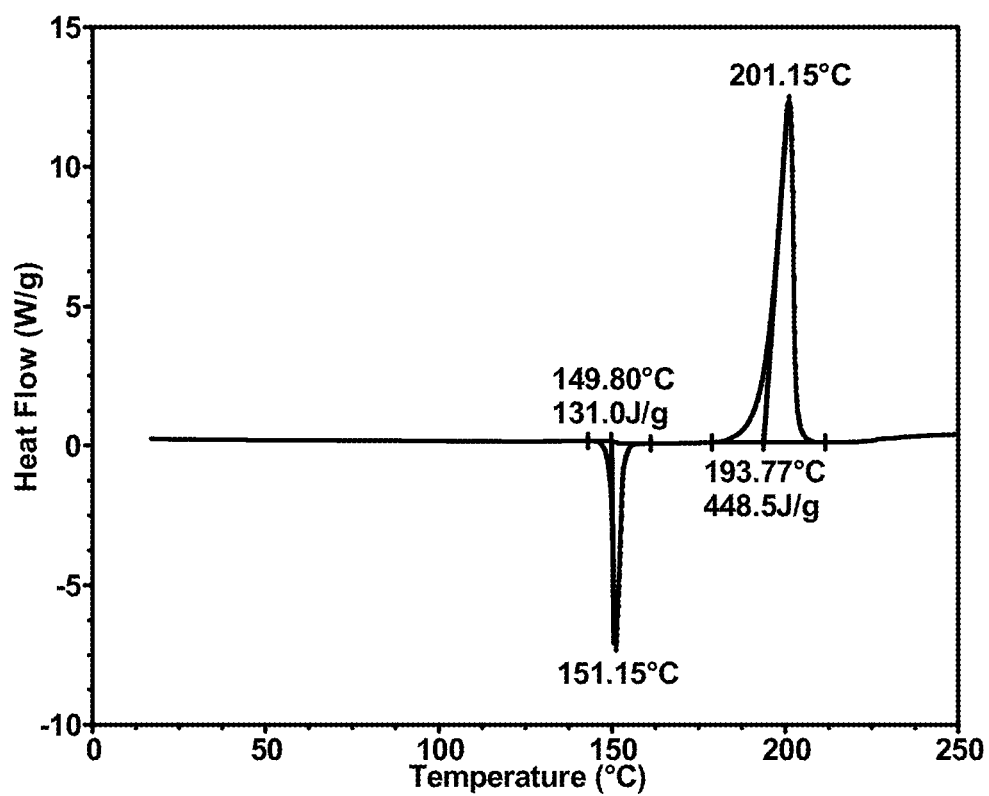
FIG. 10: DSC thermogram of the compound of Formula I Vanillate Form I

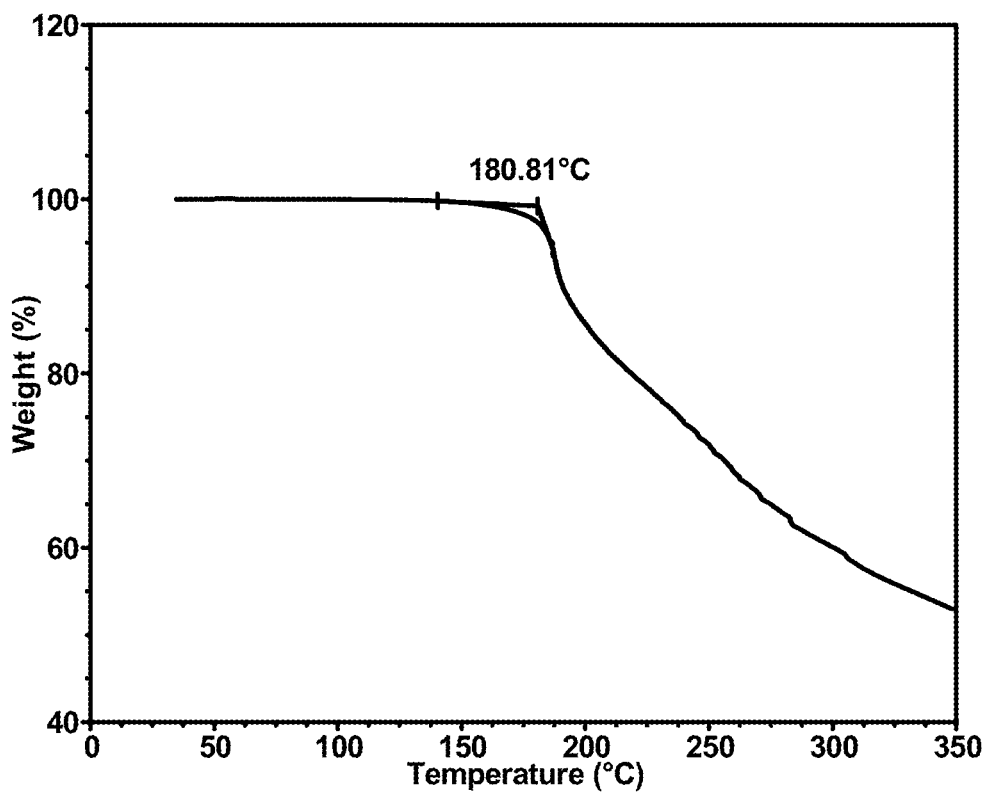
FIG. 11: TGA thermogram of the compound of Formula I Vanillate Form I

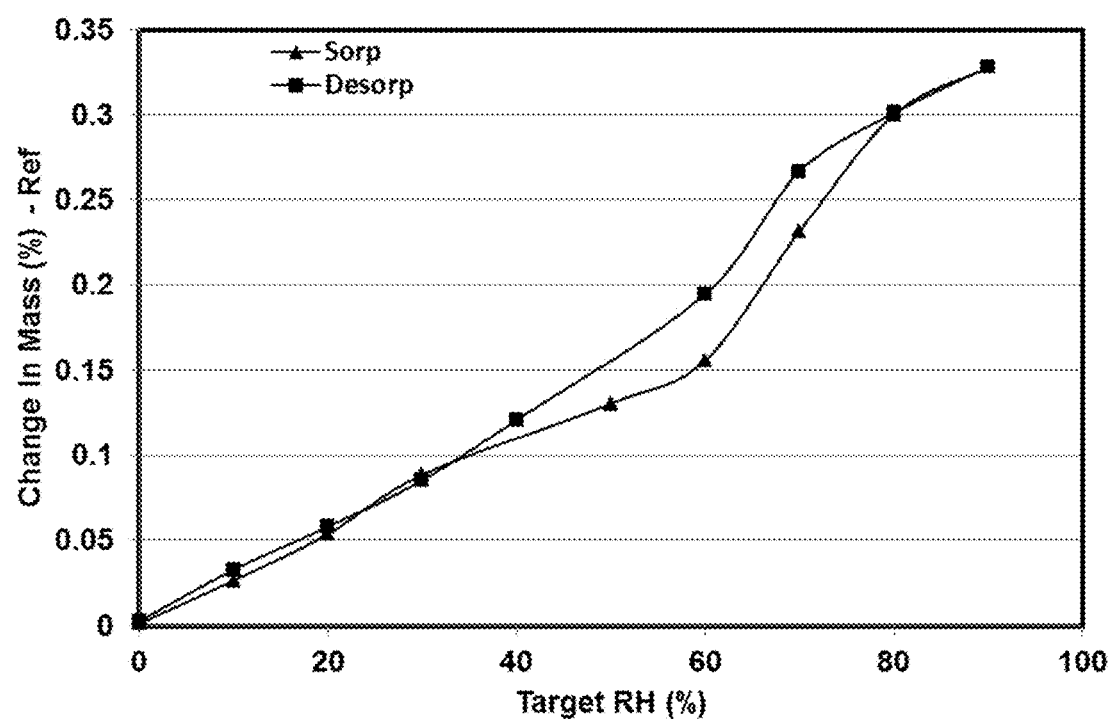
FIG. 12: DVS isotherm of the compound of Formula I Vanillate Form I

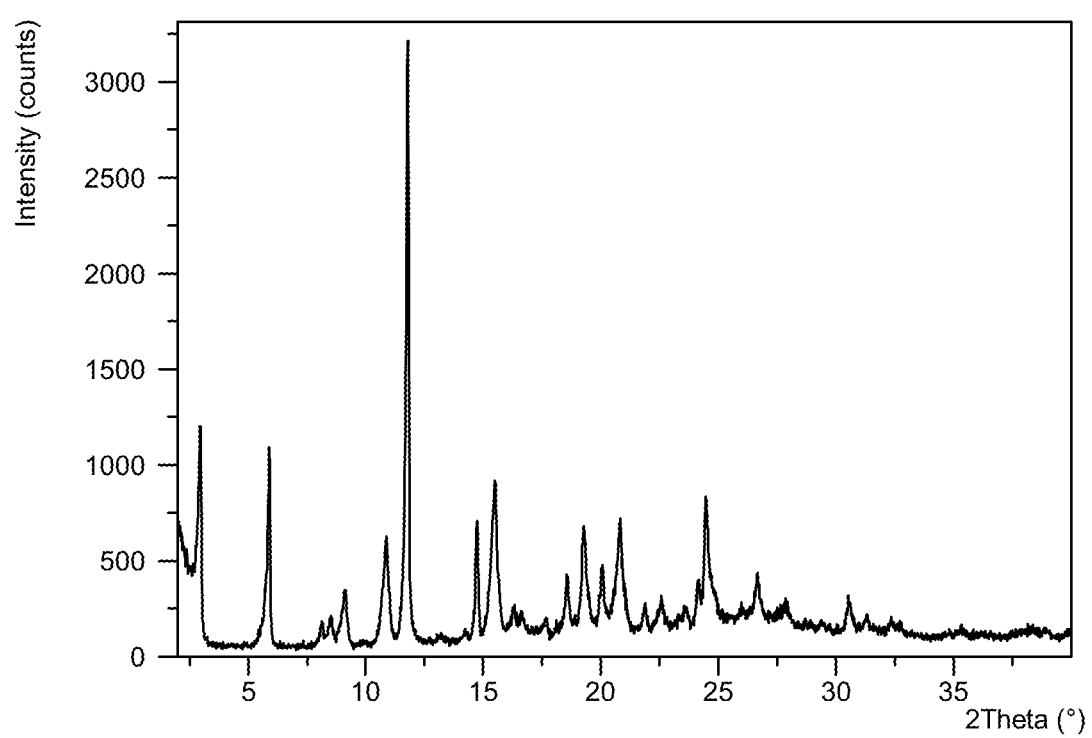
FIG. 13: XRPD pattern of the compound of Formula I Vanillate Form II

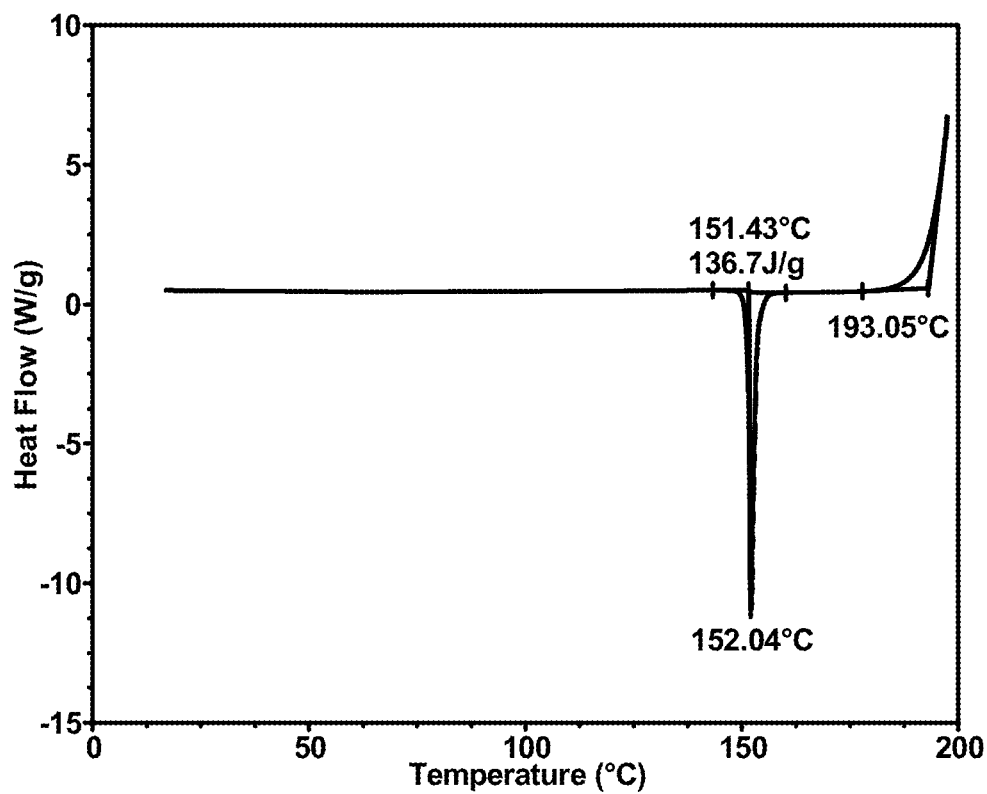
FIG. 14: DSC thermogram of the compound of Formula I Vanillate Form II

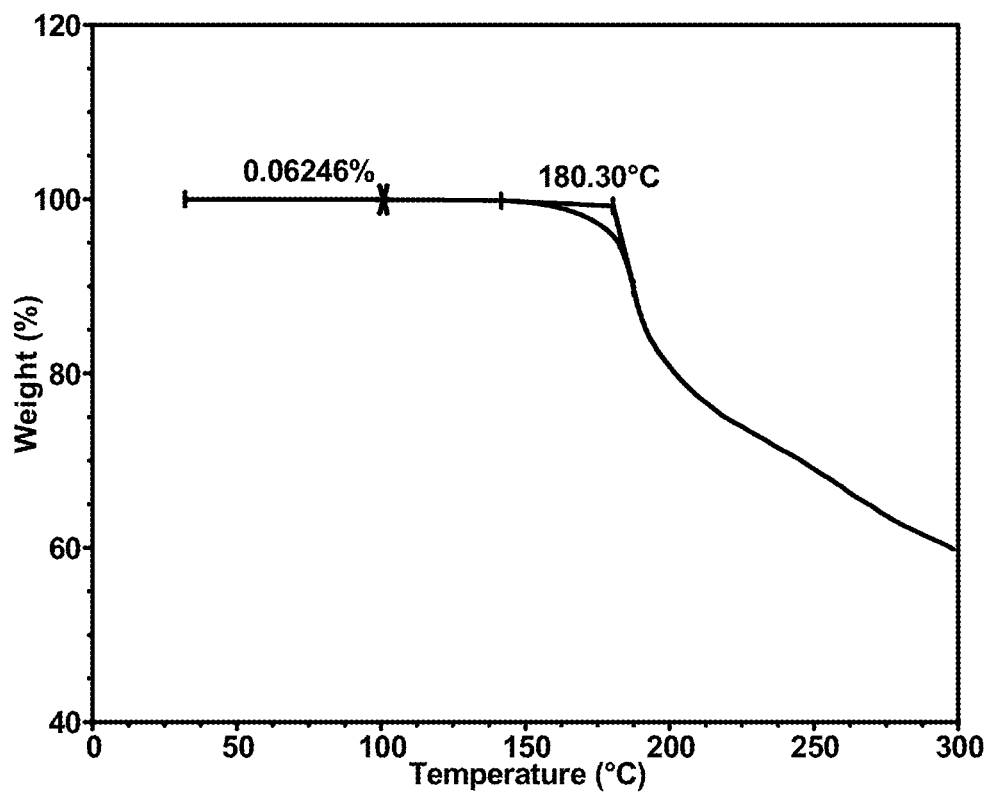
FIG. 15: TGA thermogram of the compound of Formula I Vanillate Form II

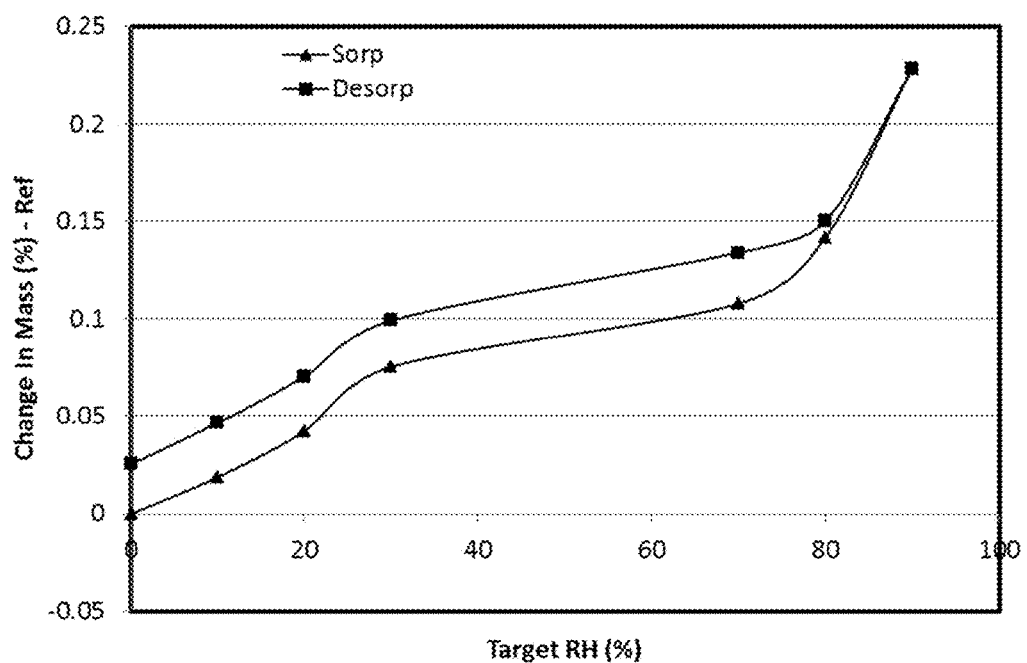
FIG. 16: DVS isotherm of the compound of Formula I Vanillate Form II

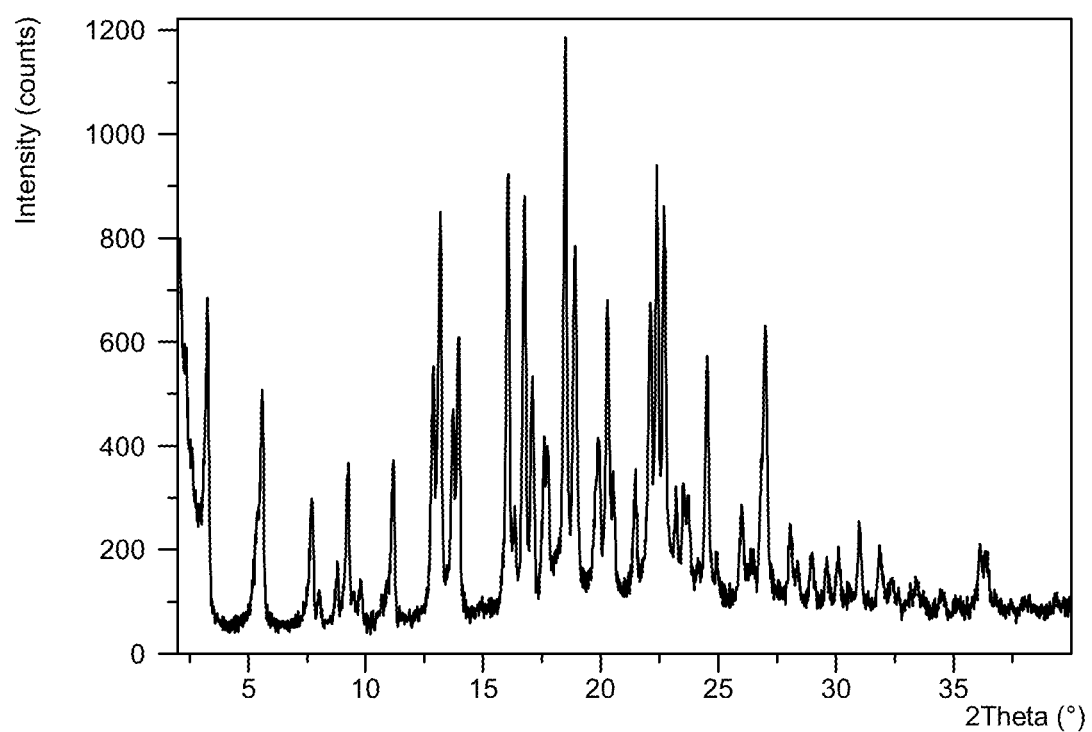
FIG. 17: XRPD pattern of the compound of Formula I Phosphate Form I

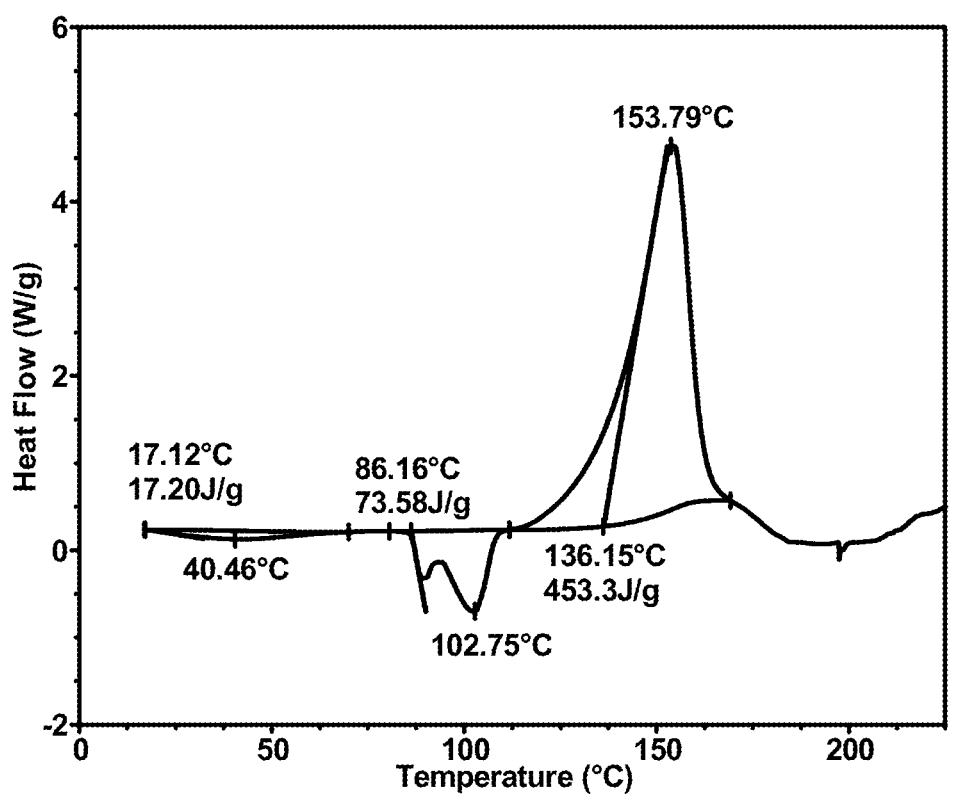
FIG. 18: DSC thermogram of the compound of Formula I Phosphate Form I

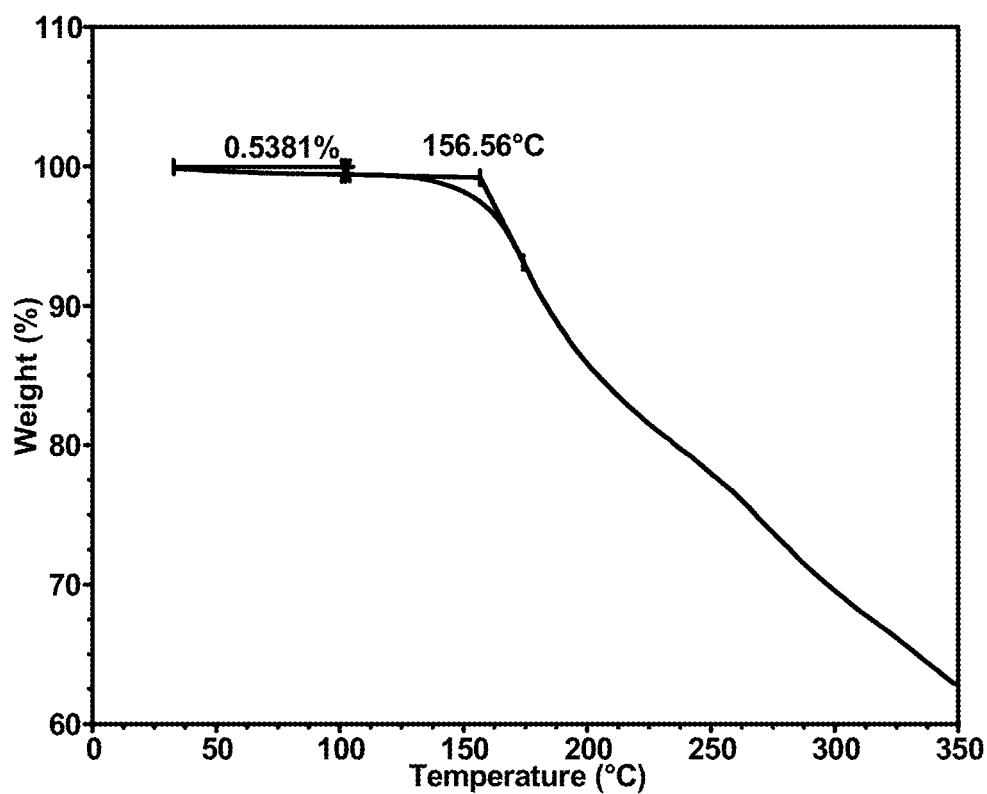
FIG. 19: TGA thermogram of the compound of Formula I Phosphate Form I

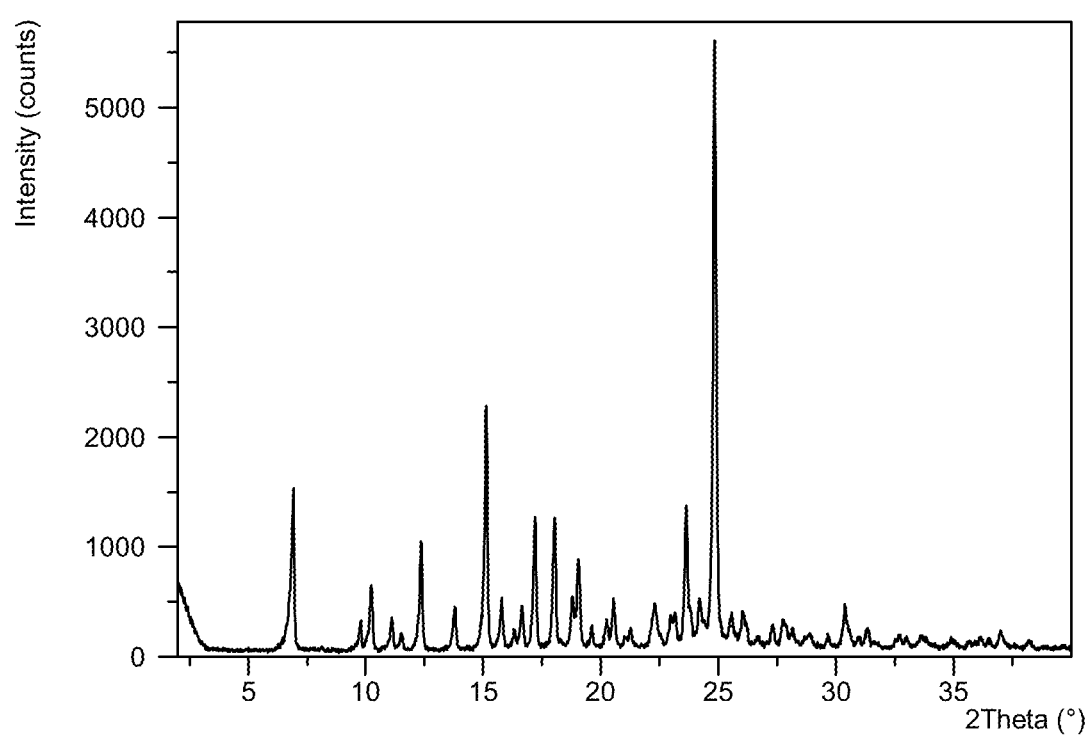
FIG. 20: XRPD pattern of the compound of Formula I Xinafoate Form I

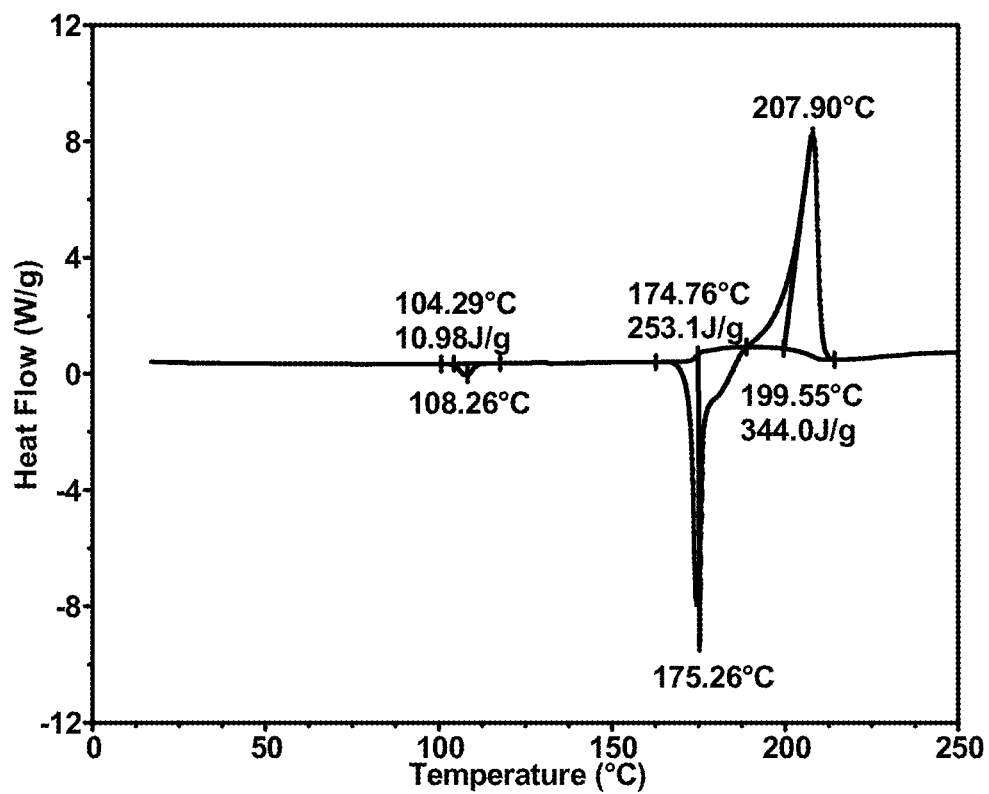
FIG. 21: DSC thermogram of the compound of Formula I Xinafoate Form I

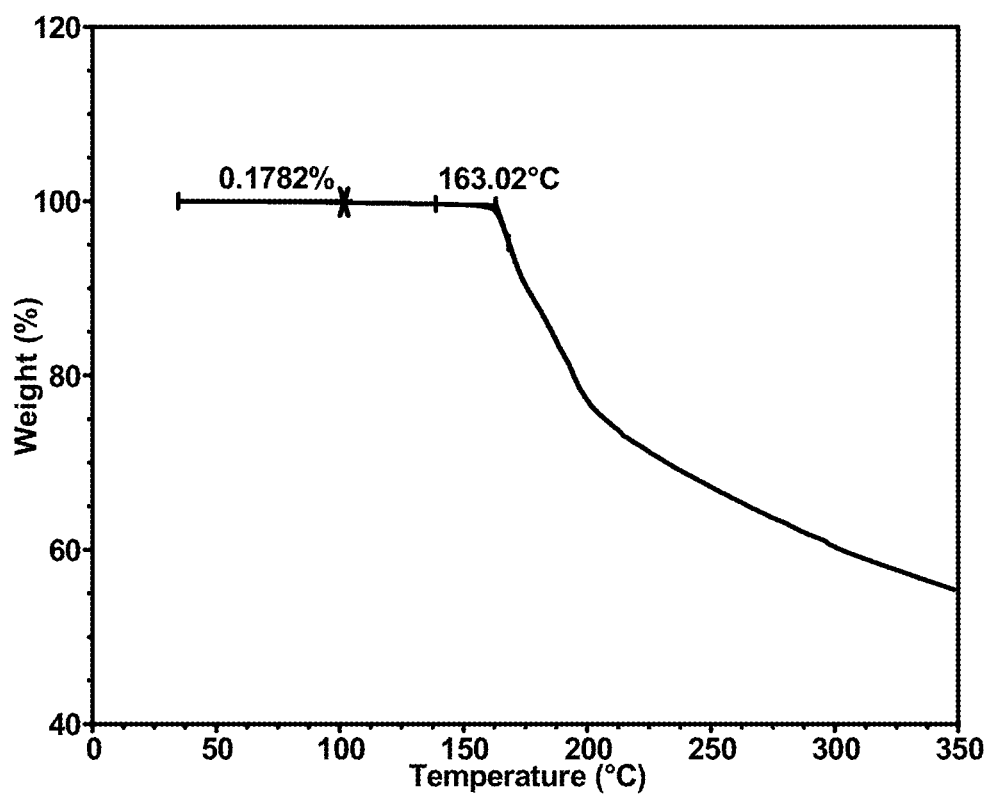
FIG. 22: TGA thermogram of the compound of Formula I Xinafoate Form I

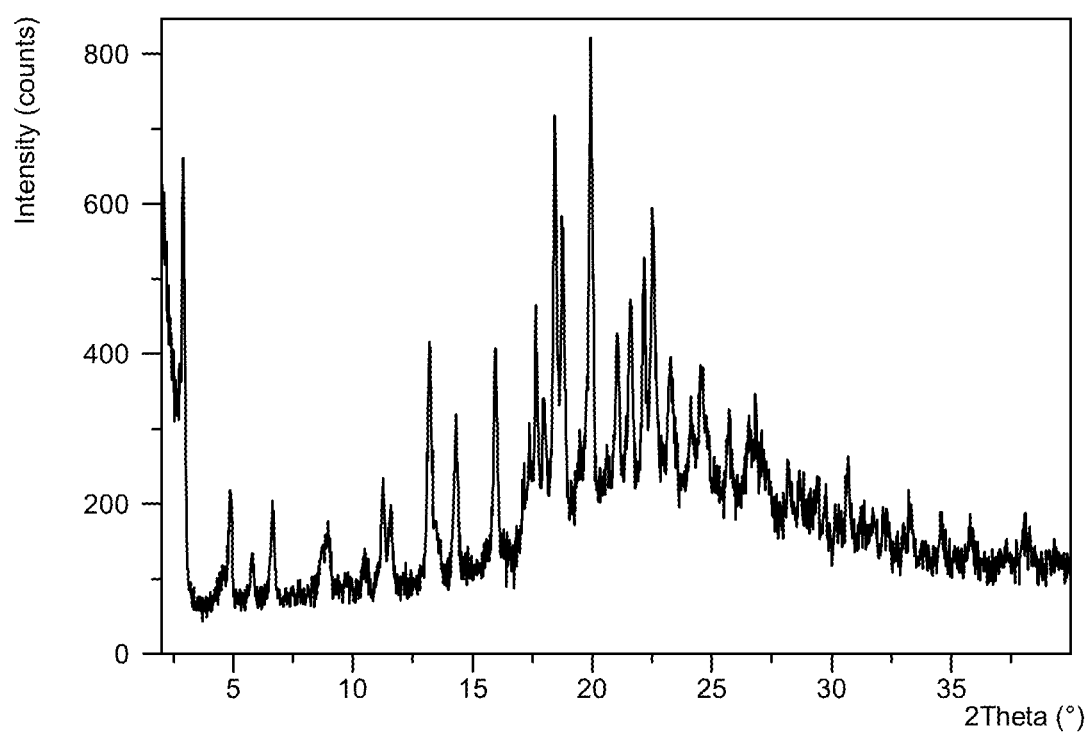
FIG. 23: XRPD pattern of the compound of Formula I Phosphate Acetonitrile Solvate Form I

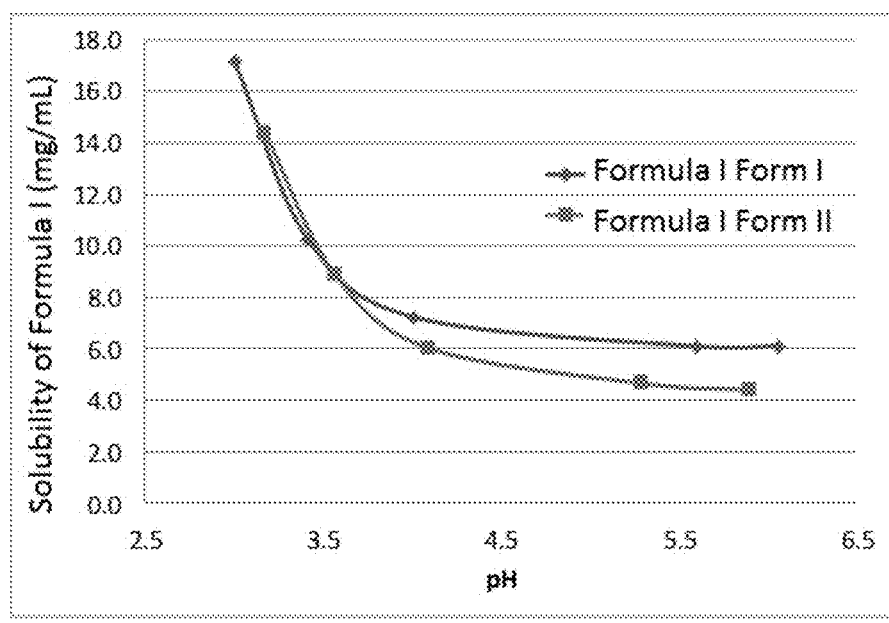
FIG. 24: pH Solubility Profile of Formula I Form I and Formula I Form II

CRYSTALLINE FORMS OF ETHYL ((S)-((((2R,5R)-5-(6-AMINO-9H-PURIN-9-YL)-4-FLUORO-2,5-DIHYDROFURAN-2-YL)OXY)METHYL)(PHENOXY)PHOSPHORYL(-L-LANINATE

CROSS REFERENCE TO RELATED APPLICATION

This application claims the benefit of U.S. provisional application 62/539,822 filed on Aug. 1, 2017. The entire contents of these applications are incorporated herein by reference in their entirety.

FIELD

The present invention relates to novel crystalline forms of ethyl ((S)-((((2R,5R)-5-(6-amino-9H-purin-9-yl)-4-fluoro-2,5-dihydrofuran-2-yl)oxy)methyl)(phenoxy)phosphoryl)-L-alaninate, and the pharmaceutical formulations, and therapeutic uses thereof.

BACKGROUND

As discussed in U.S. Pat. Nos. 7,871,991, 9,381,206, 8,951,986, and 8,658,617, ethyl ((S)-((((2R,5R)-5-(6-amino-9H-purin-9-yl)-4-fluoro-2,5-dihydrofuran-2-yl)oxy)methyl)(phenoxy)phosphoryl)-L-alaninate is a reverse transcriptase inhibitor that blocks the replication of HIV viruses, in vivo and in vitro, and has limited undesirable side effects when administered to human beings. This compound has a favorable in vitro resistance profile with activity against Nucleoside RT Inhibitor (NRTI)-Resistance Mutations, such as M184V, K65R, L74V, and one or more (e.g., 1, 2, 3, or 4) TAMs (thymidine analogue mutations). It has the following formula (see, e.g., U.S. Pat. No. 7,871,991), which is referred to as Formula I:

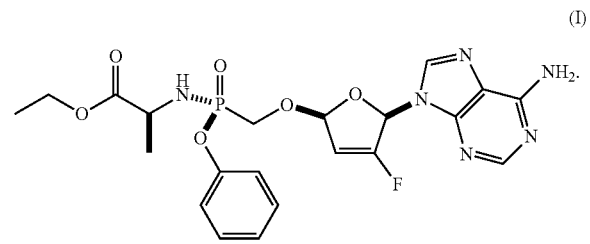

(I)

Ethyl ((S)-((((2R,5R)-5-(6-amino-9H-purin-9-yl)-4-fluoro-2,5-dihydrofuran-2-yl)oxy)methyl)(phenoxy)phosphoryl)-L-alaninate is difficult to isolate, purify, store for an extended period, and formulate as a pharmaceutical composition.

The compound of formula Ia was previously identified as the most chemically stable form of ethyl ((S)-((((2R,5R)-5-(6-amino-9H-purin-9-yl)-4-fluoro-2,5-dihydrofuran-2-yl)oxy)methyl)(phenoxy)phosphoryl)-L-alaninate. See, e.g., U.S. Pat. Nos. 8,658,617, 8,951,986, and 9,381,206. However, a total degradation increase of 2.6% was observed when the compound of formula (Ia) was stored at 25° C./60% RH over 6 months. Therefore, the compound of formula Ia requires refrigeration for long-term storage.

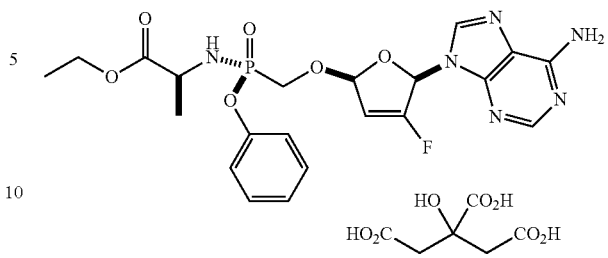

(Ia)

Accordingly, there is a need for stable forms of the compound of Formula I with suitable chemical and physical stability for the formulation, therapeutic use, manufacturing, and storage of the compound. New forms, moreover, can provide better stability for the active pharmaceutical substance in a pharmaceutical formulation.

SUMMARY

In some embodiments, the present invention is directed to novel forms of a compound of Formula I. These novel forms are useful, for example, for treating human patients infected with human immunodeficiency virus (strains of HIV-1 or HIV-2) which causes AIDS. The novel crystalline forms of the present invention are also useful, for example, for preparing a medicament for treating HIV or an HIV associated disorder. The novel forms of the present invention are also useful, for example, for inhibiting the replication of HIV viruses in vitro, and can be used, therefore, in biological assays as a control compound for identifying other reverse transcriptase inhibitors, or for investigating the mechanism of action of HIV reverse transcriptase and its inhibition.

In some embodiments, the present invention is directed to crystalline forms of ethyl ((S)-((((2R,5R)-5-(6-amino-9H-purin-9-yl)-4-fluoro-2,5-dihydrofuran-2-yl)oxy)methyl)(phenoxy)phosphoryl)-L-alaninate.

In some embodiments, the present invention is directed to ethyl ((S)-((((2R,5R)-5-(6-amino-9H-purin-9-yl)-4-fluoro-2,5-dihydrofuran-2-yl)oxy)methyl)(phenoxy)phosphoryl)-L-alaninate Form I (Formula I Form I).

In some embodiments, the present invention is directed to ethyl ((S)-((((2R,5R)-5-(6-amino-9H-purin-9-yl)-4-fluoro-2,5-dihydrofuran-2-yl)oxy)methyl)(phenoxy)phosphoryl)-L-alaninate Form II (Formula I Form II).

In some embodiments, the present invention is directed to ethyl ((S)-((((2R,5R)-5-(6-amino-9H-purin-9-yl)-4-fluoro-2,5-dihydrofuran-2-yl)oxy)methyl)(phenoxy)phosphoryl)-L-alaninate vanillate Form I (Formula I Vanillate Form I).

In some embodiments, the present invention is directed to ethyl ((S)-((((2R,5R)-5-(6-amino-9H-purin-9-yl)-4-fluoro-2,5-dihydrofuran-2-yl)oxy)methyl)(phenoxy)phosphoryl)-L-alaninate vanillate Form II (Formula I Vanillate Form II).

In some embodiments, the present invention is directed to ethyl ((S)-((((2R,5R)-5-(6-amino-9H-purin-9-yl)-4-fluoro-2,5-dihydrofuran-2-yl)oxy)methyl)(phenoxy)phosphoryl)-L-alaninate phosphate Form I (Formula I Phosphate Form I).

In some embodiments, the present invention is directed to ethyl ((S)-((((2R,5R)-5-(6-amino-9H-purin-9-yl)-4-fluoro- 2,5-dihydrofuran-2-yl)oxy)methyl)(phenoxy)phosphoryl)-L-alaninate xinafoate Form I (Formula I Xinafoate Form I).

In some embodiments, the present invention is directed to ethyl ((S)-((((2R,5R)-5-(6-amino-9H-purin-9-yl)-4-fluoro-2,5-dihydrofuran-2-yl)oxy)methyl)(phenoxy)phosphoryl)-L-alaninate phosphate acetonitrile solvate Form I (Formula I Phosphate Acetonitrile Solvate Form I).

In some embodiments, the present invention is directed to methods of treating an HIV infection by administering to a subject in need thereof a therapeutically effective amount of a compound (e.g., a compound of Formula I) provided herein.

In some embodiments, the present invention is directed to a compound (e.g., a compound of Formula I) provided herein for use in methods of treating an HIV infection.

In some embodiments, the present invention is directed to the use of a compound (e.g., a compound of Formula I) provided herein in the manufacture of a medicament for treating an HIV infection.

In some embodiments, disclosed herein are compositions and oral dosage forms (e.g., tablets) comprising a novel crystalline forms of ethyl ((S)-((((2R,5R)-5-(6-amino-9H-purin-9-yl)-4-fluoro-2,5-dihydrofuran-2-yl)oxy)methyl)(phenoxy)phosphoryl)-L-alaninate (e.g., a compound of Formula I Form I and/or Formula I Form II) and at least one additional therapeutic agent.

In some embodiments, disclosed herein are compositions and oral dosage forms (e.g., tablets) comprising:

(i) a novel crystalline forms of ethyl ((S)-((((2R,5R)-5-(6-amino-9H-purin-9-yl)-4-fluoro-2,5-dihydrofuran-2-yl)oxy)methyl)(phenoxy)phosphoryl)-L-alaninate (e.g., a compound of Formula I Form I and/or Formula I Form II)

(ii) a compound of Formula II

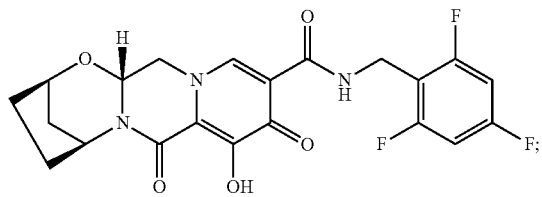

(III)

(iii) a compound of Formula III

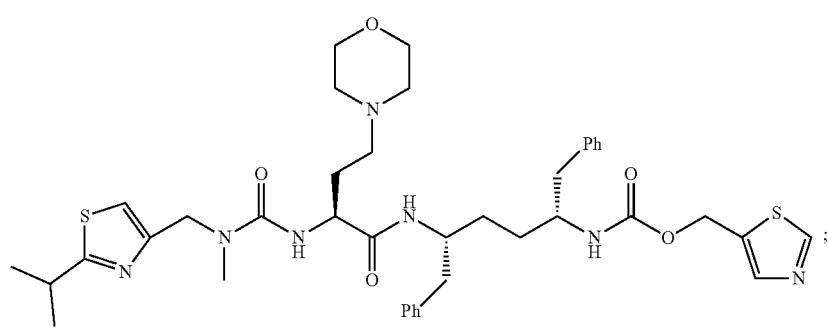

and (iv) a compound of Formula IV

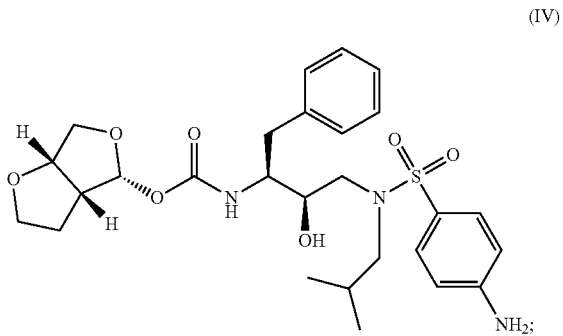 [SMILES: CC(C)CN(C[C@@H](O)[C@H](Cc1ccccc1)NC(=O)O[C@H]1OC[C@H]2OCC[C@@H]12)S(=O)(=O)c1ccc(N)cc1]

(IV)

or any pharmaceutically acceptable salt, co-crystal, or solvate of the foregoing.

The compositions and oral dosage forms herein include a compound of Formula I, ethyl ((S)-((((2R,5R)-5-(6-amino-9H-purin-9-yl)-4-fluoro-2,5-dihydrofuran-2-yl)oxy)methyl)(phenoxy)phosphoryl)-L-alaninate, having the following structure:

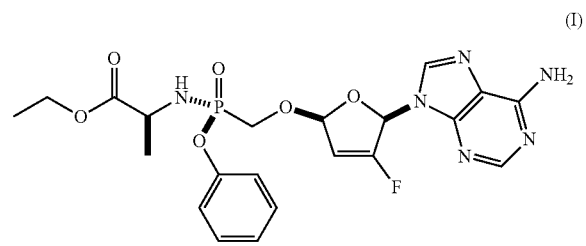

(I)

or a pharmaceutically acceptable salt, co-crystal, or solvate thereof.

In some embodiments, the compound of Formula I is Formula I Form I. In some embodiments, the compound of Formula I is Formula I Form II.

In some embodiments, the compound of Formula I is the vanillate (i.e., Formula Ib), having the following structure:

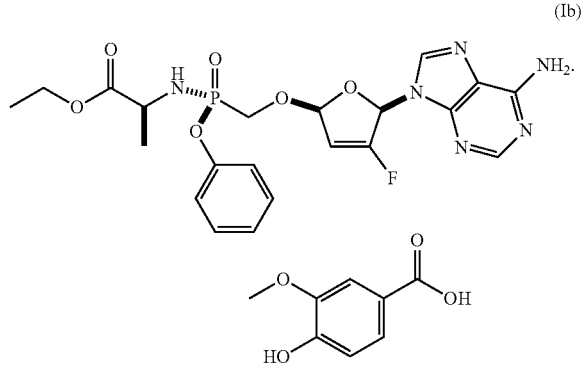

(Ib)

In some embodiments, Formula (Ib) is Formula I Vanillate Form I. In some embodiments, Formula (Ib) is Formula I Vanillate Form II.

In some embodiments, the compound of Formula I is the phosphate (i.e., Formula Ic), having the following structure:

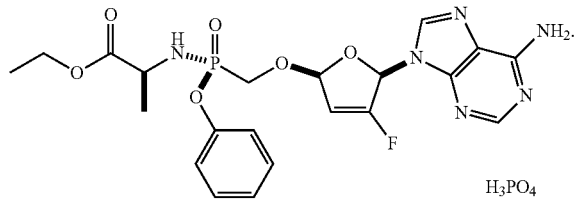

(Ic)

In some embodiments, Formula (Ic) is Formula I Phosphate Form I.

In some embodiments, the compound of Formula I is the xinafoate (i.e., Formula Id), having the following structure:

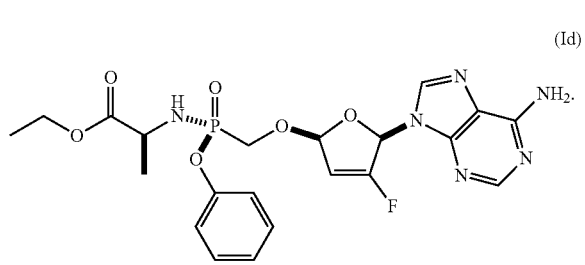

(Id)

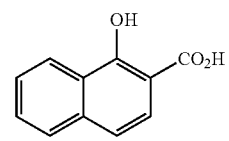

In some embodiments, Formula (Id) is Formula I Xinafoate Form I.

In some embodiments, the novel crystalline form of ethyl ((S)-((((2R,5R)-5-(6-amino-9H-purin-9-yl)-4-fluoro-2,5-dihydrofuran-2-yl)oxy)methyl)(phenoxy)phosphoryl)-L-alaninate is a solvate. In some embodiments, the solvate is ethyl ((S)-((((2R,5R)-5-(6-amino-9H-purin-9-yl)-4-fluoro-2,5-dihydrofuran-2-yl)oxy)methyl)(phenoxy)phosphoryl)-L-alaninate phosphate acetonitrile solvate Form I (i.e., Formula I Phosphate Acetonitrile Solvate Form I).

In some embodiments, the compositions and oral dosage forms herein include a compound of Formula II, (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide (bictegravir), having the following structure:

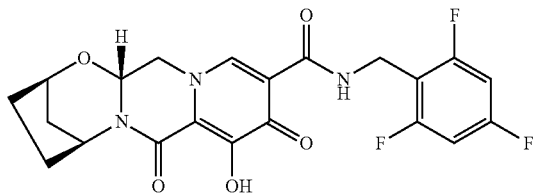

(II)

or a pharmaceutically acceptable salt, co-crystal, or solvate thereof.

In some embodiments, the pharmaceutically acceptable salt is a compound of Formula IIa, sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate, having the following structure:

(IIa)

In some embodiments, the compositions and oral dosage forms herein include a compound of Formula III, 1,3-thiazol-5-ylmethyl[(2R,5R)-5-{[(2S)2-[(methyl {[2-(propan-2-yl)-1,3-thiazol-4-yl]methyl}carbamoyl)amino]-4-(morpholin-4-yl)butanoyl]amino}-1,6-diphenylhexan-2-yl]carbamate (cobicistat), having the following structure:

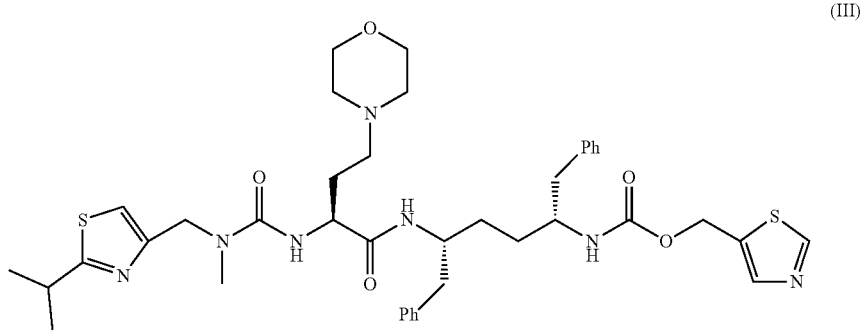 [SMILES: CC(C)c1nc(CN(C)C(=O)N[C@@H](CCN2CCOCC2)C(=O)N[C@H](CC[C@H](Cc2ccccc2)NC(=O)OCc2cncs2)Cc2ccccc2)cs1]

(III)

or a pharmaceutically acceptable salt, co-crystal, or solvate thereof.

In some embodiments, the compositions and oral dosage forms herein include a compound of Formula IV, [(1S,2R)-3-[[(4-aminophenyl)sulfonyl](2-methylpropyl)amino]-2-hydroxy-1-(phenylmethyl)propyl]-carbamic acid (3R,3aS,6aR)-hexahydrofuro[2,3-b]furan-3-yl ester (darunavir), having the following structure:

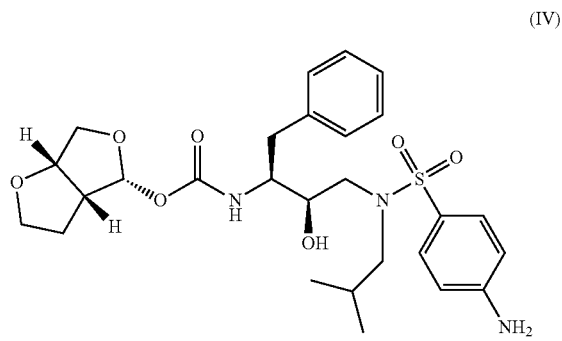 [SMILES: CC(C)CN(C[C@@H](O)[C@H](Cc1ccccc1)NC(=O)O[C@H]1OC[C@H]2OCC[C@@H]12)S(=O)(=O)c1ccc(N)cc1]

(IV)

or a pharmaceutically acceptable salt, co-crystal, or solvate thereof.

In some embodiments, the solvate is a compound of Formula IVa, [(1S,2R)-3-[[(4-aminophenyl)sulfonyl](2-methylpropyl)amino]-2-hydroxy-1-(phenylmethyl)propyl]-carbamic acid (3R,3aS,6aR)-hexahydrofuro[2,3-b]furan-3-yl ester monoethanolate, having the following structure:

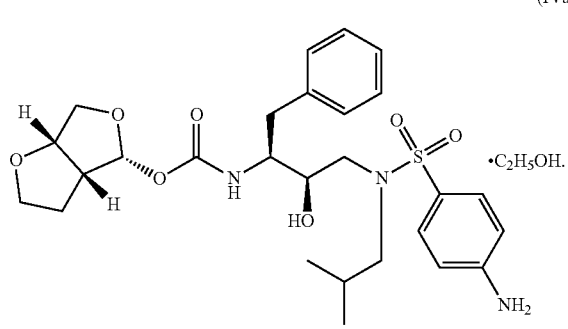

(IVa)

In some embodiments, a solid oral dosage form comprising: (a) the compound of Formula I or a pharmaceutically acceptable salt, co-crystal, or solvate thereof, (b) the compound of Formula II or a pharmaceutically acceptable salt, co-crystal, or solvate thereof, (c) the compound of Formula III or a pharmaceutically acceptable salt, co-crystal, or solvate thereof, and (d) the compound of Formula IV or a pharmaceutically acceptable salt, co-crystal, or solvate thereof, is provided.

The inventors have found that the use of a fixed dose combination may assist in achieving appropriate pharmacokinetic parameters and/or adequate tablet stability. In addition, the use of a single-layer and/or multilayer tablet as a particular type of fixed-dose combination may also provide pharmacokinetic and/or stability benefits. Accordingly, in another aspect a fixed dose combination tablet comprising (a) the compound of Formula I, or a pharmaceutically acceptable salt, co-crystal, or solvate thereof, (b) the compound of Formula II, or a pharmaceutically acceptable salt, co-crystal, or solvate thereof, (c) cobicistat, or a pharmaceutically acceptable salt, co-crystal, or solvate thereof, and (d) darunavir, or a pharmaceutically acceptable salt, co-crystal, or solvate thereof is provided. Additionally, a multilayer tablet comprising (a) the compound of Formula I, or a pharmaceutically acceptable salt, co-crystal, or solvate thereof, (b) the compound of Formula II, or a pharmaceutically acceptable salt, co-crystal, or solvate thereof, (c) cobicistat, or a pharmaceutically acceptable salt, co-crystal, or solvate thereof, and (d) darunavir, or a pharmaceutically acceptable salt, co-crystal, or solvate thereof is provided. In some embodiments, cobicistat, or a pharmaceutically acceptable salt, co-crystal, or solvate thereof, is amorphous. In some embodiments, cobicistat, or a pharmaceutically acceptable salt, co-crystal, or solvate thereof, is crystalline.

In some embodiments, cobicistat, or a pharmaceutically acceptable salt, co-crystal, or solvate thereof, is adsorbed onto silicon dioxide particles (e.g., fumed silicon dioxide). In some embodiments, up to about 60%±10% (w/w) of cobicistat, or a pharmaceutically acceptable salt, co-crystal, or solvate thereof, can typically be loaded onto the silicon dioxide particles. In some embodiments, the weight percentage of the cobicistat, or a pharmaceutically acceptable salt, co-crystal, or solvate thereof, to the silicon dioxide particles is 20-30%±15%. In some embodiments, the weight percentage of the cobicistat, or a pharmaceutically acceptable salt, co-crystal, or solvate thereof, to the silicon dioxide particles is 45-50%±15%. In some embodiments, the weight percentage of the cobicistat, or a pharmaceutically acceptable salt, co-crystal, or solvate thereof, to the silicon dioxide particles is 47-56%±10%. In some embodiments, the (weight of the cobicistat, or a pharmaceutically acceptable salt, co-crystal, or solvate thereof) divided by the (weight of the silicon dioxide particles) in a composition is from about 0.2 to about 1.9. In some embodiments, the (weight of the cobicistat, or a pharmaceutically acceptable salt, co-crystal, or solvate thereof) divided by the (weight of the silicon dioxide particles) in a composition is from about 0.5 to about 1.5. In some embodiments, the (weight of the cobicistat, or a pharmaceutically acceptable salt, co-crystal, or solvate thereof) divided by the (weight of the silicon dioxide particles) in a composition is from about 0.8 to about 1.2. In some embodiments, the (weight of the cobicistat, or a pharmaceutically acceptable salt, co-crystal, or solvate thereof) divided by the (weight of the silicon dioxide particles) in a composition is about 1.0±0.5%.

In some embodiments, a kit comprising: (i) a tablet comprising a compound of Formula I (or a pharmaceutically acceptable salt, co-crystal, or solvate thereof), a compound of Formula II (or a pharmaceutically acceptable salt, co-crystal, or solvate thereof), cobicistat (or a pharmaceutically acceptable salt, co-crystal, or solvate thereof), and darunavir (or a pharmaceutically acceptable salt, co-crystal, or solvate thereof); and (ii) a desiccant (e.g. silica gel) is provided.

The solid oral dosage form disclosed herein is suitable for use in medicine, and in particular in treating or preventing viral infections such as HIV.

DESCRIPTION OF THE FIGURES

FIG. 1 shows an XRPD pattern of the compound of Formula I Form I.

FIG. 2 shows a DSC thermogram of the compound of Formula I Form I.

FIG. 3 shows a TGA thermogram of the compound of Formula I Form I.

FIG. 4 shows a DVS isotherm of the compound of Formula I Form I.

FIG. 5 shows an XRPD pattern of the compound of Formula I Form II.

FIG. 6 shows a DSC thermogram of the compound of Formula I Form II.

FIG. 7 shows a TGA thermogram of the compound of Formula I Form II.

FIG. 8 shows a DVS isotherm of the compound of Formula I Form II.

FIG. 9 shows an XRPD pattern of the compound of Formula I Vanillate Form I.

FIG. 10 shows a DSC thermogram of the compound of Formula I Vanillate Form I.

FIG. 11 shows a TGA thermogram of the compound of Formula I Vanillate Form I.

FIG. 12 shows a DVS isotherm of the compound of Formula I Vanillate Form I.

FIG. 13 shows an XRPD pattern of the compound of Formula I Vanillate Form II.

FIG. 14 shows a DSC thermogram of the compound of Formula I Vanillate Form II.

FIG. 15 shows a TGA thermogram of the compound of Formula I Vanillate Form II.

FIG. 16 shows a DVS isotherm of the compound of Formula I Vanillate Form II.

FIG. 17 shows an XRPD pattern of the compound of Formula I Phosphate Form I.

FIG. 18 shows a DSC thermogram of the compound of Formula I Phosphate Form I.

FIG. 19 shows a TGA thermogram of the compound of Formula I Phosphate Form I.

FIG. 20 shows an XRPD pattern of the compound of Formula I Xinafoate Form I.

FIG. 21 shows a DSC thermogram of the compound of Formula I Xinafoate Form I.

FIG. 22 shows a TGA thermogram of the compound of Formula I Xinafoate Form I.

FIG. 23 shows an XRPD pattern of the compound of Formula I Phosphate Acetonitrile Solvate Form I.

FIG. 24: shows the solubility profile of Formula I Form I and Formula I Form II.

DETAILED DESCRIPTION

Figure 25A:
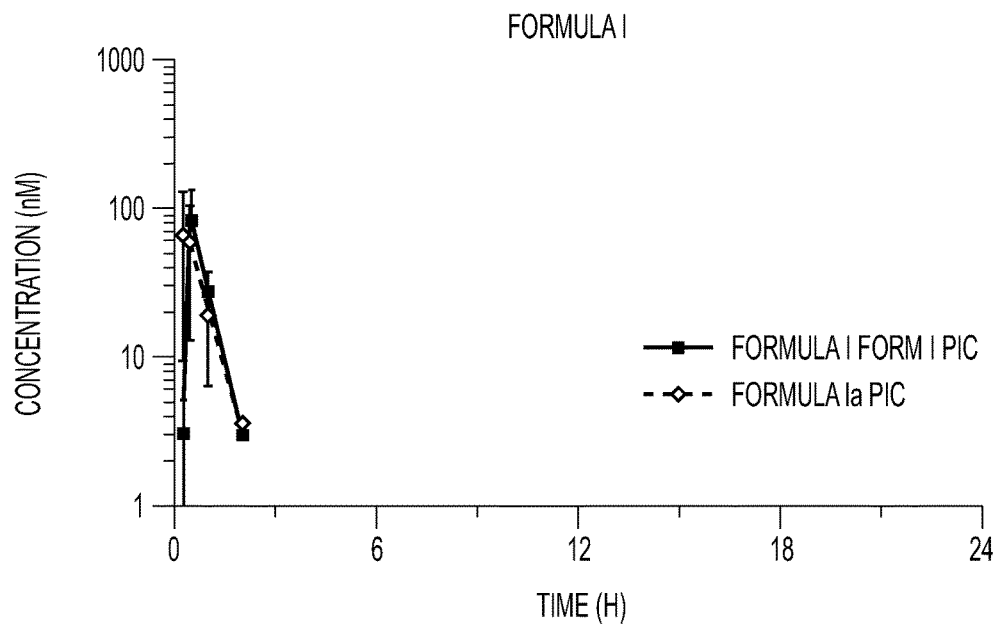
FIGS. 25A-B: show exposure studies of Formula I Form I and the Compound of Formula Ia in fasted dogs (n=4) that were pre-treated with pentagastrin.

In the following description, certain specific details are set forth in order to provide a thorough understanding of various embodiments of the invention. However, one skilled in the art will understand that the invention may be practiced without these details. The description below of several embodiments is made with the understanding that the present disclosure is to be considered as an exemplification of the claimed subject matter, and is not intended to limit the appended claims to the specific embodiments illustrated. The headings used throughout this disclosure are provided for convenience only and are not to be construed to limit the claims in any way. Embodiments illustrated under any heading may be combined with embodiments illustrated under any other heading.

Definitions

Unless the context requires otherwise, throughout the present specification and claims, the word "comprise" and variations thereof, such as, "comprises" and "comprising" are to be construed in an open, inclusive sense, that is as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Embodiments that reference throughout this specification to "a compound" include the crystalline, salt, co-crystal, and solvate forms of the formulas and/or compounds disclosed herein. Thus, the appearance or the phrase "a compound of Formula I" comprises Formula I Form I; Formula I Form II; Formula I Vanillate Form I; Formula I Vanillate Form II; Formula I Phosphate Form I; Formula I Xinafoate Form I; and Formula I Phosphate Acetonitrile Solvate Form I.

The invention disclosed herein is also meant to encompass all pharmaceutically acceptable compounds of Formula I being isotopically-labeled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These radiolabeled compounds could be useful to help determine or measure the effectiveness of the compounds, by characterizing, for example, the site or mode of action, or binding affinity to pharmacologically important site of action. Certain isotopically-labeled compounds of Formula I, for example, those incorporating a radioactive isotope, are useful in drug and/or substrate tissue distribution studies. The radioactive isotopes tritium, i.e. $^3$H, and carbon-14, i.e., $^{14}$C, are particularly useful for this purpose in view of their ease of incorporation and ready means of detection.

Substitution with heavier isotopes such as deuterium, i.e., $^2$H, may afford certain therapeutic advantages resulting from greater metabolic stability. For example, in vivo half-life may increase or dosage requirements may be reduced. Thus, heavier isotopes may be preferred in some circumstances.

Substitution with positron emitting isotopes, such as $^{11}$C, $^{18}$F, 15O and $^{13}$N, can be useful in Positron Emission Topography (PET) studies for examining substrate receptor occupancy. Isotopically-labeled compounds of Formula I can generally be prepared by conventional techniques known to those skilled in the art or by processes analogous to those described in the Examples as set out below using an appropriate isotopically-labeled reagent in place of the non-labeled reagent previously employed.

"Stable compound" and "stable structure" are meant to indicate a compound that is sufficiently robust to survive isolation to a useful degree of purity from a reaction mixture, and formulation into an efficacious therapeutic agent.

"Optional" or "optionally" means that the subsequently described event or circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, and/or emulsifier, or a combination of one or more of the above which has been approved by the United States Food and Drug Administration as being acceptable for use in humans or domestic animals.

A "pharmaceutical composition" refers to a formulation of a compound of the invention (e.g., a compound of Formula I) and a medium generally accepted in the art for the delivery of the biologically active compound to mammals, e.g., humans. Such a medium includes all pharmaceutically acceptable excipients therefor.

"Effective amount" or "therapeutically effective amount" refers to an amount of a compound according to the invention, which when administered to a patient in need thereof, is sufficient to effect treatment for disease-states, conditions, or disorders for which the compounds have utility. Such an amount would be sufficient to elicit the biological or medical response of a tissue system, or patient that is sought by a researcher or clinician. The amount of a compound according to the invention which constitutes a therapeutically effective amount will vary depending on such factors as the compound and its biological activity, the composition used for administration, the time of administration, the route of administration, the rate of excretion of the compound, the duration of the treatment, the type of disease-state or disorder being treated and its severity, drugs used in combination with or coincidentally with the compounds of the invention, and the age, body weight, general health, sex and diet of the patient. Such a therapeutically effective amount can be determined routinely by one of ordinary skill in the art having regard to their own knowledge, the state of the art, and this disclosure.

"Treating" and "treatment" of a disease include the following:

(1) preventing or reducing the risk of developing the disease, i.e., causing the clinical symptoms of the disease not to develop in a subject that may be exposed to or predisposed to the disease but does not yet experience or display symptoms of the disease, (2) inhibiting the disease, i.e., arresting or reducing the development of the disease or its clinical symptoms, and (3) relieving the disease, i.e., causing regression of the disease or its clinical symptoms.

The terms "subject" or "patient" refer to an animal, such as a mammal (including a human), that has been or will be the object of treatment, observation or experiment. The methods described herein may be useful in human therapy and/or veterinary applications. In some embodiments, the subject is a mammal (or the patient). In some embodiments the subject (or the patient) is human, domestic animals (e.g., dogs and cats), farm animals (e.g., cattle, horses, sheep, goats and pigs), and/or laboratory animals (e.g., mice, rats, hamsters, guinea pigs, pigs, rabbits, dogs, and monkeys). In some embodiments, the subject (or the patient) is a human. "Human (or patient) in need thereof" refers to a human who may have or is suspect to have diseases or conditions that would benefit from certain treatment; for example, being treated with the compounds disclosed herein according to the present application.

The term "antiviral agent" as used herein is intended to mean an agent (compound or biological) that is effective to inhibit the formation and/or replication of a virus in a human being, including but not limited to agents that interfere with either host or viral mechanisms necessary for the formation and/or replication of a virus in a human being.

The term "inhibitor of HIV replication" as used herein is intended to mean an agent capable of reducing or eliminating the ability of HIV to replicate in a host cell, whether in vitro, ex vivo or in vivo.

Reference to "about" a value or parameter herein includes (and describes) embodiments that are directed to that value or parameter per se. For example, description referring to "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Pharmaceutically acceptable" or "physiologically acceptable" refer to compounds, salts, compositions, dosage forms and other materials which are useful in preparing a pharmaceutical composition that is suitable for veterinary or human pharmaceutical use.

"Unit dosage forms" are physically discrete units suitable as unitary dosages for subjects (e.g., human subjects and other mammals), each unit containing a predetermined quantity of active material calculated to produce the desired therapeutic effect, in association with a suitable pharmaceutical excipient.

The term "substantially as shown in" when referring, for example, to an XRPD pattern, a DSC thermogram, a DVS isotherm, or a TGA thermogram includes a pattern, thermogram or spectrum that is not necessarily identical to those depicted herein, but that falls within the limits of experimental error or deviations when considered by one of ordinary skill in the art.

In some embodiments, the term "substantially pure" or "substantially free" with respect to a particular crystalline form of a compound means that the composition comprising the crystalline form contains less than 99%, less than 95%, less than 90%, less than 85%, less than 80%, less than 75%, less than 70%, less than 65%, less than 60%, less than 55%, less than 50%, less than 40%, less than 30%, less than 20%, less than 15%, less than 10%, less than 5%, or less than 1% by weight of other substances, including other crystalline forms and/or impurities. In certain embodiments, "substantially pure" or "substantially free of" refers to a substance free of other substances, including other crystalline forms and/or impurities. Impurities may, for example, include by-products or left over reagents from chemical reactions, contaminants, degradation products, other crystalline forms, water, and solvents.

Crystalline Forms of Formula I

The compound of formula Ia was previously identified as the most chemically stable form of ethyl ((S)-((((2R,5R)-5-(6-amino-9H-purin-9-yl)-4-fluoro-2,5-dihydrofuran-2-yl)oxy)methyl)(phenoxy)phosphoryl)-L-alaninate. See, e.g., U.S. Pat. Nos. 8,658,617, 8,951,986, and 9,381,206. However, a total degradation increase of 2.6% was observed when the compound of formula (Ia) was stored at 25° C./60% RH over 6 months. Therefore, the compound of formula Ia requires refrigeration for long-term storage.

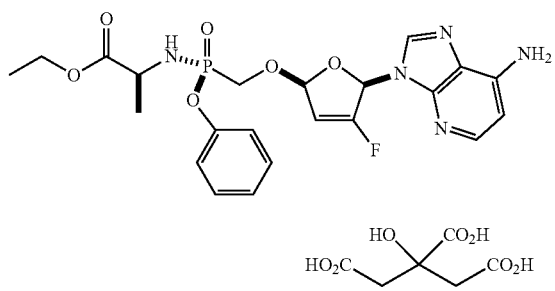

(Ia)

Accordingly, there is a need for stable forms of the compound of Formula I with suitable chemical and physical stability for the formulation, therapeutic use, manufacturing, and storage of the compound.

Moreover, it is desirable to develop a crystalline form of Formula I that may be useful in the synthesis of Formula I. A crystalline form of a Formula I may be an intermediate to the synthesis of Formula I. A crystalline form may have properties such as bioavailability, stability, purity, and/or manufacturability at certain conditions that may be suitable for medical or pharmaceutical uses.

Crystalline forms of Formula I, including substantially pure forms, may provide the advantage of bioavailability and stability, suitable for use as an active ingredient in a pharmaceutical composition. Variations in the crystal structure of a pharmaceutical drug substance or active ingredient may affect the dissolution rate (which may affect bioavailability, etc.), manufacturability (e.g., ease of handling, ability to consistently prepare doses of known strength), and stability (e.g., thermal stability, shelf life, etc.) of a pharmaceutical drug product or active ingredient. Such variations may affect the preparation or formulation of pharmaceutical compositions in different dosage or delivery forms, such as solutions or solid oral dosage form including tablets and capsules. Compared to other forms such as non-crystalline or amorphous forms, crystalline forms may provide desired or suitable hygroscopicity, particle size controls, dissolution rate, solubility, purity, physical and chemical stability, manufacturability, yield, and/or process control. Thus, crystalline forms of the compound of Formula I may provide advantages such as improving: the manufacturing process of the compound, the stability or storability of a drug product form of the compound, the stability or storability of a drug substance of the compound and/or the bioavailability and/or stability of the compound as an active agent.

The use of certain solvents and/or processes have been found to produce different crystalline forms of the compound Formula I described herein which may exhibit one or more favorable characteristics described above. The processes for the preparation of the crystalline forms described herein and characterization of these crystalline forms are described in detail below.

One skilled in the art understands that a compound structure may be named or identified using commonly recognized nomenclature systems and symbols. By way of example, the compound may be named or identified with common names, systematic or non-systematic names. The nomenclature systems and symbols that are commonly recognized in the art of chemistry including but not limited to Chemical Abstract Service (CAS) and International Union of Pure and Applied Chemistry (IUPAC). Accordingly, the structure of the compound of formula I provided above may also be named or identified as ethyl ((S)-((((2R,5R)-5-(6-amino-9H-purin-9-yl)-4-fluoro-2,5-dihydrofuran-2-yl)oxy)methyl)(phenoxy)phosphoryl)-L-alaninate under IUPAC and as N—[(S)-[[[(2R,5R)-5-(6-amino-9H-purin-9-yl)-4-fluoro-2,5-dihydro-2-furanyl]oxy]methyl]phenoxyphosphinyl]-, ethyl ester under CAS; CAS Registry Number 912809-27-9.

In particular embodiments, novel crystalline forms of Formula I are disclosed.

Formula I Form I

In some embodiments, provided herein is a crystalline compound of Formula I (crystalline Formula I Form I), wherein the crystal structure exhibits an X-ray powder diffraction (XRPD) pattern substantially as shown in FIG. 1. Crystalline Formula I Form I may exhibit a differential scanning calorimetry (DSC) thermogram substantially as shown in FIG. 2. Crystalline Formula I Form I may exhibit a thermogravimetric analysis (TGA) thermogram substantially as shown in FIG. 3. Crystalline Formula I Form I may exhibit a dynamic vapor sorption (DVS) isotherm substantially as shown in FIG. 4.

In some embodiments of crystalline Formula I Form I, at least one, at least two, at least three, or all of the following (a)-(d) apply: (a) crystalline Formula I Form I has an XRPD pattern substantially as shown in FIG. 1; (b) crystalline Formula I Form I has a DSC thermogram substantially as shown in FIG. 2; (c) crystalline Formula I Form I has a TGA thermogram substantially as shown in FIG. 3; (d) crystalline Formula I Form I has a DVS isotherm substantially as shown in FIG. 4.

In some embodiments, crystalline Formula I Form I has at least one, at least two, at least three, or at least four of the following properties:
(a) an XRPD pattern substantially as shown in FIG. 1
(b) a DSC thermogram substantially as shown in FIG. 2
(c) a TGA thermogram substantially as shown in FIG. 3
(d) a DVS isotherm substantially as shown in FIG. 4

In some embodiments, crystalline Formula I Form I has an XRPD pattern displaying at least two, at least three, at least four, at least five, at least six, at least seven, at least eight, or at least nine of the degree 2θ-reflections with the greatest intensity as the XRPD pattern substantially as shown in FIG. 1.

In certain embodiments, crystalline Formula I Form I has an XRPD pattern comprising degree 2θ-reflections (±0.2 degrees 2θ) at 7.70, 11.2°, and 15.2°. In some embodiments, crystalline Formula I Form I has an XRPD pattern comprising degree 2θ-reflections (±0.2 degrees 2θ) at 7.70, 11.2°, and 15.2° and one, two or three of the degree 2θ-reflections (±0.2 degrees 2θ) at 18.50, 20.3°, and 21.4°. In some embodiments, crystalline Formula I Form I has an XRPD pattern comprising degree 2θ-reflections (±0.2 degrees 2θ) at 7.7°, 11.2°, 15.2°, 18.5°, 20.3°, and 21.4° and one, two or three of the degree 2θ-reflections (+0.2 degrees 2θ) at 21.8°, 22.8°, and 24.6°. In some embodiments, crystalline Formula I Form I has an XRPD pattern comprising degree 2θ-reflections (±0.2 degrees 2θ) at 7.70, 11.2°, 15.2°, 18.5°, 20.3°, 21.4°, and 24.6°.

In certain embodiments, crystalline Formula I Form I has an XRPD pattern comprising degree 2θ-reflections (±0.2 degrees 2θ) at 7.70, 11.2°, and 20.3°. In some embodiments, crystalline Formula I Form I has an XRPD pattern comprising degree 2θ-reflections (±0.2 degrees 2θ) at 7.70, 11.2°, and 20.3° and one or more of the degree 2θ-reflections (±0.2 degrees 2θ) at 15.20, 18.5°, and 21.4°. In some embodiments, crystalline Formula I Form I has an XRPD pattern comprising degree 2θ-reflections (±0.2 degrees 2θ) at 7.7°, 11.2°, and 20.3° and one of the degree 2θ-reflections (±0.2 degrees 2θ) at 15.20, 18.5°, and 21.4°. In some embodiments, crystalline Formula I Form I has an XRPD pattern comprising degree 2θ-reflections (±0.2 degrees 2θ) at 7.70, 11.2°, and 20.3° and two of the degree 2θ-reflections (±0.2 degrees 2θ) at 15.2, 18.5°, and 21.4°. In some embodiments, crystalline Formula I Form I has an XRPD pattern comprising degree 2θ-reflections (±0.2 degrees 2θ) at 7.7°, 11.2°, 15.2°, 18.5°, 20.3°, and 21.4°. In some embodiments, crystalline Formula I Form I has an XRPD pattern comprising degree 2θ-reflections (±0.2 degrees 2θ) at 7.70, 11.2°, 15.2°, 18.5°, 20.3°, and 21.4° and one or more of the degree 2θ-reflections (±0.2 degrees 2θ) at 21.8°, 22.80, and 24.6°. In some embodiments, crystalline Formula I Form I has an XRPD pattern comprising degree 2θ-reflections (±0.2 degrees 2θ) at 7.70, 11.2°, 15.2°, 18.5°, 20.3°, and 21.4° and one of the degree 2θ-reflections (±0.2 degrees 2θ) at 21.8°, 22.80, and 24.6°. In some embodiments, crystalline Formula I Form I has an XRPD pattern comprising degree 2θ-reflections (±0.2 degrees 2θ) at 7.70, 11.2°, 15.2°, 18.5°, 20.3°, and 21.4° and two of the degree 2θ-reflections (±0.2 degrees 2θ) at 21.8°, 22.8°, and 24.6°. In some embodiments, crystalline Formula I Form I has an XRPD pattern comprising any three degree 2θ-reflections (±0.2 degrees 2θ) selected from the group consisting of 7.7°, 11.2°, 15.2°, 18.5°, 20.3°, 21.4°, 21.8°, 22.8°, and 24.6°. In some embodiments, crystalline Formula I Form I has an XRPD pattern comprising any six degree 2θ-reflections (±0.2 degrees 2θ) selected from the group consisting of 7.7°, 11.2°, 15.2°, 18.5°, 20.3°, 21.4°, 21.8°, 22.8°, and 24.6°. In some embodiments, crystalline Formula I Form I has an XRPD pattern comprising degree 2θ-reflections (±0.2 degrees 2θ) at 7.7°, 11.2°, 15.2°, 18.5°, 20.3°, 21.4°, 21.8°, 22.8°, and 24.6°.

Formula I Form II

In some embodiments, provided is a crystalline compound of Formula I (crystalline Formula I Form II), wherein the crystal structure exhibits an X-ray powder diffraction (XRPD) pattern substantially as shown in FIG. 5. Crystalline Formula I Form II may exhibit a differential scanning calorimetry (DSC) thermogram substantially as shown in FIG. 6. Crystalline Formula I Form II may exhibit a thermogravimetric analysis (TGA) thermogram substantially as shown in FIG. 7. Crystalline Formula I Form II may exhibit a dynamic vapor sorption (DVS) isotherm substantially as shown in FIG. 8.

In some embodiments of crystalline Formula I Form II, at least one, at least two, at least three, or all of the following (a)-(d) apply: (a) crystalline Formula I Form II has an XRPD pattern substantially as shown in FIG. 5; (b) crystalline Formula I Form II has a DSC thermogram substantially as shown in FIG. 6; (c) crystalline Formula I Form II has a TGA thermogram substantially as shown in FIG. 7; (d) crystalline Formula I Form II has a DVS isotherm substantially as shown in FIG. 8.

In some embodiments, crystalline Formula I Form II has at least one, at least two, at least three, or at least four of the following properties:

(a) an XRPD pattern substantially as shown in FIG. 5
(b) a DSC thermogram substantially as shown in FIG. 6
(c) a TGA thermogram substantially as shown in FIG. 7
(d) a DVS isotherm substantially as shown in FIG. 8

In some embodiments, crystalline Formula I Form II has an XRPD pattern displaying at least two, at least three, at least four, at least five, at least six, at least seven, at least eight, or at least nine of the degree 2θ-reflections with the greatest intensity as the XRPD pattern substantially as shown in FIG. 5.

In certain embodiments, crystalline Formula I Form II has an XRPD pattern comprising degree 2θ-reflections (±0.2 degrees 2θ) at 5.60, 13.1, and 22.4°. In some embodiments, crystalline Formula I Form II has an XRPD pattern comprising degree 2θ-reflections (±0.2 degrees 2θ) at 5.60, 13.10, and 22.4° and one or more of the degree 2θ-reflections (±0.2 degrees 2θ) at 11.20, 18.10, and 20.7°. In some embodiments, crystalline Formula I Form II has an XRPD pattern comprising degree 2θ-reflections (±0.2 degrees 2θ) at 5.6°, 13.10, and 22.4° and one of the degree 2θ-reflections (±0.2 degrees 2θ) at 11.20, 18.10, and 20.7°. In some embodiments, crystalline Formula I Form II has an XRPD pattern comprising degree 2θ-reflections (±0.2 degrees 2θ) at 5.60, 13.1°, and 22.4° and two of the degree 2θ-reflections (±0.2 degrees 2θ) at 11.20, 18.10, and 20.7°. In some embodiments, crystalline Formula I Form II has an XRPD pattern comprising degree 2θ-reflections (±0.2 degrees 2θ) at 5.6°, 11.2°, 13.10, 18.10, 20.7° and 22.4°. In some embodiments, crystalline Formula I Form II has an XRPD pattern comprising degree 2θ-reflections (±0.2 degrees 2θ) at 5.60, 11.2°, 13.1°, 18.10, 20.7° and 22.4° and one or more of the degree 2θ-reflections (±0.2 degrees 2θ) at 15.0°, 19.2°, 22.9°, and 28.10. In some embodiments, crystalline Formula I Form II has an XRPD pattern comprising degree 2θ-reflections (±0.2 degrees 2θ) at 5.60, 11.2°, 13.10, 18.10, 20.7°, and 22.4° and one of the degree 2θ-reflections (±0.2 degrees 2θ) at 15.00, 19.2°, 22.9°, and 28.10. In some embodiments, crystalline Formula I Form II has an XRPD pattern comprising degree 2θ-reflections (±0.2 degrees 2θ) at 5.60, 11.2°, 13.10, 18.10, 20.7°, and 22.4° and two of the degree 2θ-reflections (±0.2 degrees 2θ) at 15.00, 19.2°, 22.9°, and 28.1°. In some embodiments, crystalline Formula I Form II has an XRPD pattern comprising degree 2θ-reflections (±0.2 degrees 2θ) at 5.60, 11.2°, 13.1°, 18.1°, 20.7°, and 22.4° and three of the degree 2θ-reflections (±0.2 degrees 2θ) at 15.00, 19.2°, 22.9°, and 28.1°. In some embodiments, crystalline Formula I Form II has an XRPD pattern comprising any three degree 2θ-reflections (±0.2 degrees 2θ) selected from the group consisting of 5.6°, 11.2°, 13.10, 15.0°, 18.10, 19.2°, 20.7°, 22.4°, 22.9°, and 28.1°. In some embodiments, crystalline Formula I Form II has an XRPD pattern comprising any six degree 2θ-reflections (±0.2 degrees 2θ) selected from the group consisting of 5.6°, 11.2°, 13.10, 15.0°, 18.10, 19.2°, 20.7°, 22.4°, 22.9°, and 28.10. In some embodiments, crystalline Formula I Form II has an XRPD pattern comprising degree 2θ-reflections (±0.2 degrees 2θ) at 5.60, 11.2°, 13.1°, 15.0°, 18.10, 19.2°, 20.7°, 22.4°, 22.9°, and 28.10.

Formula I Vanillate Form I

In some embodiments, provided is a crystalline compound of Formula I (crystalline Formula I Vanillate Form I), wherein the crystal structure exhibits an X-ray powder diffraction (XRPD) pattern substantially as shown in FIG. 9. Crystalline Formula I Vanillate Form I may exhibit a differential scanning calorimetry (DSC) thermogram substantially as shown in FIG. 10. Crystalline Formula I Vanillate Form I may exhibit a thermogravimetric analysis (TGA) thermogram substantially as shown in FIG. 11. Crystalline Formula I Vanillate Form I may exhibit a dynamic vapor sorption (DVS) isotherm substantially as shown in FIG. 12.

In some embodiments of crystalline Formula I Vanillate Form I, at least one, at least two, at least three, or all of the following (a)-(d) apply: (a) crystalline Formula I Vanillate Form I has an XRPD pattern substantially as shown in FIG. 9; (b) crystalline Formula I Vanillate Form I has a DSC thermogram substantially as shown in FIG. 10; (c) crystalline Formula I Vanillate Form I has a TGA thermogram substantially as shown in FIG. 11; (d) crystalline Formula I Vanillate Form I has a DVS spectrum substantially as shown in FIG. 12.

In some embodiments, crystalline Formula I Vanillate Form I has at least one, at least two, at least three, or all of the following properties:
(a) an XRPD pattern substantially as shown in FIG. 9
(b) a DSC thermogram substantially as shown in FIG. 10
(c) a TGA thermogram substantially as shown in FIG. 11
(d) a DVS isotherm substantially as shown in FIG. 12

In some embodiments, crystalline Formula I Vanillate Form I has an XRPD pattern displaying at least two, at least three, at least four, at least five, at least six, at least seven, at least eight, or at least nine of the degree 2θ-reflections with the greatest intensity as the XRPD pattern substantially as shown in FIG. 9.

In certain embodiments, crystalline Formula I Vanillate Form I has an XRPD pattern comprising degree 2θ-reflections (±0.2 degrees 2θ) at 5.90, 9.00, and 11.8°. In some embodiments, crystalline Formula I Vanillate Form I has an XRPD pattern comprising degree 2θ-reflections (±0.2 degrees 2θ) at 5.90, 9.00, and 11.8° and one or more of the degree 2θ-reflections (±0.2 degrees 2θ) at 3.00, 10.70, and 15.2°. In some embodiments, crystalline Formula I Vanillate Form I has an XRPD pattern comprising degree 2θ-reflections (±0.2 degrees 2θ) at 5.90, 9.00, and 11.8° and one of the degree 2θ-reflections (±0.2 degrees 2θ) at 3.0°, 10.7°, and 15.2°. In some embodiments, crystalline Formula I Vanillate Form I has an XRPD pattern comprising degree 2θ-reflections (±0.2 degrees 2θ) at 5.90, 9.00, and 11.8° and two of the degree 2θ-reflections (±0.2 degrees 2θ) at 3.00, 10.70, and 15.2°. In some embodiments, crystalline Formula I Vanillate Form I has an XRPD pattern comprising degree 2θ-reflections (±0.2 degrees 2θ) at 3.00, 5.90, 9.00, 10.70, 11.8°, and 15.2°. In some embodiments, crystalline Formula I Vanillate Form I has an XRPD pattern comprising degree 2θ-reflections (±0.2 degrees 2θ) at 3.00, 5.90, 9.00, 10.70, 11.8°, and 15.2° and one or more of the degree 2θ-reflections (±0.2 degrees 2θ) at 20.40 and 24.5°. In some embodiments, crystalline Formula I Vanillate Form I has an XRPD pattern comprising degree 2θ-reflections (+0.2 degrees 2θ) at 3.00, 5.90, 9.00, 10.7°, 11.8°, and 15.2° and one of the degree 2θ-reflections (+0.2 degrees 2θ) at 20.40 and 24.5°. In some embodiments, crystalline Formula I Vanillate Form I has an XRPD pattern comprising any three degree 2θ-reflections (±0.2 degrees 2θ) selected from the group consisting of 3.0°, 5.9°, 9.0°, 10.7°, 11.8°, 15.2°, 20.4° and 24.5°. In some embodiments, crystalline Formula I Vanillate Form I has an XRPD pattern comprising any six degree 2θ-reflections (±0.2 degrees 2θ) selected from the group consisting of 3.0°, 5.9°, 9.0°, 10.7°, 11.8°, 15.2°, 20.4° and 24.5°. In some embodiments, crystalline Formula I Vanillate Form I has an XRPD pattern comprising degree 2θ-reflections (±0.2 degrees 2θ) at 3.00, 5.90, 9.00, 10.7°, 11.8°, 15.2°, 20.4° and 24.5°.

Formula I Vanillate Form II

In some embodiments, provided is a crystalline compound of Formula I (crystalline Formula I Vanillate Form II), wherein the crystal structure exhibits an X-ray powder diffraction (XRPD) pattern substantially as shown in FIG. 13. Crystalline Formula I Vanillate Form II may exhibit a differential scanning calorimetry (DSC) thermogram substantially as shown in FIG. 14. Crystalline Formula I Vanillate Form II may exhibit a thermogravimetric analysis (TGA) thermogram substantially as shown in FIG. 15. Crystalline Formula I Vanillate Form II may exhibit a dynamic vapor sorption (DVS) isotherm substantially as shown in FIG. 16.

In some embodiments of crystalline Formula I Vanillate Form II, at least one, at least two, at least three, or all of the following (a)-(d) apply: (a) crystalline Formula I Vanillate Form II has an XRPD pattern substantially as shown in FIG. 13; (b) crystalline Formula I Vanillate Form II has a DSC thermogram substantially as shown in FIG. 14; (c) crystalline Formula I Vanillate Form II has a TGA thermogram substantially as shown in FIG. 15; (d) crystalline Formula I Vanillate Form II has a DVS isotherm substantially as shown in FIG. 16.

In some embodiments, crystalline Formula I Vanillate Form II has at least one, at least two, at least three, or all of the following properties:
(a) an XRPD pattern substantially as shown in FIG. 13
(b) a DSC thermogram substantially as shown in FIG. 14
(c) a TGA thermogram substantially as shown in FIG. 15
(d) a DVS isotherm substantially as shown in FIG. 16

In some embodiments, crystalline Formula I Vanillate Form II has an XRPD pattern displaying at least two, at least three, at least four, at least five, at least six, at least seven, at least eight, or at least nine of the degree 2θ-reflections with the greatest intensity as the XRPD pattern substantially as shown in FIG. 13.

In certain embodiments, crystalline Formula I Vanillate Form II has an XRPD pattern comprising degree 2θ-reflections (±0.2 degrees 2θ) at 5.90, 11.80, and 15.5°. In some embodiments, crystalline Formula I Vanillate Form II has an XRPD pattern comprising degree 26-reflections (±0.2 degrees 2θ) at 5.90, 11.80, and 15.5° and one or more of the degree 26-reflections (±0.2 degrees 2θ) at 3.00, 10.90, and 14.7°. In some embodiments, crystalline Formula I Vanillate Form II has an XRPD pattern comprising degree 2θ-reflections (±0.2 degrees 2θ) at 5.90, 11.80, and 15.5° and one of the degree 2θ-reflections (±0.2 degrees 2θ) at 3.0°, 10.9°, and 14.7°. In some embodiments, crystalline Formula I Vanillate Form II has an XRPD pattern comprising degree 2θ-reflections (±0.2 degrees 2θ) at 5.90, 11.80, and 15.5° and two of the degree 2θ-reflections (±0.2 degrees 2θ) at 3.00, 10.90, and 14.7°. In some embodiments, crystalline Formula I Vanillate Form II has an XRPD pattern comprising degree 2θ-reflections (±0.2 degrees 2θ) at 3.00, 5.90, 10.90, 11.8°, 14.7°, and 15.5°. In some embodiments, crystalline Formula I Vanillate Form II has an XRPD pattern comprising degree 2θ-reflections (±0.2 degrees 2θ) at 3.00, 5.90, 10.90, 11.8°, 14.7°, and 15.5° and one or more of the degree 2θ-reflections (±0.2 degrees 2θ) at 19.3°, 20.80 and 24.4°. In some embodiments, crystalline Formula I Vanillate Form II has an XRPD pattern comprising degree 2θ-reflections (±0.2 degrees 2θ) at 3.00, 5.90, 10.90, 11.8°, 14.7°, and 15.5° and one of the degree 2θ-reflections (±0.2 degrees 2θ) at 19.30, 20.8° and 24.4°. In some embodiments, crystalline Formula I Vanillate Form II has an XRPD pattern comprising degree 2θ-reflections (±0.2 degrees 2θ) at 3.00, 5.90, 10.90, 11.8°, 14.7°, and 15.5° and two of the degree 2θ-reflections (+0.2 degrees 2θ) at 19.3°, 20.80 and 24.4°. In some embodiments, crystalline Formula I Vanillate Form II has an XRPD pattern comprising any three degree 2θ-reflections (±0.2 degrees 2θ) selected from the group consisting of 3.0°, 5.9°, 10.9°, 11.8°, 14.7°, 15.5°, 19.3°, 20.80 and 24.4°. In some embodiments, crystalline Formula I Vanillate Form II has an XRPD pattern comprising any six degree 2θ-reflections (±0.2 degrees 2θ) selected from the group consisting of 3.0°, 5.9°, 10.9°, 11.8°, 14.7°, 15.5°, 19.3°, 20.8° and 24.4°. In some embodiments, crystalline Formula I Vanillate Form II has an XRPD pattern comprising degree 2θ-reflections (±0.2 degrees 2θ) at 3.00, 5.90, 10.90, 11.8°, 14.7°, 15.5°, 19.3°, 20.8° and 24.4°.

Formula I Phosphate Form I

In some embodiments, provided is a crystalline compound of Formula I (crystalline Formula I Phosphate Form I), wherein the crystal structure exhibits an X-ray powder diffraction (XRPD) pattern substantially as shown in FIG. 17. Crystalline Formula I Phosphate Form I may exhibit a differential scanning calorimetry (DSC) thermogram substantially as shown in FIG. 18. Crystalline Formula I Phosphate Form I may exhibit a thermogravimetric analysis (TGA) thermogram substantially as shown in FIG. 19.

In some embodiments of crystalline Formula I Phosphate Form I, at least one, at least two, or all of the following (a)-(c) apply: (a) crystalline Formula I Phosphate Form I has an XRPD pattern substantially as shown in FIG. 17; (b) crystalline Formula I Phosphate Form I has a DSC thermogram substantially as shown in FIG. 18; (c) crystalline Formula I Phosphate Form I has a TGA thermogram substantially as shown in FIG. 19.

In some embodiments, crystalline Formula I Phosphate Form I has at least one, at least two, or all of the following properties:

(a) an XRPD pattern substantially as shown in FIG. 17
(b) a DSC thermogram substantially as shown in FIG. 18
(c) a TGA thermogram substantially as shown in FIG. 19

In some embodiments, crystalline Formula I Phosphate Form I has an XRPD pattern displaying at least two, at least three, at least four, at least five, at least six, at least seven, at least eight, or at least nine of the degree 2θ-reflections with the greatest intensity as the XRPD pattern substantially as shown in FIG. 17.

In certain embodiments, crystalline Formula I Phosphate Form I has an XRPD pattern comprising degree 2θ-reflections (±0.2 degrees 2θ) at 5.60, 13.2°, and 18.5°. In some embodiments, crystalline Formula I Phosphate Form I has an XRPD pattern comprising degree 2θ-reflections (±0.2 degrees 2θ) at 5.60, 13.2°, and 18.5° and one or more of the degree 2θ-reflections (±0.2 degrees 2θ) at 7.70, 9.3°, and 16.0°. In some embodiments, crystalline Formula I Phosphate Form I has an XRPD pattern comprising degree 2θ-reflections (±0.2 degrees 2θ) at 5.6°, 13.2°, and 18.5° and one of the degree 2θ-reflections (±0.2 degrees 2θ) at 7.70, 9.3°, and 16.0°. In some embodiments, crystalline Formula I Phosphate Form I has an XRPD pattern comprising degree 2θ-reflections (±0.2 degrees 2θ) at 5.60, 13.2°, and 18.5° and two of the degree 2θ-reflections (±0.2 degrees 2θ) at 7.70, 9.3°, and 16.0°. In some embodiments, crystalline Formula I Phosphate Form I has an XRPD pattern comprising degree 2θ-reflections (±0.2 degrees 2θ) at 5.60, 7.7°, 9.3°, 13.2°, 16.0°, and 18.5°. In some embodiments, crystalline Formula I Phosphate Form I has an XRPD pattern comprising degree 2θ-reflections (±0.2 degrees 2θ) at 5.60, 7.7°, 9.3°, 13.2°, 16.0°, and 18.5° and one or more of the degree 2θ-reflections (±0.2 degrees 2θ) at 3.30, 18.9° and 22.4°. In some embodiments, crystalline Formula I Phosphate Form I has an XRPD pattern comprising degree 2θ-reflections (±0.2 degrees 2θ) at 5.60, 7.7°, 9.3°, 13.2°, 16.0°, and 18.5° and one of the degree 2θ-reflections (±0.2 degrees 2θ) at 3.30, 18.9° and 22.4°. In some embodiments, crystalline Formula I Phosphate Form I has an XRPD pattern comprising degree 2θ-reflections (±0.2 degrees 2θ) at 5.60, 7.7°, 9.3°, 13.2°, 16.0°, and 18.5° and two of the degree 2θ-reflections (±0.2 degrees 2θ) at 3.30, 18.9° and 22.4°. In some embodiments, crystalline Formula I Phosphate Form I has an XRPD pattern comprising any three degree 2θ-reflections (±0.2 degrees 2θ) selected from the group consisting of 3.3°, 5.6°, 7.7°, 9.3°, 13.2°, 16.0°, 18.5°, 18.9° and 22.4°. In some embodiments, crystalline Formula I Phosphate Form I has an XRPD pattern comprising any six degree 2θ-reflections (±0.2 degrees 2θ) selected from the group consisting of 3.3°, 3.3°, 5.60, 7.7°, 9.3°, 13.2°, 16.0°, 18.5°, 18.9° and 22.4°. In some embodiments, crystalline Formula I Phosphate Form I has an XRPD pattern comprising degree 2θ-reflections (±0.2 degrees 2θ) at 3.30, 5.6°, 7.7°, 9.3°, 13.2°, 16.0°, 18.5°, 18.9° and 22.4°. In some embodiments, crystalline Formula I Phosphate Form I has an XRPD pattern comprising degree 2θ-reflections (±0.1 degrees 2θ) at 3.3°, 5.6°, 7.7°, 9.3°, 13.2°, 16.0°, 18.5°, 18.9° and 22.4°. In some embodiments, crystalline Formula I Phosphate Form I has an XRPD pattern comprising degree 2θ-reflections (±0.05 degrees 2θ) at 3.30, 5.6°, 7.7°, 9.3°, 13.2°, 16.0°, 18.5°, 18.9° and 22.4°.

Formula I Xinafoate Form I

In some embodiments, provided is a crystalline compound of Formula I (crystalline Formula I Xinafoate Form I), wherein the crystal structure exhibits an X-ray powder diffraction (XRPD) pattern substantially as shown in FIG. 20. Crystalline Formula I Xinafoate Form I may exhibit a differential scanning calorimetry (DSC) thermogram substantially as shown in FIG. 21. Crystalline Formula I Xinafoate Form I may exhibit a thermogravimetric analysis (TGA) thermogram substantially as shown in FIG. 22.

In some embodiments of crystalline Formula I Xinafoate Form I, at least one, at least two, or all of the following (a)-(c) apply: (a) crystalline Formula I Xinafoate Form I has an XRPD pattern substantially as shown in FIG. 20; (b) crystalline Formula I Xinafoate Form I has a DSC thermogram substantially as shown in FIG. 21; (c) crystalline Formula I Xinafoate Form I has a TGA thermogram substantially as shown in FIG. 22.

In some embodiments, crystalline Formula I Xinafoate Form I has at least one, at least two, or all of the following properties:

(a) an XRPD pattern substantially as shown in FIG. 20
(b) a DSC thermogram substantially as shown in FIG. 21
(c) a TGA thermogram substantially as shown in FIG. 22

In some embodiments, crystalline Formula I Xinafoate Form I has an XRPD pattern displaying at least two, at least three, at least four, at least five, at least six, at least seven, at least eight, or at least nine of the degree 2θ-reflections with the greatest intensity as the XRPD pattern substantially as shown in FIG. 20.

In certain embodiments, crystalline Formula I Xinafoate Form I has an XRPD pattern comprising degree 2θ-reflections (±0.2 degrees 2θ) at 6.90, 15.10, and 24.80. In some embodiments, crystalline Formula I Xinafoate Form I has an XRPD pattern comprising degree 2θ-reflections (±0.2 degrees 2θ) at 6.90, 15.1°, and 24.80 and one or more of the degree 2θ-reflections (±0.2 degrees 2θ) at 12.40, 17.2°, and 18.0°. In some embodiments, crystalline Formula I Xinafoate Form I has an XRPD pattern comprising degree 2θ-reflections (±0.2 degrees 2θ) at 6.90, 15.10, and 24.80 and one of the degree 2θ-reflections (±0.2 degrees 2θ) at 12.4°, 17.2°, and 18.0°. In some embodiments, crystalline Formula I Xinafoate Form I has an XRPD pattern comprising degree 2θ-reflections (±0.2 degrees 2θ) at 6.90, 15.10, and 24.8° and two of the degree 2θ-reflections (±0.2 degrees 2θ) at 12.40, 17.2°, and 18.0°. In some embodiments, crystalline Formula I Xinafoate Form I has an XRPD pattern comprising degree 2θ-reflections (±0.2 degrees 2θ) at 6.90, 12.40, 15.1°, 17.2°, 18.0°, and 24.8°. In some embodiments, crystalline Formula I Xinafoate Form I has an XRPD pattern comprising degree 2θ-reflections (±0.2 degrees 2θ) at 6.90, 12.40, 15.1°, 17.2°, 18.0°, and 24.8° and one or more of the degree 2θ-reflections (±0.2 degrees 2θ) at 10.20, 19.0°, and 23.6°. In some embodiments, crystalline Formula I Xinafoate Form I has an XRPD pattern comprising degree 2θ-reflections (±0.2 degrees 2θ) at 6.90, 12.40, 15.10, 17.2°, 18.0°, and 24.8° and one of the degree 2θ-reflections (±0.2 degrees 2θ) at 10.20, 19.0°, and 23.6°. In some embodiments, crystalline Formula I Xinafoate Form I has an XRPD pattern comprising degree 2θ-reflections (±0.2 degrees 2θ) at 6.90, 12.40, 15.10, 17.2°, 18.0°, and 24.80 and two of the degree 2θ-reflections (+0.2 degrees 2θ) at 10.20, 19.0°, and 23.6°. In some embodiments, crystalline Formula I Xinafoate Form I has an XRPD pattern comprising any three degree 2θ-reflections (±0.2 degrees 2θ) selected from the group consisting of 6.9°, 10.2°, 12.4°, 15.10, 17.2°, 18.0°, 19.0°, 23.6° and 24.8°. In some embodiments, crystalline Formula I Xinafoate Form I has an XRPD pattern comprising any six degree 2θ-reflections (±0.2 degrees 2θ) selected from the group consisting of 6.9°, 10.2°, 12.4°, 15.1°, 17.2°, 18.0°, 19.0°, 23.6° and 24.8°. In some embodiments, crystalline Formula I Xinafoate Form I has an XRPD pattern comprising degree 2θ-reflections (±0.2 degrees 2θ) at 6.90, 10.20, 12.4°, 15.1°, 17.2°, 18.0°, 19.0°, 23.6° and 24.80.

Formula I Phosphate Acetonitrile Solvate Form I

In some embodiments, provided is a crystalline compound of Formula I (crystalline Formula I Phosphate Acetonitrile Solvate Form I), wherein the crystal structure exhibits an X-ray powder diffraction (XRPD) pattern substantially as shown in FIG. 23.

In some embodiments, crystalline Formula I Phosphate Acetonitrile Solvate Form I has an XRPD pattern displaying at least two, at least three, at least four, at least five, at least six, at least seven, at least eight, or at least nine of the degree 2θ-reflections with the greatest intensity as the XRPD pattern substantially as shown in FIG. 23.

In certain embodiments, crystalline Formula I Phosphate Acetonitrile Solvate Form I has an XRPD pattern comprising degree 2θ-reflections (±0.2 degrees 2θ) at 4.90, 13.20, and 18.50. In some embodiments, crystalline Formula I Phosphate Acetonitrile Solvate Form I has an XRPD pattern comprising degree 2θ-reflections (±0.2 degrees 2θ) at 4.90, 13.20, and 18.5° and one or more of the degree 2θ-reflections (±0.2 degrees 2θ) at 6.70, 16.0°, and 20.0°. In some embodiments, crystalline Formula I Phosphate Acetonitrile Solvate Form I has an XRPD pattern comprising degree 2θ-reflections (±0.2 degrees 2θ) at 4.90, 13.20, and 18.5° and one of the degree 2θ-reflections (±0.2 degrees 2θ) at 6.70, 16.0°, and 20.0°. In some embodiments, crystalline Formula I Phosphate Acetonitrile Solvate Form I has an XRPD pattern comprising degree 2θ-reflections (±0.2 degrees 2θ) at 4.90, 13.20, and 18.5° and two of the degree 2θ-reflections (±0.2 degrees 2θ) at 6.70, 16.0°, and 20.0°. In some embodiments, crystalline Formula I Phosphate Acetonitrile Solvate Form I has an XRPD pattern comprising degree 2θ-reflections (±0.2 degrees 2θ) at 4.90, 6.70, 13.2°, 16.0°, 18.5° and 20.0°. In some embodiments, crystalline Formula I Phosphate Acetonitrile Solvate Form I has an XRPD pattern comprising degree 2θ-reflections (±0.2 degrees 2θ) at 4.90, 6.70, 13.2°, 16.0°, 18.5° and 20.0° and one or more of the degree 2θ-reflections (±0.2 degrees 2θ) at 3.00, 14.40 and 22.7°. In some embodiments, crystalline Formula I Phosphate Acetonitrile Solvate Form I has an XRPD pattern comprising degree 2θ-reflections (±0.2 degrees 2θ) at 4.90, 6.70, 13.2°, 16.0°, 18.5° and 20.0° and one of the degree 2θ-reflections (±0.2 degrees 2θ) at 3.00, 14.40 and 22.7°. In some embodiments, crystalline Formula I Phosphate Acetonitrile Solvate Form I has an XRPD pattern comprising degree 2θ-reflections (±0.2 degrees 2θ) at 4.90, 6.70, 13.2°, 16.0°, 18.5° and 20.0° and two of the degree 2θ-reflections (±0.2 degrees 2θ) at 3.00, 14.40 and 22.7°. In some embodiments, crystalline Formula I Phosphate Acetonitrile Solvate Form I has an XRPD pattern comprising any three degree 2θ-reflections (±0.2 degrees 2θ) selected from the group consisting of 3.0°, 4.9°, 6.7°, 13.2°, 14.4°, 16.0°, 18.5°, 20.0° and 22.7°. In some embodiments, crystalline Formula I Phosphate Acetonitrile Solvate Form I has an XRPD pattern comprising degree 2θ-reflections (±0.2 degrees 2θ) at 3.00, 4.90, 6.70, 13.2°, 14.4°, 16.0°, 18.5°, 20.0° and 22.7°.

Pharmaceutical Compositions

For the purposes of administration, in certain embodiments, the compounds described herein are administered as a raw chemical or are formulated as pharmaceutical compositions. Pharmaceutical compositions of the present invention comprise a therapeutically effective amount of a compound of Formula I, and at least one pharmaceutically acceptable excipient. The compound of Formula I is present in the composition in an amount which is effective to treat a particular disease or condition of interest. The activity of compounds of Formula I can be determined by one skilled in the art, for example, as described herein. Appropriate therapeutically effective concentrations and dosages can be readily determined by one skilled in the art. In certain embodiments, a compound of Formula I is present in the pharmaceutical composition in an amount from about 10-48 mg. In certain embodiments, a compound of Formula I is present in the pharmaceutical composition in an amount from about 20-40 mg. In certain embodiments, a compound of Formula I is present in the pharmaceutical composition in an amount from about 25-35 mg. In certain embodiments, a compound of Formula I is present in the pharmaceutical composition in an amount from about 30 mg.

In certain embodiments, a compound of Formula I is present in the pharmaceutical composition in an amount from about 30-90 mg. In some embodiments, a compound of Formula I is present in the pharmaceutical composition in an amount from about 60-90 mg. In some embodiments, a compound of Formula I is present in the pharmaceutical composition in an amount of about 60 mg. In some embodiments, a compound of Formula I is present in the pharmaceutical composition in an amount of about 90 mg.

Administration of the compounds of the invention in pure form, or in an appropriate pharmaceutical composition, can be carried out via any of the accepted modes of administration of agents for serving similar utilities. The pharmaceutical compositions of the invention can be prepared by combining a compound of the invention with an appropriate pharmaceutically acceptable excipient, and may be formulated into preparations in solid, semi-solid, liquid or gaseous forms, such as tablets, capsules, powders, granules, ointments, solutions, suppositories, injections, inhalants, gels, microspheres, and aerosols. The pharmaceutical compositions of the invention can be prepared by combining a compound of the invention with an appropriate pharmaceutically acceptable excipient, and may be formulated into preparations in solid, semi-solid, liquid or gaseous forms, such as solid dispersions and solid solutions. Typical routes of administering such pharmaceutical compositions include, without limitation, oral, topical, transdermal, inhalation, parenteral, sublingual, buccal, rectal, vaginal, and intranasal. In a specific embodiment, the pharmaceutical composition is a tablet. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see *Remington: The Science and Practice of Pharmacy*, 20th Edition (Philadelphia College of Pharmacy and Science, 2000). The composition to be administered will, in any event, contain a therapeutically effective amount of a compound of the invention for treatment of a disease or condition of interest in accordance with the teachings of this invention.

The pharmaceutical compositions of the invention may be prepared by methodology well known in the pharmaceutical art. For example, a pharmaceutical composition intended to be administered by injection can be prepared by combining a compound of the invention with sterile, distilled water so as to form a solution. A surfactant or other solubilizing excipient may be added to facilitate the formation of a homogeneous solution or suspension. Surfactants are compounds that non-covalently interact with the compound of the invention so as to facilitate dissolution or homogeneous suspension of the compound in the aqueous delivery system.

In other embodiments, a solid pharmaceutical composition intended for oral administration can be prepared by mixing a therapeutically effective amount of a compound of the invention with at least one suitable pharmaceutically acceptable excipient to form a solid preformulation composition, which then may be readily subdivided into equally effective unit dosage forms such as tablets, pills and capsules. Accordingly, in some embodiments, a pharmaceutical composition is provided, which includes a therapeutically effective amount of a compound of Formula I and a pharmaceutically acceptable excipient.

The compounds of the invention are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy. In some embodiments, the compounds of the invention can be administered alone or in combination with other antiviral agents one time a day, or two times a day, or three times a day, or four times a day, for as long as the patient is infected, latently infected, or to prevent infection (e.g. for multiple years, months, weeks, or days).

Provided are also compositions comprising a compound of Formula I as described herein. In a particular embodiment, a composition comprising one of the compounds of Formula I described herein is provided. In a particular embodiment, a composition comprising two of the compounds of Formula I described herein is provided. In a particular embodiment, a composition comprising three of the compounds of Formula I described herein is provided. In a particular embodiment, a composition comprising four of the compounds of Formula I described herein is provided. In other embodiments, the compositions described herein may comprise substantially pure crystalline forms, or may be substantially free of other crystalline forms and/or impurities.

In some embodiments, the composition comprises a crystalline form of Formula I. In certain embodiments are provided compositions comprising a crystalline form as described herein, wherein the Formula I within the composition is substantially pure (i.e., substantially pure Formula I Form I; Formula I Form II; Formula I Vanillate Form I; Formula I Vanillate Form II; Formula I Phosphate Form I; Formula I Xinafoate Form I; and Formula I Phosphate Acetonitrile Solvate Form I described herein). In particular embodiments of compositions comprising a crystalline form of Formula I, at least about 50%, at least about 60%, at least about 70%, at least about 80%, at least about 85%, at least about 90%, at least about 95%, at least about 96%, at least about 97%, at least about 98%, or at least about 99% of Formula I present in the composition is one of the crystalline forms disclosed herein. In certain embodiments, the composition includes at least about 50%, at least about 60%, at least about 70%, at least about 80%, at least about 85%, at least about 90%, at least about 95%, at least about 96%, at least about 97%, at least about 98%, or at least about 99% of one of the crystalline forms of Formula I.

In other embodiments of compositions comprising a crystalline form disclosed herein, less than about 50%, less than about 40%, less than about 30%, less than about 20%, less than about 10%, less than about 5%, less than about 4%, less than about 3%, less than about 2% or less than about 1% of Formula I present in the composition are other amorphous or crystal forms of Formula I and/or impurities.

In yet other embodiments of compositions comprising the crystalline forms disclosed herein, impurities make up less than about 5%, less than about 4%, less than about 3%, less than about 2% or less than about 1% of the total mass relative to the mass of the crystalline forms present. Impurities may, for example, include by-products from synthesizing Formula I, contaminants, degradation products, other crystalline forms, amorphous form, water, and solvents. In certain embodiments, impurities include by-products from the process of synthesizing Formula I. In certain embodiments, impurities include contaminants from the process of synthesizing Formula I. In certain embodiments, impurities include degradation products of Formula I. In certain embodiments, impurities include other crystalline forms of Formula I. In certain embodiments, impurities include other crystalline forms of Formula I and/or amorphous forms of Formula I. In certain embodiments, impurities include water or solvent. In certain embodiments of compositions comprising a crystalline form disclosed herein, impurities are selected from the group consisting of by-products from synthesizing Formula I, contaminants, degradation products, other crystalline forms, amorphous forms, water, solvents and combinations thereof.

Combination Therapy

In some embodiments, disclosed herein are oral dosage forms (e.g., tablets) comprising a novel crystalline forms of ethyl ((S)-((((2R,5R)-5-(6-amino-9H-purin-9-yl)-4-fluoro-2,5-dihydrofuran-2-yl)oxy)methyl)(phenoxy)phosphoryl)-L-alaninate (e.g., a compound of Formula I Form I and/or Formula I Form II) and at least one additional therapeutic agent. In some embodiments, the oral dosage forms disclosed herein comprise novel crystal forms of ethyl ((S)-((((2R,5R)-5-(6-amino-9H-purin-9-yl)-4-fluoro-2,5-dihydrofuran-2-yl)oxy)methyl)(phenoxy)phosphoryl)-L-alaninate (e.g., a compound of Formula I Form I and/or Formula I Form II) and one, two, or three additional therapeutic agents.

In some embodiments, the oral dosage forms disclosed herein comprise four active pharmaceutical ingredients: the compound of Formula I (or a pharmaceutically acceptable salt, co-crystal, or solvate thereof), the compound of Formula II (or a pharmaceutically acceptable salt, co-crystal, or solvate thereof), the compound of Formula III (or a pharmaceutically acceptable salt, co-crystal, or solvate thereof), and the compound of Formula IV (or a pharmaceutically acceptable salt, co-crystal, or solvate thereof).

Ethyl ((S)-((((2R,5R)-5-(6-amino-9H-purin-9-yl)-4-fluoro-2,5-dihydrofuran-2-yl)oxy)methyl)(phenoxy)phosphoryl)-L-alaninate Ethyl ((S)-((((2R,5R)-5-(6-amino-9H-purin-9-yl)-4-fluoro-2,5-dihydrofuran-2-yl)oxy)methyl)(phenoxy)phosphoryl)-L-alaninate (Formula I), is a prodrug of an HIV reverse-transcriptase (RT) inhibitor. This compound has a favorable in vitro resistance profile with activity against Nucleoside RT Inhibitor (NRTI)-Resistance Mutations, such as M184V, K65R, L74V, and one or more (e.g., 1, 2, 3, or 4) TAMs (thymidine analogue mutations). It has the following formula (see, e.g., U.S. Pat. No. 7,871,991):

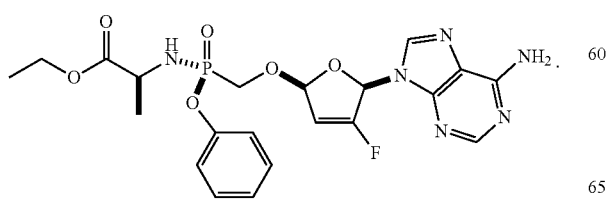

(I)

In some embodiments, solid oral dosage forms containing 5-50 mg of the compound of Formula I, or a pharmaceutically acceptable salt, co-crystal, or solvate thereof, are provided. In some embodiments, solid oral dosage forms containing 7-40 mg of the compound of Formula I, or a pharmaceutically acceptable salt, co-crystal, or solvate thereof, are provided. In some embodiments, solid oral dosage forms containing 10-30 mg of the compound of Formula I, or a pharmaceutically acceptable salt, co-crystal, or solvate thereof, are provided.

In some In some embodiments, solid oral dosage forms containing 50-90 mg of the compound of Formula I, or a pharmaceutically acceptable salt, co-crystal, or solvate thereof, are provided. In some embodiments, solid oral dosage forms containing 60-90 mg of the compound of Formula I, or a pharmaceutically acceptable salt, co-crystal, or solvate thereof, are provided. In some embodiments, solid oral dosage forms containing 60 mg of the compound of Formula I, or a pharmaceutically acceptable salt, co-crystal, or solvate thereof, are provided. In some embodiments, solid oral dosage forms containing 90 mg of the compound of Formula I, or a pharmaceutically acceptable salt, co-crystal, or solvate thereof, are provided.

In some embodiments, solid oral dosage forms disclosed herein include a novel form of Formula I. In some embodiments, the novel form of Formula I is amorphous. In some embodiments, the novel form of Formula I is crystalline. In some embodiments, the crystalline form of Formula I is the compound of Formula I Form I. In some embodiments, the crystalline form of Formula I is the compound of Formula I Form II.

In some embodiments, solid oral dosage forms disclosed herein include the compound of Formula I, usually in the form of a pharmaceutically acceptable salt, co-crystal, or solvate. The compound of Formula I can be present within an oral dosage form in solvated or unsolvated form, and references to "Formula I" include both of these forms.

In some embodiments, the compound of Formula I is the vanillate (i.e., Formula Ia), having the following structure:

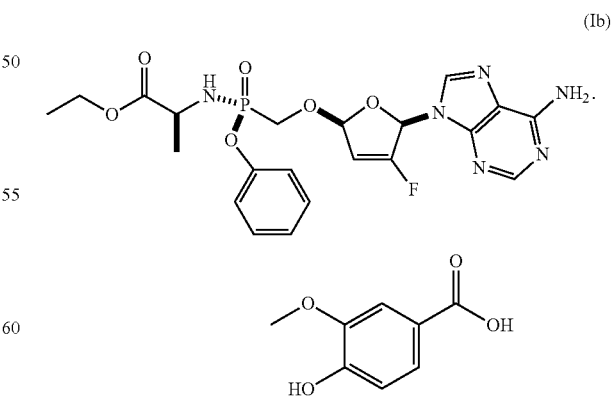

(Ib)

In some embodiments, Formula Ib is Formula I Vanillate Form I. In some embodiments, Formula Ib is Formula I Vanillate Form II.

In some embodiments, the compound of Formula I is the phosphate (i.e., Formula Ic), having the following structure:

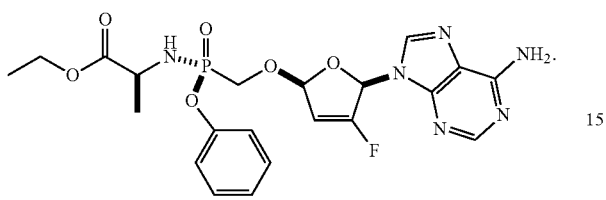

(Ic)

$H_3PO_4$

In some embodiments, Formula Ic is Formula I Phosphate Form I.

In some embodiments, the compound of Formula I is the xinafoate (i.e., Formula Id), having the following structure:

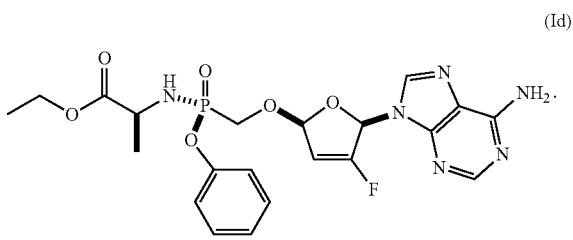

(Id)

In some embodiments, Formula Id is Formula I Xinafoate Form I.

In some embodiments, the novel crystalline form of ethyl ((S)-((((2R,5R)-5-(6-amino-9H-purin-9-yl)-4-fluoro-2,5-dihydrofuran-2-yl)oxy)methyl)(phenoxy)phosphoryl)-L-alaninate is a solvate. In some embodiments, the solvate is ethyl ((S)-((((2R,5R)-5-(6-amino-9H-purin-9-yl)-4-fluoro-2,5-dihydrofuran-2-yl)oxy)methyl)(phenoxy)phosphoryl)-L-alaninate phosphate acetonitrile solvate Form I (i.e., Formula I Phosphate Acetonitrile Solvate Form I).

(2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide (Formula II), is a potent HIV integrase inhibitor with in vitro activity against wild type HIV-1. It has the following formula (see WO2014/100323)

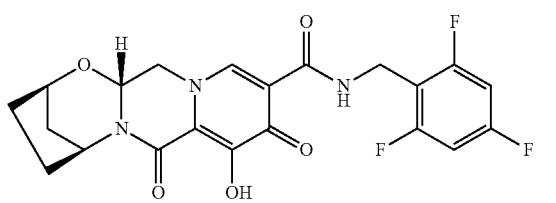

(II)

Its IUPAC name is (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide. Its CAS name is 2,5-Methanopyrido[1',2':4,5]pyrazino[2,1-b][1,3]oxazepine-10-carboxamide, 2,3,4,5,7,9,13,13a-octahydro-8-hydroxy-7,9-dioxo-N-[(2,4,6-trifluorophenyl)methyl]-, (2R,5S,13aR). The compound of Formula II is also referred to as bictegravir.

Solid oral dosage forms disclosed herein include the compound of Formula II, usually in the form of a pharmaceutically acceptable salt. The compound of Formula II can be present within an oral dosage form in solvated or unsolvated form, and references to "Formula II" include both of these forms. In certain embodiments, the compound of Formula II is in the form of the compound of Formula IIa, having the formula below:

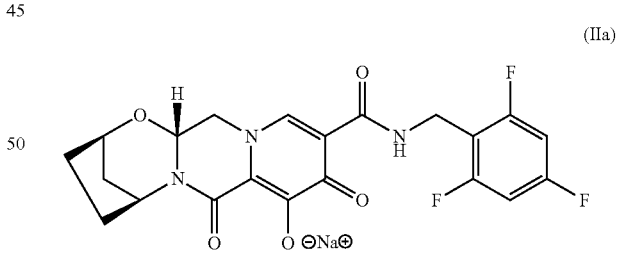

(IIa)

One name for the compound of Formula (IIa) is sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate.

Cobicistat

Cobicistat is described in WO 2008/010921, incorporated herein by reference, and has been shown to be a mechanism-based inhibitor of CYP3A enzymes, CYP3A4 and CYP3A5, with greater specificity than ritonavir. Xu et al., ACS Med. Chem. Lett. (2010), 1, pp. 209-13. The structure of cobicistat is shown below (Formula III):

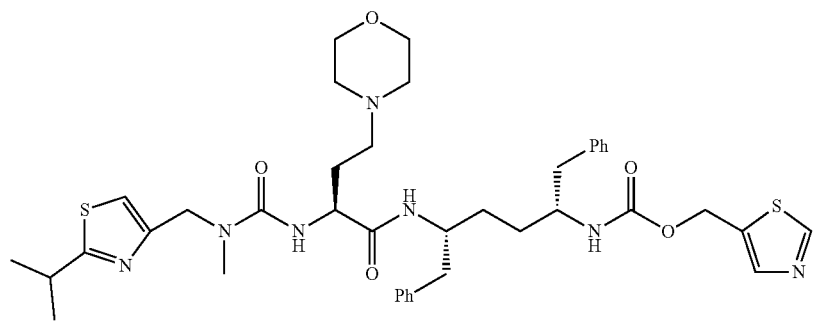

(III)

Cobicistat refers to 1,3-thiazol-5-ylmethyl (2R,5R)-(5-{[(2S)-2-[(methyl {[2-(propan-2-yl)-1,3-thiazol-4-yl]methyl}carbamoyl)amino]]-4-(morpholin-4-yl)butanamido}-1,6-diphenylhexan-2-yl)carbamate). It is currently authorized as part of products such as TYBOST (cobicistat 150 mg), STRIBILD® (emtricitabine 200 mg, cobicistat 150 mg, tenofovir disoproxil fumarate 300 mg, elvitegravir 150 mg), GENVOYA® (emtricitabine 200 mg, cobicistat 150 mg, tenofovir alafenamide 10 mg, elvitegravir 150 mg), and PREZCOBIX® (darunavir 800 mg and cobicistat 150 mg).

Solid oral dosage forms disclosed herein include cobicistat. Cobicistat can be present within an oral dosage form in solvated or unsolvated form, and references to "cobicistat" include both of these forms.

Darunavir

Darunavir is a HIV-1 protease inhibitor having the formula below (Formula IV) (see, e.g., U.S. Pat. No. 6,248,775):

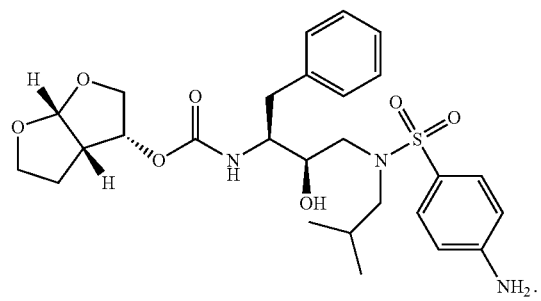

(IV)

Darunavir refers to as [(1S,2R)-3-[[(4-aminophenyl)sulfonyl](2-methylpropyl)amino]-2-hydroxy-1-(phenylmethyl)propyl]-carbamic acid (3R,3aS,6aR)-hexahydrofuro[2,3-b]furan-3-yl ester monoethanolate. It is currently authorized as part of products such as PREZCOBIX® (darunavir 800 mg and cobicistat 150 mg) and PREZISTA® (darunavir 75 mg, 150 mg, 600 mg, and 800 mg).

In some embodiments, the compound of Formula IV is a solvate. In some embodiments, the solvate of the compound of Formula IV is the compound of Formula IVa, having the formula below:

(IVa)

Solid oral dosage forms disclosed herein include darunavir, optionally as a pharmaceutically acceptable salt, co-crystal, or solvate thereof. Darunavir can be present within an oral dosage form in solvated or unsolvated form, and references to "darunavir" include both of these forms.

Solid Oral Dosage Forms

In some embodiments, disclosed herein is a solid oral dosage form comprising:

(a) a compound of Formula I:

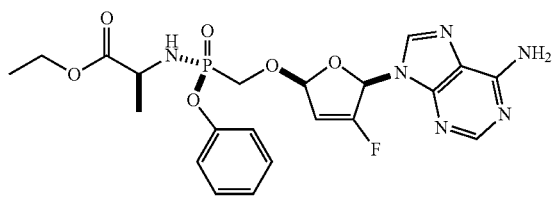

(I)

or a pharmaceutically acceptable salt, co-crystal, or solvate thereof (e.g., the vanillate of Formula Ia, the phosphate of Formula Ib, the xinafoate of Formula Ic, and/or the phosphate acetonitrile solvate of Formula I);

(b) a compound of Formula II:

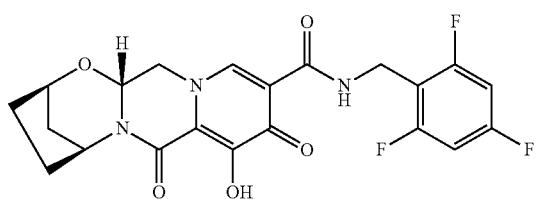

or a pharmaceutically acceptable salt, co-crystal, or solvate thereof;
(c) a compound of Formula III:

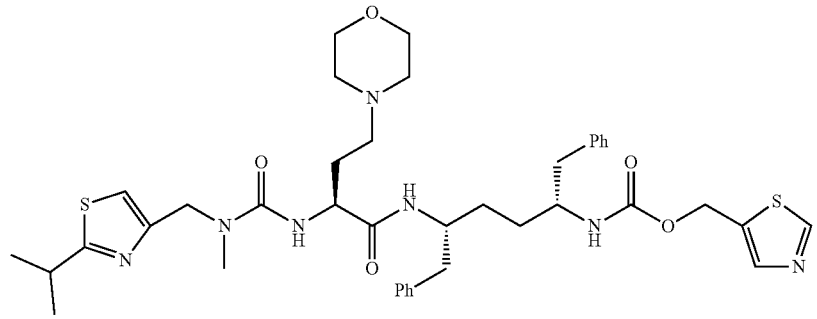

or a pharmaceutically acceptable salt, co-crystal, or solvate thereof;
(d) a compound of Formula IV:

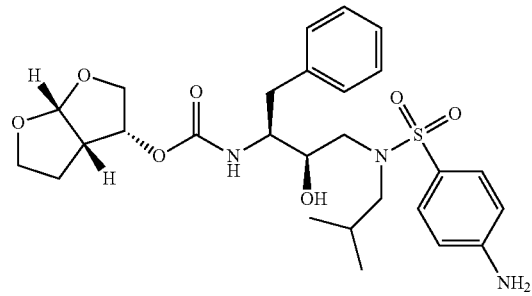

or a pharmaceutically acceptable salt, co-crystal, or solvate thereof.

In some embodiments, the solid oral dosage form comprises an amorphous form of Formula I. In some embodiments, the solid oral dosage form comprises a crystalline form of Formula I. In some embodiments, the crystalline form of Formula I is Formula I Form I. In some embodiments, the crystalline form of Formula I is Formula I Form II. In some embodiments, the crystalline form of Formula I is Formula I Vanillate Form I. In some embodiments, the crystalline form of Formula I is Formula I Vanillate Form II. In some embodiments, the crystalline form of Formula I is Formula I Phosphate Form I. In some embodiments, the crystalline form of Formula I is Formula I Xinafoate Form I. In some embodiments, the crystalline form of Formula I is Formula I Phosphate Acetonitrile Solvate Form I.

In some embodiments, the solid oral dosage form further comprises a plurality of silicon dioxide particles. In some embodiments, the compound of Formula III is adsorbed onto the silicon dioxide particles.

The solid oral dosage forms disclosed herein are intended for pharmaceutical use in human subjects. Accordingly, they must be of an appropriate size and weight for oral human administration (e.g., they should have a total weight of less than about 1.8 g, less than about 1.5 g, or less than about 1.0 g), in addition to being therapeutically efficacious.

In some embodiments, disclosed herein is a tablet comprising: (a) the compound of Formula I, or a pharmaceutically acceptable salt, co-crystal, or solvate thereof, (b) the compound of Formula II, or a pharmaceutically acceptable salt, co-crystal, or solvate thereof, (c) cobicistat, or a pharmaceutically acceptable salt, co-crystal, or solvate thereof, and (d) darunavir, or a pharmaceutically acceptable salt, co-crystal, or solvate thereof is provided. In some embodiments, a single-layer tablet comprising (a) the compound of Formula I, or a pharmaceutically acceptable salt, co-crystal, or solvate thereof, (b) the compound of Formula II, or a pharmaceutically acceptable salt, co-crystal, or solvate thereof, (c) cobicistat, or a pharmaceutically acceptable salt, co-crystal, or solvate thereof, and (d) darunavir, or a pharmaceutically acceptable salt, co-crystal, or solvate thereof is provided. Additionally, a multilayer tablet comprising (a) the compound of Formula I, or a pharmaceutically acceptable salt, co-crystal, or solvate thereof, (b) the compound of Formula II, or a pharmaceutically acceptable salt, co-crystal, or solvate thereof, (c) cobicistat, or a pharmaceutically acceptable salt, co-crystal, or solvate thereof, and (d) darunavir, or a pharmaceutically acceptable salt, co-crystal, or solvate thereof is provided.

In one embodiment, kits comprising a compound disclosed herein, or a pharmaceutically acceptable salt thereof, in combination with one or more (e.g., one, two, three, one or two, or one to three) additional therapeutic agents are provided.

In certain embodiments, a method for treating or preventing an HIV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, one or two, or one to three) additional therapeutic agents. In one embodiment, a method for treating an HIV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, one or two, or one to three) additional therapeutic agents.

In one embodiment, pharmaceutical compositions comprising a compound disclosed herein, or a pharmaceutically acceptable salt thereof, in combination with one or more (e.g., one, two, three, one or two, or one to three) additional therapeutic agents, and a pharmaceutically acceptable carrier, diluent, or excipient are provided.

In certain embodiments, the present disclosure provides a method for treating an HIV infection, comprising administering to a patient in need thereof a therapeutically effective amount of a compound disclosed herein, or a pharmaceutically acceptable salt thereof, in combination with a therapeutically effective amount of one or more additional therapeutic agents which are suitable for treating an HIV infection.

In certain embodiments, a compound disclosed herein, or a pharmaceutically acceptable salt thereof, is combined with one, two, three, four, or more additional therapeutic agents. In certain embodiments, a compound disclosed herein, or a pharmaceutically acceptable salt thereof, is combined with two additional therapeutic agents. In other embodiments, a compound disclosed herein, or a pharmaceutically acceptable salt thereof, is combined with three additional therapeutic agents. In further embodiments, a compound disclosed herein, or a pharmaceutically acceptable salt thereof, is combined with four additional therapeutic agents. The one, two, three, four, or more additional therapeutic agents can be different therapeutic agents selected from the same class of therapeutic agents, and/or they can be selected from different classes of therapeutic agents.

Administration of HIV Combination Therapy

In certain embodiments, a compound disclosed herein is administered with one or more additional therapeutic agents. Co-administration of a compound disclosed herein with one or more additional therapeutic agents generally refers to simultaneous or sequential administration of a compound disclosed herein and one or more additional therapeutic agents, such that therapeutically effective amounts of the compound disclosed herein and the one or more additional therapeutic agents are both present in the body of the patient. When administered sequentially, the combination may be administered in two or more administrations.

Co-administration includes administration of unit dosages of the compounds disclosed herein before or after administration of unit dosages of one or more additional therapeutic agents. For example, the compound disclosed herein may be administered within seconds, minutes, or hours of the administration of the one or more additional therapeutic agents. In some embodiments, a unit dose of a compound disclosed herein is administered first, followed within seconds or minutes by administration of a unit dose of one or more additional therapeutic agents. Alternatively, a unit dose of one or more additional therapeutic agents is administered first, followed by administration of a unit dose of a compound disclosed herein within seconds or minutes. In other embodiments, a unit dose of a compound disclosed herein is administered first, followed, after a period of hours (e.g., 1-12 hours), by administration of a unit dose of one or more additional therapeutic agents. In yet other embodiments, a unit dose of one or more additional therapeutic agents is administered first, followed, after a period of hours (e.g., 1-12 hours), by administration of a unit dose of a compound disclosed herein.

In certain embodiments, a compound disclosed herein is combined with one or more additional therapeutic agents in a unitary dosage form for simultaneous administration to a patient, for example as a solid dosage form for oral administration.

In In certain embodiments, a compound of Formula (I) is formulated as a tablet, which may optionally contain one or more other compounds useful for treating HIV. In certain embodiments, the tablet can contain another active ingredient for treating HIV, such as HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, pharmacokinetic enhancers, and combinations thereof.

In certain embodiments, such tablets are suitable for once daily dosing.

HIV Combination Therapy

In some embodiments, the invention provides a method for preventing or treating an HIV infection, comprising administering to a patient in need thereof a therapeutically effective amount of a compound disclosed herein (e.g., Formula I Form I and/or Formula I Form II) or a pharmaceutically acceptable salt thereof, in combination with a therapeutically effective amount of one or more additional therapeutic agents.

In the above embodiments, the additional therapeutic agent may be an anti-HIV agent. HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, latency reversing agents, compounds that target the HIV capsid, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, HIV vaccines, and combinations thereof.

In some embodiments, the additional therapeutic agent is selected from immunomodulators, immunotherapeutic agents, antibody-drug conjugates, gene modifiers, gene editors (such as CRISPR/Cas9, zinc finger nucleases, homing nucleases, synthetic nucleases, TALENs), and cell therapies such as chimeric antigen receptor T-cell, CAR-T (e.g., YESCARTA® (axicabtagene ciloleucel)), and engineered T cell receptors, TCR-T.

In some embodiments, the additional therapeutic agent is selected from the group consisting of combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, and combinations thereof.

In one particular embodiment, the additional therapeutic agent is selected from the group consisting of HIV protease inhibitors, HIV reverse transcriptase inhibitors, HIV integrase inhibitors, and combinations thereof.

HIV Combination Drugs

Examples of combination drugs include ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); darunavir, tenofovir alafenamide hemifumarate, emtricitabine, and cobicistat; efavirenz, lamivudine, and tenofovir disoproxil fumarate; lamivudine and tenofovir disoproxil fumarate; tenofovir and lamivudine; tenofovir alafenamide and emtricitabine; tenofovir alafenamide hemifumarate and emtricitabine; tenofovir alafenamide hemifumarate, emtricitabine, and rilpivirine; tenofovir alafenamide hemifumarate, emtricitabine, cobicistat, and elvitegravir; COMBIVIR® (zidovudine and lamivudine; AZT+3TC); EPZICOM® (LIVEXA®; abacavir sulfate and lamivudine; ABC+3TC); KALETRA® (ALUVIA®; lopinavir and ritonavir); TRIUMEQ® (dolutegravir, abacavir, and lamivudine); TRIZIVIR® (abacavir sulfate, zidovudine, and lamivudine; ABC+AZT+3TC); atazanavir and cobicistat; atazanavir sulfate and cobicistat; atazanavir sulfate and ritonavir; darunavir and cobicistat; dolutegravir and rilpivirine; dolutegravir and rilpivirine hydrochloride; dolutegravir, abacavir sulfate, and lamivudine; lamivudine, nevirapine, and zidovudine; raltegravir and lamivudine; doravirine, lamivudine, and tenofovir disoproxil fumarate; doravirine, lamivudine, and tenofovir disoproxil; dolutegravir+lamivudine, lamivudine+abacavir+zidovudine, lamivudine+abacavir, lamivudine+tenofovir disoproxil fumarate, lamivudine+zidovudine+nevirapine, lopinavir+ritonavir, lopinavir+ritonavir+abacavir+lamivudine, lopinavir+ritonavir+zidovudine+lamivudine, tenofovir+lamivudine, and tenofovir disoproxil fumarate+emtricitabine+rilpivirine hydrochloride, lopinavir, ritonavir, zidovudine and lamivudine; Vacc-4x and romidepsin; and APH-0812.

Other HIV Drugs

Examples of other drugs for treating HIV include acemannan, alisporivir, BanLec, deferiprone, Gamimune, metenkefalin, naltrexone, Prolastin, REP 9, RPI-MN, VSSP, Hlviral, SB-728-T, 1,5-dicaffeoylquinic acid, rHIV 7-shl-TAR-CCR5RZ, AAV-eCD4-Ig gene therapy, MazF gene therapy, BlockAide, ABX-464, AG-1105, APH-0812, BIT-225, CYT-107, HGTV-43, HPH-116, HS-10234, IMO-3100, IND-02, MK-1376, MK-8507, MK-8591, NOV-205, PA-1050040 (PA-040), PGN-007, SCY-635, SB-9200, SCB-719, TR-452, TEV-90110, TEV-90112, TEV-90111, TEV-90113, RN-18, Immuglo, and VIR-576.

HIV Protease Inhibitors

Examples of HIV protease inhibitors include amprenavir, atazanavir, brecanavir, darunavir, fosamprenavir, fosamprenavir calcium, indinavir, indinavir sulfate, lopinavir, nelfinavir, nelfinavir mesylate, ritonavir, saquinavir, saquinavir mesylate, tipranavir, DG-17, TMB-657 (PPL-100), T-169, BL-008, and TMC-310911.

HIV Reverse Transcriptase Inhibitors

Examples of HIV non-nucleoside or non-nucleotide inhibitors of reverse transcriptase include dapivirine, delavirdine, delavirdine mesylate, doravirine, efavirenz, etravirine, lentinan, nevirapine, rilpivirine, ACC-007, AIC-292, KM-023, and VM-1500.

Examples of HIV nucleoside or nucleotide inhibitors of reverse transcriptase include adefovir, adefovir dipivoxil, azvudine, emtricitabine, tenofovir, tenofovir alafenamide, tenofovir alafenamide fumarate, tenofovir alafenamide hemifumarate, tenofovir disoproxil, tenofovir disoproxil fumarate, tenofovir disoproxil hemifumarate, VIDEX® and VIDEX EC® (didanosine, ddI), abacavir, abacavir sulfate, alovudine, apricitabine, censavudine, didanosine, elvucitabine, festinavir, fosalvudine tidoxil, CMX-157, dapivirine, doravirine, etravirine, OCR-5753, tenofovir disoproxil orotate, fozivudine tidoxil, lamivudine, phosphazid, stavudine, zalcitabine, zidovudine, GS-9131, GS-9148, and KP-1461.

HIV Integrase Inhibitors

Examples of HIV integrase inhibitors include elvitegravir, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, dolutegravir, JTK-351, bictegravir, AVX-15567, cabotegravir (long-acting injectable), diketo quinolin-4-1 derivatives, integrase-LEDGF inhibitor, ledgins, M-522, M-532, NSC-310217, NSC-371056, NSC-48240, NSC-642710, NSC-699171, NSC-699172, NSC-699173, NSC-699174, stilbenedisulfonic acid, T-169 and cabotegravir.

Examples of HIV non-catalytic site, or allosteric, integrase inhibitors (NCINI) include CX-05045, CX-05168, and CX-14442.

HIV Entry Inhibitors

Examples of HIV entry (fusion) inhibitors include cenicriviroc, CCR5 inhibitors, gp41 inhibitors, CD4 attachment inhibitors, gp120 inhibitors, and CXCR4 inhibitors.

Examples of CCR5 inhibitors include aplaviroc, vicriviroc, maraviroc, cenicriviroc, PRO-140, adaptavir (RAP-101), nifeviroc (TD-0232), anti-GP120/CD4 or CCR5 bispecific antibodies, B-07, MB-66, polypeptide C25P, TD-0680, and vMIP (Haimipu).

Examples of gp41 inhibitors include albuvirtide, enfuvirtide, BMS-986197, enfuvirtide biobetter, enfuvirtide biosimilar, HIV-1 fusion inhibitors (P26-Bapc), ITV-1, ITV-2, ITV-3, ITV-4, PIE-12 trimer and sifuvirtide.

Examples of CD4 attachment inhibitors include ibalizumab and CADA analogs.

Examples of gp120 inhibitors include Radha-108 (receptol) 3B3-PE38, BanLec, bentonite-based nanomedicine, fostemsavir tromethamine, IQP-0831, and BMS-663068

Examples of CXCR4 inhibitors include plerixafor, ALT-1188, N15 peptide, and vMIP (Haimipu).

HIV Maturation Inhibitors

Examples of HIV maturation inhibitors include BMS-955176 and GSK-2838232.

Latency Reversing Agents

Examples of latency reversing agents include histone deacetylase (HDAC) inhibitors, proteasome inhibitors such as velcade, protein kinase C (PKC) activators, Smyd2 inhibitors, BET-bromodomain 4 (BRD4) inhibitors, ionomycin, PMA, SAHA (suberanilohydroxamic acid, or suberoyl, anilide, and hydroxamic acid), AM-0015, ALT-803, NIZ-985, NKTR-255, IL-15 modulating antibodies, JQ1, disulfiram, amphotericin B, and ubiquitin inhibitors such as largazole analogs, and GSK-343.

Examples of HDAC inhibitors include romidepsin, vorinostat, and panobinostat.

Examples of PKC activators include indolactam, prostratin, ingenol B, and DAG-lactones.

Capsid Inhibitors

Examples of capsid inhibitors include HIV capsid polymerization inhibitors or HIV capsid disrupting compounds, HIV nucleocapsid p7 (NCp7) inhibitors such as azodicarbonamide, HIV p24 capsid protein inhibitors, AVI-621, AVI-101, AVI-201, AVI-301, and AVI-CAN1-15 series. In some embodiments, the capsid inhibitors are selected from the group consisting of:

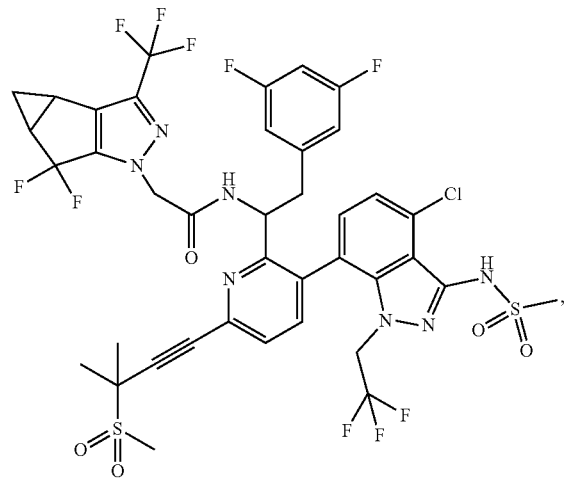

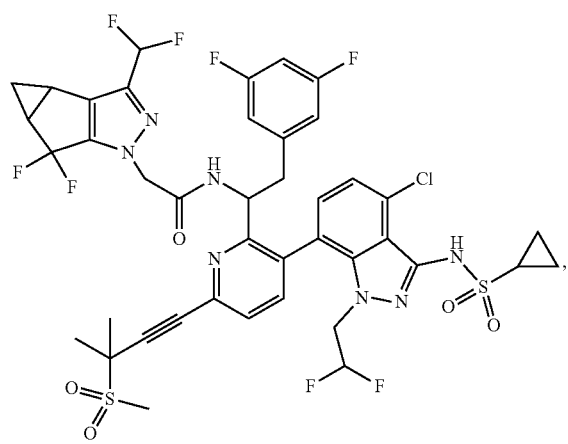 [SMILES: CC(C)(C#Cc1ccc(-c2ccc(Cl)c3c(NS(=O)(=O)C4CC4)nn(CC(F)F)c23)c([C@H](Cc2cc(F)cc(F)c2)NC(=O)Cn2nc(C(F)F)c3c2C(F)(F)[C@@H]2C[C@H]32)n1)S(C)(=O)=O]

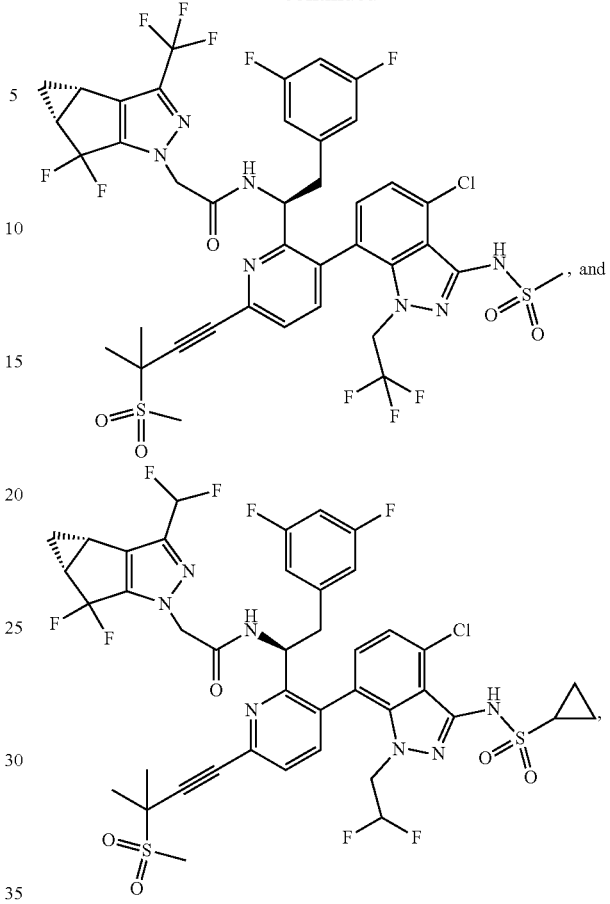

or a pharmaceutically acceptable salt thereof.

Immune-Based Therapies

Examples of immune-based therapies include toll-like receptors modulators such as tlr1, tlr2, tlr3, tlr4, tlr5, tlr6, tlr7, tlr8, tlr9, tlr10, tlr11, tlr12, and tlr13; programmed cell death protein 1 (Pd-1) modulators; programmed death-ligand 1 (Pd-L1) modulators; IL-15 modulators; DermaVir; interleukin-7; plaquenil (hydroxychloroquine); proleukin (aldesleukin, IL-2); interferon alfa; interferon alfa-2b; interferon alfa-n3; pegylated interferon alfa; interferon gamma; hydroxyurea; mycophenolate mofetil (MPA) and its ester derivative mycophenolate mofetil (MMF); ribavirin; rintatolimod, polymer polyethyleneimine (PEI); gepon; rintatolimod; IL-12; WF-10; VGV-1; MOR-22; BMS-936559; CYT-107, interleukin-15/Fc fusion protein, normferon, peginterferon alfa-2a, peginterferon alfa-2b, recombinant interleukin-15, RPI-MN, GS-9620, STING modulators, RIG-I modulators, NOD2 modulators, and IR-103.

Phosphatidylinositol 3-Kinase (PI3K) Inhibitors

Examples of PI3K inhibitors include idelalisib, alpelisib, buparlisib, CAI orotate, copanlisib, duvelisib, gedatolisib, neratinib, panulisib, perifosine, pictilisib, pilaralisib, puquitinib mesylate, rigosertib, rigosertib sodium, sonolisib, taselisib, AMG-319, AZD-8186, BAY-1082439, CLR-1401, CLR-457, CUDC-907, DS-7423, EN-3342, GSK-2126458, GSK-2269577, GSK-2636771, INCB-040093, LY-3023414, MLN-1117, PQR-309, RG-7666, RP-6530, RV-1729, SAR-245409, SAR-260301, SF-1126, TGR-1202, UCB-5857, VS-5584, XL-765, and ZSTK-474.

Alpha-4/Beta-7 Antagonists

Examples of Integrin alpha-4/beta-7 antagonists include PTG-100, TRK-170, abrilumab, etrolizumab, carotegrast methyl, and vedolizumab.

HIV Antibodies, Bispecific Antibodies, and "Antibody-like" Therapeutic Proteins

Examples of HIV antibodies, bispecific antibodies, and "antibody-like" therapeutic proteins include DARTs®, DUOBODIES®, BITES®, XmAbs®, TandAbs®, Fab derivatives, bnABs (broadly neutralizing HIV-1 antibodies), BMS-936559, TMB-360, and those targeting HIV gp120 or gp41, antibody-Recruiting Molecules targeting HIV, anti-CD63 monoclonal antibodies, anti-GB virus C antibodies, anti-GP120/CD4, CCR5 bispecific antibodies, anti-nef single domain antibodies, anti-Rev antibody, camelid derived anti-CD18 antibodies, camelid-derived anti-ICAM-1 antibodies, DCVax-001, gp140 targeted antibodies, gp41-based HIV therapeutic antibodies, human recombinant mAbs (PGT-121), ibalizumab, Immuglo, MB-66.

Examples of those targeting HIV in such a manner include bavituximab, UB-421, C2F5, 2G12, C4E10, C2F5+C2G12+C4E10, 8ANC195, 3BNC117, 10-1074, PGT145, PGT121, PGT-151, PGT-133, MDX010 (ipilimumab), DH511, N6, VRC01, PGDM1400, A32, 7B2, 10E8, VRC-07-523, VRC-HIV MAB080-00-AB, MGD-014 and VRC07.

Pharmacokinetic Enhancers

Examples of pharmacokinetic enhancers include cobicistat and ritonavir.

Additional Therapeutic Agents

Examples of additional therapeutic agents include the compounds disclosed in WO 2004/096286 (Gilead Sciences), WO 2006/015261 (Gilead Sciences), WO 2006/110157 (Gilead Sciences), WO 2012/003497 (Gilead Sciences), WO 2012/003498 (Gilead Sciences), WO 2012/145728 (Gilead Sciences), WO 2013/006738 (Gilead Sciences), WO 2013/159064 (Gilead Sciences), WO 2014/100323 (Gilead Sciences), US 2013/0165489 (University of Pennsylvania), US 2014/0221378 (Japan Tobacco), US 2014/0221380 (Japan Tobacco), WO 2009/062285 (Boehringer Ingelheim), WO 2010/130034 (Boehringer Ingelheim), WO 2013/006792 (Pharma Resources), US 20140221356 (Gilead Sciences), US 20100143301 (Gilead Sciences) and WO 2013/091096 (Boehringer Ingelheim).

HIV Vaccines

Examples of HIV vaccines include peptide vaccines, recombinant subunit protein vaccines, live vector vaccines, DNA vaccines, CD4-derived peptide vaccines, vaccine combinations, rgp120 (AIDSVAX), ALVAC HIV (vCP1521)/AIDSVAX B/E (gp120) (RV144), monomeric gp120 HIV-1 subtype C vaccine, Remune, ITV-1, Contre Vir, Ad5-ENVA-48, DCVax-001 (CDX-2401), Vacc-4x, Vacc-C5, VAC-3S, multiclade DNA recombinant adenovirus-5 (rAd5), Pennvax-GS Pennvax-GP, HIV-TriMix-mRNA vaccine, HIV-LAMP-vax, Ad35, Ad35-GRIN, NAcGM3/VSSP ISA-51, poly-ICLC adjuvanted vaccines, TatImmune, GTU-multi-HIV (FIT-06), gp140[delta]V2.TV1+MF-59, rVSVIN HIV-1 gag vaccine, SeV-Gag vaccine, AT-20, DNK-4, ad35-Grin/ENV, TBC-M4, HIV AX, HIV AX-2, NYVAC-HIV-PT1, NYVAC-HIV-PT4, DNA-HIV-PT123, rAAV1-PG9DP, GOVX-B11, GOVX-B21, TVI-HIV-1, Ad-4 (Ad4-env Clade C+Ad4-mGag), EN41-UGR7C, EN41-FPA2, PreVaxTat, AE-H, MYM-V101, CombiHIV vac, ADVAX, MYM-V201, MVA-CMDR, DNA-Ad5 gag/pol/nef/nev (HVTN505), MVATG-17401, ETV-01, CDX-1401, rcAD26.MOS1.HIV-Env, Ad26.Mod.HIV vaccine, AGS-004, AVX-101, AVX-201, PEP-6409, SAV-001, ThV-01, TL-01, TUTI-16, VGX-3300, IHV-001, and virus-like particle vaccines such as pseudovirion vaccine, CombiVICHvac, LFn-p24 B/C fusion vaccine, GTU-based DNA vaccine, HIV gag/pol/nef/env DNA vaccine, anti-TAT HIV vaccine, conjugate polypeptides vaccine, dendritic-cell vaccines, gag-based DNA vaccine, GI-2010, gp41 HIV-1 vaccine, HIV vaccine (PIKA adjuvant), I i-key/MHC class II epitope hybrid peptide vaccines, ITV-2, ITV-3, ITV-4, LIPO-5, multiclade Env vaccine, MVA vaccine, Pennvax-GP, pp71-deficient HCMV vector HIV gag vaccine, recombinant peptide vaccine (HIV infection), NCI, rgp160 HIV vaccine, RNActive HIV vaccine, SCB-703, Tat Oyi vaccine, TBC-M4, therapeutic HIV vaccine, UBI HIV gp120, Vacc-4x+romidepsin, variant gp120 polypeptide vaccine, rAd5 gag-pol env A/B/C vaccine, DNA.HTI and MVA.HTI.

HIV Combination Therapy

In a particular embodiment, a compound disclosed herein, or a pharmaceutically acceptable salt thereof, is combined with one, two, three, four or more additional therapeutic agents selected from ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); adefovir; adefovir dipivoxil; cobicistat; emtricitabine; tenofovir; tenofovir disoproxil; tenofovir disoproxil fumarate; tenofovir alafenamide; tenofovir alafenamide hemifumarate; TRIUMEQ® (dolutegravir, abacavir, and lamivudine); dolutegravir, abacavir sulfate, and lamivudine; raltegravir; raltegravir and lamivudine; maraviroc; enfuvirtide; ALUVIA® (KALETRA®; lopinavir and ritonavir); COMBIVIR® (zidovudine and lamivudine; AZT+3TC); EPZICOM® (LIVEXA®; abacavir sulfate and lamivudine; ABC+3TC); TRIZIVIR® (abacavir sulfate, zidovudine, and lamivudine; ABC+AZT+3TC); rilpivirine; rilpivirine hydrochloride; atazanavir sulfate and cobicistat; atazanavir and cobicistat; darunavir and cobicistat; atazanavir; atazanavir sulfate; dolutegravir; elvitegravir; ritonavir; atazanavir sulfate and ritonavir; darunavir; lamivudine; prolastin; fosamprenavir; fosamprenavir calcium efavirenz; etravirine; nelfinavir; nelfinavir mesylate; interferon; didanosine; stavudine; indinavir; indinavir sulfate; tenofovir and lamivudine; zidovudine; nevirapine; saquinavir; saquinavir mesylate; aldesleukin; zalcitabine; tipranavir; amprenavir; delavirdine; delavirdine mesylate; Radha-108 (receptol); lamivudine and tenofovir disoproxil fumarate; efavirenz, lamivudine, and tenofovir disoproxil fumarate; phosphazid; lamivudine, nevirapine, and zidovudine; abacavir; and abacavir sulfate.

It will be appreciated by one of skill in the art that the additional therapeutic agents listed above may be included in more than one of the classes listed above. The particular classes are not intended to limit the functionality of those compounds listed in those classes.

In a specific embodiment, a compound disclosed herein, or a pharmaceutically acceptable salt thereof, is combined with an HIV nucleoside or nucleotide inhibitor of reverse transcriptase and an HIV non-nucleoside inhibitor of reverse transcriptase. In another specific embodiment, a compound disclosed herein, or a pharmaceutically acceptable salt thereof, is combined with an HIV nucleoside or nucleotide inhibitor of reverse transcriptase, and an HIV protease inhibiting compound. In an additional embodiment, a compound disclosed herein, or a pharmaceutically acceptable salt thereof, is combined with an HIV nucleoside or nucleotide inhibitor of reverse transcriptase, an HIV non-nucleoside inhibitor of reverse transcriptase, and a pharmacokinetic enhancer. In certain embodiments, a compound disclosed herein, or a pharmaceutically acceptable salt thereof, is combined with at least one HIV nucleoside inhibitor of reverse transcriptase, an integrase inhibitor, and a pharmacokinetic enhancer. In another embodiment, a compound disclosed herein, or a pharmaceutically acceptable salt thereof, is combined with two HIV nucleoside or nucleotide inhibitors of reverse transcriptase.

In a particular embodiment, a compound disclosed herein, or a pharmaceutically acceptable salt thereof, is combined with abacavir sulfate, tenofovir, tenofovir disoproxil, tenofovir disoproxil fumarate, tenofovir disoproxil hemifumarate, tenofovir alafenamide, or tenofovir alafenamide hemifumarate.

In a particular embodiment, a compound disclosed herein, or a pharmaceutically acceptable salt thereof, is combined with tenofovir, tenofovir disoproxil, tenofovir disoproxil fumarate, tenofovir alafenamide, or tenofovir alafenamide hemifumarate.

In a particular embodiment, a compound disclosed herein, or a pharmaceutically acceptable salt thereof, is combined with a first additional therapeutic agent selected from the group consisting of abacavir sulfate, tenofovir, tenofovir disoproxil, tenofovir disoproxil fumarate, tenofovir alafenamide, and tenofovir alafenamide hemifumarate, and a second additional therapeutic agent selected from the group consisting of emtricitabine and lamivudine.

In a particular embodiment, a compound disclosed herein, or a pharmaceutically acceptable salt thereof, is combined with a first additional therapeutic agent selected from the group consisting of tenofovir, tenofovir disoproxil, tenofovir disoproxil fumarate, tenofovir alafenamide, and tenofovir alafenamide hemifumarate, and a second additional therapeutic agent, wherein the second additional therapeutic agent is emtricitabine.

A compound as disclosed herein (e.g., any compound of Formula (I)) may be combined with one or more additional therapeutic agents in any dosage amount of the compound of Formula (I) (e.g., from 1 mg to 500 mg of compound).

In certain embodiments, a compound disclosed herein, or a pharmaceutically acceptable salt thereof, is combined with 5-30 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 5-10, 5-15, 5-20, 5-25, 25-30, 20-30, 15-30, or 10-30 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 10 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 25 mg tenofovir alafenamide fumarate, tenofovir alafenamide hemifumarate, or tenofovir alafenamide, and 200 mg emtricitabine. A compound as disclosed herein (e.g., a compound of formula (I)) may be combined with the agents provided herein in any dosage amount of the compound (e.g., from 1 mg to 500 mg of compound) the same as if each combination of dosages were specifically and individually listed.

In certain embodiments, a compound disclosed herein, or a pharmaceutically acceptable salt thereof, is combined with 200-400 mg tenofovir disoproxil fumarate, tenofovir disoproxil hemifumarate, or tenofovir disoproxil, and 200 mg emtricitabine. In certain embodiments, a compound disclosed herein, or a pharmaceutically acceptable salt thereof, is combined with 200-250, 200-300, 200-350, 250-350, 250-400, 350-400, 300-400, or 250-400 mg tenofovir disoproxil fumarate, tenofovir disoproxil hemifumarate, or tenofovir disoproxil, and 200 mg emtricitabine. In certain embodiments, a compound disclosed herein, or a pharmaceutically acceptable salt thereof, is combined with 300 mg tenofovir disoproxil fumarate, tenofovir disoproxil hemifumarate, or tenofovir disoproxil, and 200 mg emtricitabine. A compound as disclosed herein (e.g., a compound of formula (I)) may be combined with the agents provided herein in any dosage amount of the compound (e.g., from 1 mg to 500 mg of compound) the same as if each combination of dosages were specifically and individually listed.

In a specific embodiment, a compound disclosed herein, or a pharmaceutically acceptable salt thereof, is combined with an HIV integrase inhibitor. In another specific embodiment, a compound disclosed herein, or a pharmaceutically acceptable salt thereof, is combined with an HIV protease inhibitor. In an additional embodiment, a compound disclosed herein, or a pharmaceutically acceptable salt thereof, is combined with HIV protease inhibitor and a pharmacokinetic enhancer. In certain embodiments, a compound disclosed herein, or a pharmaceutically acceptable salt thereof, is combined with an HIV integrase inhibitor and an HIV protease inhibitor.

XRPD Data

In certain embodiments, the crystalline forms are characterized by the interlattice plane intervals determined by an X-ray powder diffraction pattern (XRPD). The diffractogram of XRPD is typically represented by a diagram plotting the intensity of the peaks versus the location of the peaks, i.e., diffraction angle 2θ (two-theta) in degrees. The characteristic peaks of a given XRPD can be selected according to the peak locations and their relative intensity to conveniently distinguish this crystalline structure from others.

XRPD patterns were collected on a PANanalytical XPERT-PRO diffractometer at ambient conditions under the following experimental settings: 45 KV; 40 mA, Kul=1.5406 Å; scan range 2 to 400; step size 0.0084 or 0.0167°; measurement time: 5 minutes. XRPD patterns were collected at ambient temperatures.

Those skilled in the art recognize that the measurements of the XRPD peak locations and/or intensity for a given crystalline form of the same compound will vary within a margin of error. The values of degree 2θ allow appropriate error margins. Typically, the error margins are represented by "+". For example, the degree 2θ of about "8.7±0.3" denotes a range from about 8.7±0.3, i.e., about 9.0, to about 8.7-0.3, i.e., about 8.4. Depending on the sample preparation techniques, the calibration techniques applied to the instruments, human operational variation, and etc., those skilled in the art recognize that the appropriate error of margins for a XRPD can be +0.5; +0.4; +0.3; +0.2; +0.1; +0.05; or less. In certain embodiments, the XRPD margin of error is +0.05. In certain embodiments, the XRPD margin of error is +0.1. In certain embodiments, the XRPD margin of error is +0.2. In certain embodiments, the XRPD margin of error is +0.5.

Additional details of the methods and equipment used for the XRPD analysis are described in the Examples section.

The XRPD peaks for crystalline Formula I Form I are shown below in Table 1A.

TABLE 1A

XRPD peaks for crystalline Formula I Form I

Formula I Form I

| Peak Position [°2θ] | Relative Intensity [%] |
|---|---|
| 7.7 | 20 |
| 11.2 | 37 |
| 11.5 | 18 |
| 12.0 | 5 |
| 12.9 | 19 |
| 15.2 | 20 |
| 16.5 | 15 |
| 18.5 | 60 |
| 18.7 | 21 |
| 20.3 | 100 |
| 21.4 | 79 |
| 21.8 | 32 |
| 22.3 | 26 |
| 22.6 | 10 |
| 22.8 | 29 |
| 23.8 | 13 |
| 24.6 | 34 |
| 24.9 | 8 |
| 25.2 | 14 |
| 25.7 | 17 |
| 26.1 | 20 |
| 26.8 | 22 |
| 27.6 | 12 |
| 28.0 | 9 |
| 28.8 | 6 |
| 29.3 | 11 |
| 31.2 | 6 |
| 32.5 | 5 |
| 33.0 | 6 |
| 33.3 | 7 |
| 34.2 | 6 |
| 35.8 | 6 |

The XRPD peaks for crystalline Formula I Form II are shown below in Table 1B.

TABLE 1B

XRPD peaks for crystalline Formula I Form II

Formula I Form II

| Peak Position [°2θ] | Relative Intensity [%] |
|---|---|
| 5.6 | 17 |
| 10.2 | 8 |
| 11.2 | 25 |
| 11.5 | 6 |
| 12.2 | 15 |
| 12.8 | 18 |
| 13.1 | 43 |
| 13.5 | 13 |
| 15.0 | 11 |
| 16.8 | 8 |
| 17.1 | 18 |
| 17.3 | 6 |
| 18.1 | 37 |
| 18.6 | 25 |
| 19.2 | 30 |
| 20.4 | 12 |
| 20.7 | 41 |
| 21.6 | 9 |
| 21.8 | 15 |
| 22.4 | 100 |
| 22.9 | 34 |
| 26.3 | 11 |
| 26.6 | 10 |
| 26.9 | 8 |
| 27.1 | 5 |
| 28.1 | 24 |
| 30.8 | 9 |

The XRPD peaks for crystalline Formula I Vanillate Form I are shown below in Table 1C.

TABLE 1C

XRPD peaks for crystalline Formula I Vanillate Form I

Formula I Vanillate Form I

| Peak Position [°2θ] | Relative Intensity [%] |
|---|---|
| 3.0 | 26 |
| 5.9 | 32 |
| 8.1 | 10 |
| 9.0 | 29 |
| 9.4 | 7 |
| 10.7 | 37 |
| 11.2 | 11 |
| 11.8 | 100 |
| 13.4 | 8 |
| 14.7 | 17 |
| 15.2 | 45 |
| 15.8 | 20 |
| 16.3 | 12 |
| 16.9 | 8 |
| 17.4 | 16 |
| 18.5 | 7 |
| 19.2 | 6 |
| 20.0 | 9 |
| 20.4 | 50 |
| 21.1 | 12 |
| 22.3 | 8 |
| 23.9 | 6 |
| 24.5 | 28 |
| 25.0 | 6 |
| 25.8 | 6 |
| 26.8 | 19 |
| 30.6 | 7 |
| 31.9 | 9 |

The XRPD peaks for crystalline Formula I Vanillate Form II are shown below in Table 1D.

TABLE 1D

XRPD peaks for crystalline Formula I Vanillate Form II

Formula I Vanillate Form II

| Peak Position [°2θ] | Relative Intensity [%] |
|---|---|
| 3.0 | 33 |
| 5.9 | 33 |
| 9.2 | 9 |
| 10.9 | 17 |
| 11.8 | 100 |

TABLE 1D-continued

XRPD peaks for crystalline Formula I Vanillate Form II
Formula I
Vanillate Form II

| Peak Position [°2θ] | Relative Intensity [%] |
|---|---|
| 14.7 | 19 |
| 15.5 | 25 |
| 18.6 | 8 |
| 19.3 | 16 |
| 20.1 | 9 |
| 20.8 | 18 |
| 24.2 | 7 |
| 24.4 | 20 |
| 26.7 | 7 |

The XRPD peaks for crystalline Formula I Phosphate Form I are shown below in Table 1E.

TABLE 1E

XRPD peaks for crystalline Formula I Phosphate Form I
Formula I
Phosphate Form I

| Peak Position [°2θ] | Relative Intensity [%] |
|---|---|
| 2.1 | 20 |
| 3.3 | 50 |
| 5.6 | 36 |
| 7.7 | 23 |
| 9.3 | 29 |
| 11.2 | 29 |
| 12.9 | 46 |
| 13.2 | 73 |
| 13.7 | 38 |
| 14.0 | 51 |
| 16.0 | 77 |
| 16.3 | 14 |
| 16.7 | 73 |
| 17.1 | 36 |
| 17.6 | 23 |
| 17.8 | 23 |
| 18.5 | 100 |
| 18.9 | 61 |
| 19.9 | 26 |
| 20.3 | 53 |
| 21.4 | 18 |
| 22.1 | 49 |
| 22.4 | 74 |
| 22.7 | 64 |
| 23.2 | 14 |
| 23.5 | 17 |
| 24.5 | 38 |
| 26.0 | 16 |
| 27.0 | 49 |
| 31.0 | 15 |

The XRPD peaks for crystalline Formula I Xinafoate Form I are shown below in Table 1F.

TABLE 1F

XRPD peaks for crystalline Formula I Xinafoate Form I
Formula I
Xinafoate Form I

| Peak Position [°2θ] | Relative Intensity [%] |
|---|---|
| 6.9 | 27 |
| 9.8 | 5 |
| 10.2 | 11 |
| 11.1 | 5 |
| 12.4 | 17 |
| 13.8 | 7 |
| 15.1 | 40 |
| 15.8 | 8 |
| 16.6 | 7 |
| 17.2 | 21 |
| 18.0 | 21 |
| 18.8 | 8 |
| 19.0 | 14 |
| 20.5 | 8 |
| 22.3 | 7 |
| 23.6 | 22 |
| 24.2 | 6 |
| 24.8 | 100 |
| 26.0 | 5 |
| 30.4 | 7 |

The XRPD peaks for crystalline Formula I Phosphate Acetonitrile Solvate Form I are shown below in Table 1G

TABLE 1G

XRPD peaks for crystalline Formula I Phosphate Acetonitrile Solvate Form I
Formula I
Phosphate Acetonitrile Solvate Form I

| Peak Position [°2θ] | Relative Intensity [%] |
|---|---|
| 2.4 | 10 |
| 3.0 | 68 |
| 4.9 | 29 |
| 5.8 | 9 |
| 6.7 | 22 |
| 8.7 | 16 |
| 9.0 | 19 |
| 10.5 | 13 |
| 11.3 | 33 |
| 11.6 | 22 |
| 13.2 | 52 |
| 14.4 | 35 |
| 16.0 | 43 |
| 17.8 | 49 |
| 18.0 | 26 |
| 18.5 | 100 |
| 18.8 | 59 |
| 20.0 | 98 |
| 21.1 | 34 |
| 21.7 | 43 |
| 22.2 | 43 |
| 22.7 | 62 |
| 23.3 | 22 |
| 24.6 | 28 |
| 25.8 | 13 |
| 27.0 | 12 |
| 34.6 | 13 |

Preparation of Crystalline Forms

One method of synthesizing ethyl ((S)-(((((2R,5R)-5-(6-amino-9H-purin-9-yl)-4-fluoro-2,5-dihydrofuran-2-yl)oxy)

methyl)(phenoxy)phosphoryl)-L-alaninate (e.g. Formula I) has been previously described in U.S. Pat. No. 7,871,991, filed Jul. 26, 2005. This reference is hereby incorporated herein by reference in its entirety, and specifically with respect to the synthesis of ethyl ((S)-((((2R,5R)-5-(6-amino-9H-purin-9-yl)-4-fluoro-2,5-dihydrofuran-2-yl)oxy)methyl)(phenoxy)phosphoryl)-L-alaninate. Another method of synthesizing ethyl ((S)-((((2R,5R)-5-(6-amino-9H-purin-9-yl)-4-fluoro-2,5-dihydrofuran-2-yl)oxy)methyl)(phenoxy)phosphoryl)-L-alaninate has been previously described in U.S. Pat. No. 8,987,437, filed May 18, 2012. This reference is hereby incorporated herein by reference in its entirety.

For example, in one aspect, provided is a method of producing a composition comprising one or more crystalline forms of Formula I, wherein the method comprises combining a compound of Formula I with a suitable solvent or a mixture of suitable solvents to produce a composition comprising one or more crystalline forms of the compound of Formula I. In another aspect, provided is another method of producing a composition comprising one or more crystalline forms of Formula I, wherein the method comprises combining Formula I with a suitable solvent or a mixture of suitable solvents.

The choice of a particular solvent or combination of solvents or method of combining solvents affects the formation favoring one crystalline form of Formula I over another. Solvents suitable for crystal formation may include, for example: diisopropyl ether, water, isopropyl alcohol, methyl isobutyl ketone, isopropyl acetate, ethyl acetate, methyl tert-butyl ether, toluene, ethanol, n-heptane, acetone, methyl ethyl ketone, 2-methyltetrahydrofuran, acetonitrile, isopropyl ether, and any mixture thereof.

The presence of impurities may affect the formation favoring one crystalline form of Formula I over another. In some embodiments, the form is prepared by a process comprising Formula I having impurities. In another embodiment, the form is prepared by a process comprising substantially pure Formula I.

In another aspect, provided is also one or more crystalline forms of Formula I produced according to any of the methods described herein.

It should be understood that the methods for preparing the crystalline forms described herein may yield quantity and quality differences compared to the methods for preparing a compound of Formula I produced on laboratory scale.

Formula I Form I

In some embodiments, provided is a method of producing a composition comprising crystalline Formula I Form I, wherein the method comprises combining Formula I (e.g., amorphous Formula I) with a solvent to produce a composition comprising crystalline Formula I Form I. In some embodiments, the solvent is selected from diisopropyl ether, water, isopropyl alcohol, methyl isobutyl ketone, isopropyl acetate, ethyl acetate, methyl tert-butyl ether, toluene, ethanol, n-heptane, acetone, methyl ethyl ketone, 2-methyltetrahydrofuran, acetonitrile, or isopropyl ether, or any mixture thereof. In some embodiments, the solvent is selected from a mixed solvent system consisting of ethanol/n-heptane, acetone/n-heptane, methyl tert-butyl ether/n-heptane, 2-methyltetrahydrofuran/n-heptane, and acetonitrile/isopropyl ether.

In some embodiments, provided is a method of producing a composition comprising crystalline Formula I Form I, wherein the method comprises combining Formula I with a solvent to produce a composition comprising crystalline Formula I Form I, wherein the solvent is acetonitrile and isopropyl ether. In some embodiments, the ratio of acetonitrile and isopropyl ether is about 1:1. In some embodiments, the method comprises combining acetonitrile and isopropyl ether with the seeds of crystalline Formula I Form I.

Formula I Form II

In some embodiments, provided herein is a method of producing a composition comprising crystalline Formula I Form II, wherein the method comprises combining Formula I (e.g., amorphous Formula I and/or Formula I, Form I) with a solvent to produce a composition comprising crystalline Formula I Form II. In some embodiments, the solvent is isopropyl acetate. In various embodiments, toluene is added to a mixture of Formula I Form I and isopropyl acetate. In some embodiments, the method comprises combining the seeds of crystalline Formula I Form I to a solution of Formula I in a solvent (e.g., isopropyl acetate) to produce crystalline Formula I Form II. In some embodiments, the method comprises combining the seeds of crystalline Formula I Form II to a solution of Formula I in a solvent to produce crystalline Formula I Form II.

Formula I Vanillate Form I

In some embodiments, provided herein is a method of producing a composition comprising crystalline Formula I Vanillate Form I, wherein the method comprises combining Formula I with vanillic acid and a solvent to produce a composition comprising crystalline Formula I Vanillate Form I. In some embodiments, the solvent is acetonitrile.

Formula I Vanillate Form II

In some embodiments, provided herein is a method of producing a composition comprising crystalline Formula I Vanillate Form II, wherein the method comprises combining a solution of vanillic acid (e.g., in an acetonitrile/THF solvent system) and a solution Formula I (e.g., in acetonitrile) to produce a composition comprising crystalline Formula I Vanillate Form II. In some embodiments, the mixture may be seeded with Formula I Vanillate Form I.

Formula I Phosphate Form I

In some embodiments, provided is a method of producing a composition comprising crystalline Formula I Phosphate Form I, wherein the method comprises combining Formula I with phosphoric acid and a solvent to produce a composition comprising crystalline Formula I Phosphate Form I. In some embodiments, the solvent is acetonitrile.

Formula I Xinafoate Form I

In some embodiments, provided herein is a method of producing a composition comprising crystalline Formula I Xinafoate Form I, wherein the method comprises combining Formula I with xinafoic acid (i.e., 1-hydroxy-2-naphthoic acid) and a solvent to produce a composition comprising crystalline Formula I Xinafoate Form I. In some embodiments, the solvent is acetonitrile.

Formula I Phosphate Acetonitrile Solvate Form I

In some embodiments, provided herein is a method of producing a composition comprising crystalline Formula I Phosphate Acetonitrile Solvate Form I, wherein the method comprises combining Formula I with phosphoric acid and a solvent to produce a composition comprising crystalline Formula I Phosphate Acetonitrile Solvate Form I. In some embodiments, the solvent is acetonitrile.

Uses in Manufacturing of Drug Product

In some embodiments, also provided is a use of the crystalline forms described herein in the manufacture of a drug product. The one or more of the crystalline forms described herein (e.g., the compounds of Formula I described herein) may be used in the manufacturing process to produce the drug product. The one or more of the crystalline forms described herein (e.g., the compounds of Formula I described herein) may be used as an intermediate in the manufacturing process to produce the drug product.

In some embodiments, crystalline compounds of Formula I are used in the manufacture of an active pharmaceutical ingredient. In some embodiments, Formula I Form I is used in the manufacture of an active pharmaceutical ingredient. In some embodiments, Formula I Form II is used in the manufacture of an active pharmaceutical ingredient. In some embodiments, Formula I Vanillate Form I is used in the manufacture of an active pharmaceutical ingredient. In some embodiments, Formula I Vanillate Form II is used in the manufacture of an active pharmaceutical ingredient. In some embodiments, Formula I Phosphate Form I is used in the manufacture of an active pharmaceutical ingredient. In some embodiments, Formula I Xinafoate Form I is used in the manufacture of an active pharmaceutical ingredient. In some embodiments, Formula I Phosphate Acetonitrile Solvate Form I is used in the manufacture of an active pharmaceutical ingredient. In some embodiments, amorphous Formula I, or a pharmaceutically acceptable salt, co-crystal, or solvate thereof, is used in the manufacture of an active pharmaceutical ingredient.

Articles of Manufacture and Kits

Compositions comprising one or more of the crystalline forms described herein (e.g., a compound of Formula I described herein) and formulated in one or more pharmaceutically acceptable excipients or other ingredients can be prepared, placed in an appropriate container, and labeled for treatment of an indicated condition, such as HIV. Accordingly, there also is contemplated an article of manufacture, such as a container comprising a dosage form of one or more of the crystalline forms described herein and a label containing instructions for use of the compound(s).

In some embodiments, the article of manufacture is a container comprising a dosage form of one or more of the crystalline forms described herein, and one or more pharmaceutically acceptable excipients or other ingredients. In some embodiments of the articles of manufacture described herein, the dosage form is a solution.

Kits also are contemplated. For example, a kit can comprise a dosage form of a pharmaceutical composition and a package insert containing instructions for use of the composition in treatment of a medical condition. In another embodiment a kit may comprise multiple individual dosage forms, each comprising a therapeutically effective amount of a compound as described herein, and instructions for their administration to a human in need thereof. Each of the individual dosage forms may comprise a therapeutically effective amount of a compound as described herein in combination with at least one pharmaceutically effective excipient. The individual dosage forms may be in the form of, as examples, a solution, a tablet, a pill, a capsule, a sachet, a sublingual medicament, a lyophilized powder, a spray-dried powder, or a liquid composition for oral, parenteral, or topical administration. The instructions for use in the kit may be for treating an HIV virus infection. The instructions may be directed to any of the viral infections and methods described herein. The instructions may be for prophylaxis or the treatment of an existing viral infection.

In some embodiments, a kit comprising: a tablet comprising a compound of Formula I (or a pharmaceutically acceptable salt or solvate thereof), a compound of Formula II (or a pharmaceutically acceptable salt thereof), cobicistat (or a pharmaceutically acceptable salt thereof), and darunavir (or a pharmaceutically acceptable salt or solvate thereof). In some embodiments, the kit further comprises a desiccant (e.g. silica gel).

In certain embodiments, the crystalline, salt, and/or solvate forms described herein may potentially exhibit improved properties. For example, in certain embodiments, the crystalline and/or salt forms described herein may potentially exhibit improved stability. Such improved stability could have a potentially beneficial impact on the manufacture of the compound of Formula I, such as for example offering the ability to store process intermediate for extended periods of time. Improved stability could also potentially benefit a composition or pharmaceutical composition of the compound of Formula I. In certain embodiments, the crystalline salt, and/or solvate forms described herein may also potentially result in improved yield of the compound of Formula I, or in an improvement of the quality of the compound of Formula I. In certain embodiments, the crystalline, salt, and/or solvate forms described herein may also exhibit improved pharmacokinetic properties and/or potentially improved bioavailability.

Methods

Formula I Form I

Amorphous Formula I (about 100 mg) in about 10 volume diisopropyl ether was stirred by a magnetic stir bar for about 16 h to 18 h at about 22° C. A crystalline slurry was formed and the solids were isolated by filtration and dried at about 50° C. under vacuum. Formula I Form I was characterized as discussed herein.

In alternative methods, Formula I Form I can be obtained by slurrying amorphous Formula I (about 100-200 mg) in a solvent (about 1 mL) with seeds of Formula I, Form I. In some embodiments, the solvent can be, for example, water, isopropyl alcohol, methyl isobutyl ketone, isopropyl acetate, ethyl acetate, methyl tert-butyl ether, or toluene. In various embodiments, the solvent can be a mixed solvent system such as ethanol/n-heptane, acetone/n-heptane, methyl ethyl ketone/n-heptane, 2-methyltetrahydrofuran/n-heptane, or acetonitrile/isopropyl ether.

In some embodiments, the seeds of Formula I, Form I that are used in this procedure can be prepared from amorphous Formula I according to the method above (i.e., stirring amorphous Formula I in diisopropyl ether for about 16 h to 18 h to form solids that were isolated by filtration and dried under vacuum).

Formula I Form II

A solution of Formula I (22.7 g) in isopropyl acetate (210 mL) was seeded with Formula I Form I (about 60 mg). The mixture was stirred at about 20° C. for about 12 h to form a slurry. The slurry was then heated to about 35° C. for about 30 minutes, and toluene (150 mL) was then added over about 30 min. The resulting mixture was stirred at about 20° C. for about 5 hours. The solids were then filtered and rinsed with isopropyl acetate/toluene (about 1:1, 150 mL), and dried at about 40° C. for about 16 h to 18 h under vacuum to afford a dry cake of Formula I Form II. Formula I Form II was characterized as discussed herein.

A solution of Formula I (about 4.0 g) in ethyl acetate (210 mL) was seeded with Formula I Form II (about 20 mg). The mixture was stirred at about 50° C. for about 4 h to form a slurry. The slurry was then cooled to about 20° C. over about 5 hours and held at about 20° C. for about 10 hours. Toluene (about 60 mL) was then added over about 60 min. The resulting mixture was stirred at about 20° C. for about 28 hours. The solids were then filtered and rinsed with ethyl acetate/toluene (about 1:1, 30 mL), and dried at about 40° C. for about 16 h to 18 h under vacuum to afford a dry cake of Formula I Form II. Formula I Form II was characterized as discussed herein.

In some embodiments, the seeds of Formula I Form II can be prepared in procedures similar to those as described herein Formula I Vanillate Form I A mixture of Formula I (108 mg) and 1.1 equivalents of vanillic acid (40 mg) was slurried in acetonitrile (about 2 mL) at about 50° C. for about 5 minutes, and then at room temperature for about 4 days. The resulting solids were isolated by filtration and were dried under vacuum at room temperature to afford Formula I Vanillate Form I, which was characterized as discussed herein.

Formula I Vanillate Form II

A solution of vanillic acid (1.06 g) in acetonitrile/tetrahydrofuran (10 mL, 1:1 v:v) was charged into a solution of Formula I (2.9 g) in acetonitrile (40 mL). The mixture was seeded with Formula I Vanillate Form I (5 mg), stirred about 16 h to 18 h filtered and dried on vacuum to afford a mixture of Formula I Vanillate Form I and Formula I Vanillate Form II.

A mixture of Formula I Vanillate Form I and Formula I Vanillate Form II (0.8 g) was slurried in acetonitrile (8 mL) at about 50° C. for about 1 hour, cooled to room temperature and stirred about 16 h to 18 h. The slurry was filtered and the resulting solids were dried under vacuum at about 50° C. to afford Formula I Vanillate Form II, which was characterized as discussed herein.

In some embodiments, the seeds of Formula I Vanillate Form I used in this procedure can be prepared by stirring amorphous Formula I in diisopropyl ether with a magnetic stir bar for about 16 h to 18 h at about 22° C. A crystalline slurry was formed and the solids were isolated by filtration and dried at about 50° C. under vacuum. Formula I Form I was characterized as discussed herein.

Formula I Phosphate Form I

Phosphoric acid (1.1 equivalents, about 30 mg of 85% aqueous phosphoric acid) was dissolved in acetonitrile (about 1 mL) and Formula I (111 mg) was added. The mixture was stirred at about 50° C. for about 5 minutes, and then at room temperature for about 4 days. The resulting solids were isolated by filtration and were dried under vacuum at room temperature to afford Formula I Phosphate Form I, which was characterized as discussed herein.

Formula I Xinafoate Form I

A mixture of Formula I (117 mg) and 1.1 equivalents of xinafoic acid (also called 1-hydroxy-2-naphthoic acid) (48 mg) was slurried in acetonitrile (about 2 mL) at about 50° C. for about 5 minutes. The mixture was then stirred at room temperature for about 4 days. The resulting solids were isolated by filtration and were dried under vacuum at room temperature to afford Formula I Xinafoate Form I, which was characterized as discussed herein.

Formula I Phosphate Acetonitrile Solvate Form I

Phosphoric acid (1.1 equivalents, about 30 mg of 85% aqueous phosphoric acid) was dissolved in acetonitrile (about 1 mL), followed by the addition of Formula I (111 mg) and stirring at about 50° C. for about 5 minutes. The reaction was then stirred at room temperature for about 4 days. The wet solids afforded an XRPD pattern that corresponded to a possible acetonitrile solvate of the Formula I Phosphate, which converted to Formula I Phosphate Form I after drying under vacuum at room temperature. A $^1$H NMR of Formula I Phosphate Acetonitrile Solvate Form I showed about 0.3 equivalent of acetonitrile after equilibration at ambient conditions. Formula I Phosphate Acetonitrile Solvate Form I was characterized as discussed herein.

The crystalline forms of the present invention were characterized by various analytical techniques, including X-ray powder diffraction (XRPD), differential scanning calorimetry (DSC), thermo-gravimetric analysis (TGA), and dynamic vapor sorption (DVS) using the procedures described below.

X-Ray Powder Diffraction (XRPD):

XRPD Patterns were Collected on a PANanalytical XPERT-PRO diffractometer at ambient conditions under the following experimental settings: 45 KV, 40 mA, Kα1=1.5406 Å, scan range 2 to 400, step size 0.0084 or 0.0167°, measurement time: 5 minutes.

The XRPD pattern for Formula I Form I is represented in FIG. 1.

The XRPD pattern for Formula I Form II is represented in FIG. 5.

The XRPD pattern for Formula I Vanillate Form I is represented in FIG. 9.

The XRPD pattern for Formula I Vanillate Form II is represented in FIG. 13.

The XRPD pattern for Formula I Phosphate Form I is represented in FIG. 17.

The XRPD pattern for Formula I Xinafoate Form I is represented in FIG. 20.

The XRPD pattern for Formula I Phosphate Acetonitrile Solvate Form I is represented in FIG. 23.

Differential Scanning Calorimetry (DSC):

DSC thermograms were collected on a TA Instruments Q2000 system equipped with a 50 position auto-sampler. The calibration for energy and temperature was carried out using certified indium. Typically 1 to 5 mg of each sample, in a pin-holed aluminum pan, was heated at 10° C./min from 25° C. to at least 200° C. A purge of dry nitrogen at 50 mL/min was maintained over the sample throughout the measurement. The onset of the melting endotherm was reported as the melting point.

The DSC thermogram for Formula I Form I is represented in FIG. 2.

The DSC thermogram for Formula I Form II is represented in FIG. 6.

The DSC thermogram for Formula I Vanillate Form I is represented in FIG. 10.

The DSC thermogram for Formula I Vanillate Form II is represented in FIG. 14.

The DSC thermogram for Formula I Phosphate Form I is represented in FIG. 18.

The DSC thermogram for Formula I Xinafoate Form I is represented in FIG. 21.

Thermo-Gravimetric Analysis (TGA):

TGA thermograms were collected on a TA Instruments Q5000 system, equipped with a 25 position auto-sampler. Typically 1 to 5 mg of each sample was loaded onto a pre-tared aluminium pan and heated at 10° C./min from 25° C. to 350° C. A nitrogen purge at 25 mL/min was maintained over the sample throughout the measurement.

The TGA thermogram for Formula I Form I is represented in FIG. 3.

The TGA thermogram for Formula I Form II is represented in FIG. 7.

The TGA thermogram for Formula I Vanillate Form I is represented in FIG. 11.

The TGA thermogram for Formula I Vanillate Form II is represented in FIG. 15.

The TGA thermogram for Formula I Phosphate Form I is represented in FIG. 19.

The TGA thermogram for Formula I Xinoafoate I is represented in FIG. 22.

Dynamic Vapor Sorption (DVS):

DVS data, which was used to determine the hygroscopicity of solids, was collected on a TA Instruments Q5000SA system. The temperature-controlled chamber was set at 25° C. and dry nitrogen was introduced at a flow rate of 10 mL/min. Approximately 1 to 5 mg of each sample was placed in a semispherical metal-coated quartz crucible or a disposable aluminum pan. A stepwise isotherm experiment at 25° C. was conducted by controlling the relative humidity (RH) in the chamber from 0% to 90%, then down to 0%, at 10% increments to accomplish a full sorption/desorption cycle.

The DVS isotherm for Formula I Form I is represented in FIG. 4.

The DVS isotherm for Formula I Form II is represented in FIG. 8.

The DVS isotherm for Formula I Vanillate Form I is represented in FIG. 12.

The DVS isotherm for Formula I Vanillate Form II is represented in FIG. 16.

Physicochemical Studies

The physicochemical properties for certain solid forms of the compound of Formula I described herein were examined. As shown in Table 2, Formula I Vanillate Form II, Formula I Form I, and Formula I Form II are less hygroscopic at 25° C. in comparison to the compound of Formula (Ia).

TABLE 2

Physicochemical properties for Certain Solid Forms of the Compound of Formula I

| Physicochemical Property | Formula I | | | |
| --- | --- | --- | --- | --- |
| | The compound of Formula (Ia) | Formula I Vanillate Form II | Formula I Form I | Formula I Form II |
| Melting point onset (° C.) | 150 | 151 | 101 | 121 |
| Hygroscopicity at 25° C. (% weight gain from 0 to 80% RH) | Slightly hygroscopic (0.6%) | Non-hygroscopic (0.15%) | Non-hygroscopic (0.06%) | Non-hygroscopic (0.14%) |
| Physical Stability* (stored at 40° C./ 75% RH open) | Stable up to at least 2 months | Stable up to at least 2 months | Stable up to at least 2 months | Stable up to at least 2 months |

*No form change was detected by XRPD

Chemical Stability Studies

Chemical stability studies for certain various solid forms of the compound of Formula I described herein were examined under open container and packaging configuration conditions.

For the open container stability studies, a sample of a solid form of the compound of Formula Ia, Formula I Vanillate Form II, Formula I Form I, and Formula I Form II was placed in an open container in a stability chamber at: (i) 40° C. and 75% relative humidity (RH); or (ii) 60° C. (see Table 3). Depending on the sample, the total impurity of the sample was measured at time=4 weeks and 8 weeks, at time=2 weeks and 4 weeks, or at time=15 weeks using liquid chromatography (LC). The general LC conditions were as follows.

Mobile Phases
 Mobile phase A: 0.2% trifluoroacetic acid ("TFA") in water
 Mobile phase B: 0.2% trifluoroacetic acid in acetonitrile
  Operating parameters

| Sample | Mobile phase A (%) | Mobile phase B (%) |
| --- | --- | --- |
| The compound of Formula (Ia) | 0.2% TFA in water | 0.2% TFA in acetonitrile |
| Formula I Vanillate Form II | 0.2% TFA in water | 0.2% TFA in acetonitrile |
| Formula I Form I | 0.2% TFA in water | 0.2% TFA in acetonitrile |
| Formula I Form II | 0.2% TFA in water | 0.2% TFA in acetonitrile |

Column: ACQUITY UPLC® CSH C18 130 Å, 1.7 μm, 2.1 mm×150 mm
Flow rate: 0.5 mL/min
Detection: 260 nm
Column temperature: 50° C.

| Gradient Table | | |
| --- | --- | --- |
| Time (min) | Mobile phase A | Mobile phase B |
| 0.0 | 100 | 0 |
| 0.6 | 100 | 0 |
| 10.6 | 84 | 16 |
| 12.4 | 84 | 16 |
| 25.0 | 71 | 29 |
| 26.0 | 5 | 95 |
| 27.0 | 100 | 0 |
| 30.0 | 100 | 0 |

The results in Table 3 show the percentage degradation of the compound of Formula Ia, Formula I Vanillate Form II, Formula I Form I, and Formula I Form II. As can be seen, Formula I Vanillate Form II, Formula I Form I, and Formula I Form II are more chemically stable than the compound of Formula (Ia). For example, the compound of Formula (Ia) exhibited a total degradation of about 8% after 8 weeks of being subjected to open container conditions at 40° C./75% RH relative to the initial % AN value. On the other hand, a lower total degradation was observed for both Formula I Vanillate Form II and Formula I Form I under the same conditions and duration. Formula I Form II exhibited a total degradation of about 2% at the same stress conditions, but after about twice the exposure duration (i.e., 15 weeks). These results indicate that Formula I Vanillate Form II, Formula I Form I, and Formula I Form II have superior chemical stability over the compound of Formula (Ia).

TABLE 3

Open Container Chemical Stability Data for Solid Forms of the Compound of Formula I

| Sample & Conditions | The compound of Formula (Ia) | | | | | Formula I Vanillate Form II | | | | | Formula I Form I | | | | | Formula I Form II | | |
|---|---|---|---|---|---|---|---|---|---|---|---|---|---|---|---|---|---|---|
| | 40° C./75% RH | | | 60° C. | | 40° C./75% RH | | | 60° C. | | 40° C./75% RH | | | 60° C. | | 40° C./75% RH | | 60° C. |
| | T = 0 | 4 wk | 8 wk | 4 wk | 8 wk | T = 0 | 4 wk | 8 wk | 2 wk | 4 wk | T = 0 | 4 wk | 8 wk | 4 wk | 8 wk | T = 0 | 15 wk | 15 wk |
| Purity of Compound of Formula I (% AN) | | | | | | | | | | | | | | | | | | |
| | 98.0 | 94.8 | 89.9 | 96.6 | 95.7 | 98.3 | 98.1 | 97.9 | 98.2 | 98.2 | 99.1 | 98.8 | 98.2 | 98.9 | 98.9 | 98.7 | 96.6 | 98.7 |
| Degradation products (% AN) | | | | | | | | | | | | | | | | | | |
| | 0.75 | 0.45 | 1.15 | 0.35 | 0.66 | 0.07 | 0.20 | 0.26 | tr | tr | 0.06 | 0.12 | 0.52 | 0.05 | 0.13 | 0.08 | 2.23 | 0.16 |
| | 0.48 | 2.15 | 6.54 | 1.09 | 1.97 | 0.10 | 0.22 | 0.30 | 0.27 | 0.10 | — | 0.26 | 0.41 | 0.26 | 0.33 | — | — | — |

(I)

(V)

(VI)

TABLE 3-continued

Open Container Chemical Stability Data for Solid Forms of the Compound of Formula I

| Sample & Conditions | The compound of Formula (Ia) | | | | | Formula I Vanillate Form II | | | | | Formula I Form I | | | | | Formula I Form II | | |
|---|---|---|---|---|---|---|---|---|---|---|---|---|---|---|---|---|---|---|
| | 40°C/75% RH | | | 60°C | | 40°C/75% RH | | | 60°C | | 40°C/75% RH | | | 60°C | | 40°C/75% RH | | 60°C |
| | T=0 | 4 wk | 8 wk | 4 wk | 8 wk | T=0 | 4 wk | 8 wk | 2 wk | 4 wk | T=0 | 4 wk | 8 wk | 4 wk | 8 wk | T=0 | 15 wk | 15 wk |
| RRT 0.10 | 0.14 | 0.12 | 0.11 | 0.13 | 0.14 | tr | 0.05 | 0.05 | tr | 0.05 | | | | | | 0.06 | tr | 0.06 |
| RRT 0.20 | | 1.23 | 1.03 | 0.90 | 0.5 | | | | | | | | | | | | | |
| RRT 0.21 | | | 0.63 | | 0.33 | | | | | | | | | | | | | |
| RRT 0.25 | | | 0.09 | | | | | | | | | | | | | | | |
| RRT 0.32 | tr | | | | | | | | | | | | | | | | | |
| RRT 0.34 | 0.06 | | | | | | 0.07 | | | | | | | | | | | |
| RRT 0.36 | | | | | 0.06 | | | 0.05 | | | 0.15 | 0.15 | 0.12 | | | | | |
| RRT 0.43 | | 0.66 | | 0.29 | | | | 0.05 | | | | | 0.15 | | | | | |
| RRT 0.46 | | | | | | | | | | | | | | | | | | 0.67 |
| RRT 0.49 | | | tr | | 0.1 | | | | | | | | | | | | | |
| RRT 0.50 | | | | | | | | | tr | | | | | | | | 0.07 | |
| RRT 0.55 | | | | | | | | | | | | | | | | | tr | |
| RRT 0.61 | | | | | | | | | | | | | | | | | | tr |
| RRT 0.62 | | | | | | | | | | | | | | | | | tr | |
| RRT 0.68 | | | | | | | | | | tr | | | | | | 0.11 | 0.05 | 0.05 |
| RRT 0.75 | | | | | | | | | tr | | | | | | | | 0.2 | |
| RRT 0.86 | 0.14 | 0.13 | 0.11 | 0.14 | 0.12 | 0.13 | 0.15 | 0.13 | 0.13 | 0.13 | 0.05 | tr | tr | 0.06 | 0.05 | 0.18 | 0.18 | 0.18 |
| RRT 1.16 | 0.45 | 0.42 | 0.39 | 0.43 | 0.44 | 1.38 | 1.35 | 1.35 | 1.35 | 1.35 | 0.61 | 0.57 | 0.63 | 0.61 | tr | 0.05 | tr | 0.05 |
| RRT 1.19 | tr | 0.09 | 0.07 | 0.08 | 0.07 | | | | | | 0.66 | | | | | | | |
| RRT 1.22 | | | | | | | | | | | 0.87 | 1.19 | 1.77 | 1.06 | 1.12 | | | tr |
| RRT 1.27 | | | | | | 1.67 | 1.91 | 2.09 | 1.83 | 1.81 | | | | | | 0.10 | 0.05 | 0.09 |
| RRT 1.33 | | | | | | | | | | | | | | | | | | |
| Total impurity/degradation product | 2.02 | 5.25 | 10.12 | 3.41 | 4.33 | | | | | | | | | | | 1.32 | 3.45 | 1.26 |

*Structure of the degradation product or impurity has not been proposed or confirmed by further characterization
RRT = Relative retention time of the individual impurity to the compound of Formula I in the chromatogram
% AN = Area percentage of the individual peak in the chromatogram relative to the total amount of chromatographic peaks in the chromatogram Additionally, packaging configuration stability studies of Formula I Form II (Tables 4 and 5) and the compound of Formula (Ia) (Table 6) were conducted.

As summarized in Tables 4 and 5, a sample of Formula I Form II was placed in a double polyethylene bag that was sealed in a foil pouch and placed in a high density polyethylene plastic bottle under controlled storage environments at: (i) 30° C. and 75% relative humidity (RH) (see Table 4) and (ii) 40° C. and 75% RH (see Table 5). The total impurity of the sample was measured at time=0, 3, 6, 9 and 12 months for condition (i), and time=0, 1, and 3 months for condition (ii) using liquid chromatography (LC). The LC conditions were as follows:

Mobile Phases
  Mobile phase A: 0.1% trifluoroacetic acid in water with 35 mM ammonium chloride
  Mobile phase B: 0.1% trifluoroacetic acid in acetonitrile Operating Parameters

| Sample | Mobile phase A (%) | Mobile phase B (%) |
|---|---|---|
| Form II | 0.1% TFA in water with 35 mM ammonium chloride | 0.1% TFA in acetonitrile |

Column: ACQUITY UPLC CSH Phenyl Hexyl, 1.7 rpm, 3.0 mm×150 mm

Flow rate: 0.85 mL/min

Detection: 260 nm

Column temperature: 30

| Gradient Table | | |
|---|---|---|
| Time (min) | Mobile phase A | Mobile phase B |
| 0.0 | 99 | 1 |
| 12.4 | 84 | 16 |
| 25.0 | 71 | 29 |
| 30.0 | 50 | 50 |
| 35.0 | 5 | 95 |
| 36.0 | 99 | 1 |

TABLE 4

Packaging Configuration Chemical Stability Data at 30° C./75% RH for Formula I Form II

| Sample & Conditions | 30° C./75% RH | | | | |
|---|---|---|---|---|---|
| | T = 0 | 3 Mo | 6 Mo | 9 Mo | 12 Mo |
| Purity of Compound of Formula I Form II (% weight/weight) | 99.7 | 99.2 | 98.9 | 98.6 | 98.8 |
| Degradation products (% weight/weight) | | 0.20 | 0.39 | 0.63 | 0.83 |

TABLE 4-continued

Packaging Configuration Chemical Stability Data at 30° C./75% RH for Formula I Form II

| Sample & Conditions | 30° C./75% RH | | | | |
|---|---|---|---|---|---|
| | T = 0 | 3 Mo | 6 Mo | 9 Mo | 12 Mo |

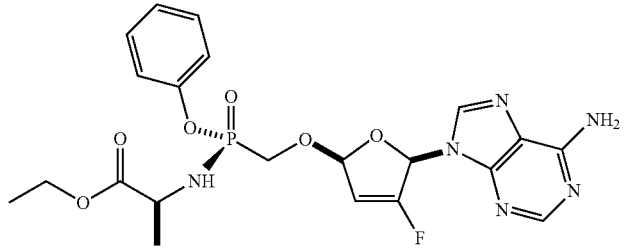

(VII)

| | | | | | |
|---|---|---|---|---|---|
| Phenol | 0.06 | | | | 0.05 |
| RRT 0.34 | | 0.06 | 0.07 | 0.07 | 0.06 |
| Total Impurity/degradation product | 0.1 | 0.3 | 0.5 | 0.7 | 1.0 |

TABLE 5

Packaging Configuration Chemical Stability Data at 40° C./75% RH for Formula Form II

| Sample & Conditions | 40° C./75% RH | | |
|---|---|---|---|
| | T = 0 | 1 Mo | 3 Mo |

Purity of Compound of Formula I Form II (% weight/weight)

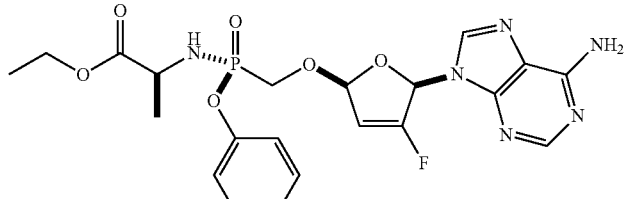

(I)

99.7  100.2  97.6

Degradation products (% weight/weight)

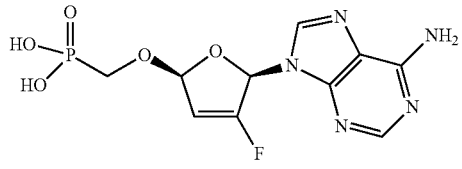

(V)

0.20  1.20

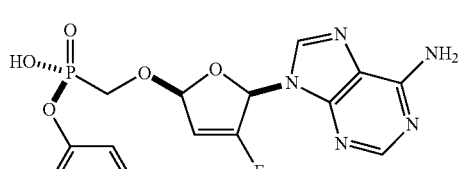

(VI)

TABLE 5-continued

Packaging Configuration Chemical Stability Data at 40° C./75% RH for Formula Form II

| Sample & Conditions | 40° C./75% RH | | |
|---|---|---|---|
| | T = 0 | 1 Mo | 3 Mo |

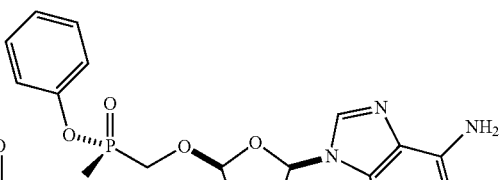

(VII)

| | | | |
|---|---|---|---|
| Phenol | 0.06 | 0.06 | 0.08 |
| RRT 0.28 | | | |
| RRT 0.34 | | | 0.07 |
| RRT 0.45 | | | |
| Total Impurity/degradation product | 0.1 | 0.3 | 1.4 |

Table 4 shows the percentage degradation of Formula I Form II at 30° C. and 75% relative humidity (RH). The total degradation observed after 12 months storage is 1.0 (see Table 4). Table 5 shows the percentage degradation of Formula I Form II under the accelerated stress condition of 40° C./75% RH. As can been seen in Table 5, Formula I Form II exhibits a chemical degradation of 1.4% after 3 months.

TABLE 6

Packaging Configuration Chemical Stability for the Compound of Formula (Ia) at 25° C./60% RH and 40° C./75% RH

| Sample & Conditions | 25° C./60% RH | | | | 40° C./75% RH | | |
|---|---|---|---|---|---|---|---|
| | T = 0 | 1 Mo | 3 Mo | 6 Mo | T = 0 | 4 days | 2 week |

Purity of Compound of Formula Ia (% weight/weight)

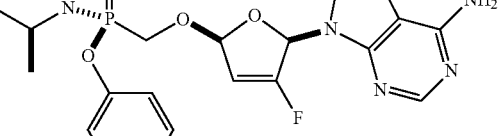

(Ia)

| | | | | | | | |
|---|---|---|---|---|---|---|---|
| | 97.8 | 97.7 | 98.0 | 97.1 | 97.8 | 97.5 | 97.0 |

Degradation products (% weight/weight)

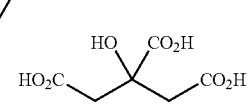

(V)

| | | | | | | | |
|---|---|---|---|---|---|---|---|
| | 0.09 | 0.31 | 0.59 | 0.89 | 0.09 | 0.42 | 0.71 |

TABLE 6-continued

Packaging Configuration Chemical Stability for the Compound of Formula (Ia) at 25° C./60% RH and 40° C./75% RH

| Sample & Conditions | 25° C./60% RH | | | | 40° C./75% RH | | |
|---|---|---|---|---|---|---|---|
| | T = 0 | 1 Mo | 3 Mo | 6 Mo | T = 0 | 4 days | 2 week |
| 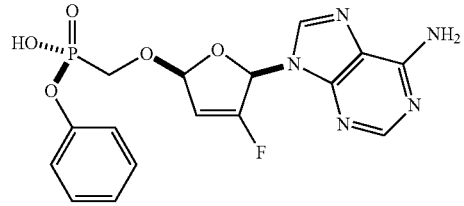 (VI) | 0.09 | 0.21 | 0.44 | 0.75 | 0.09 | 0.15 | 0.31 |
| 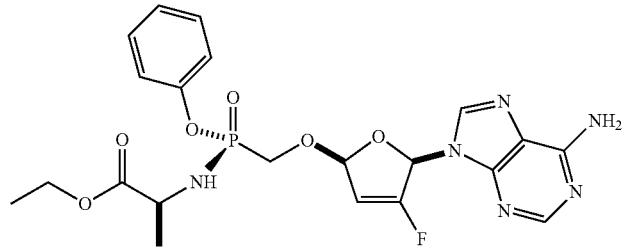 (VII) | | | | | | | |
| RRT 0.14 | | | | 0.05 | | | |
| RRT 0.38 | 0.14 | 0.16 | 0.16 | 0.15 | 0.14 | 0.15 | 0.15 |
| RRT 0.42 | | | 0.06 | 0.06 | | | |
| RRT 0.61 | 0.08 | 0.07 | 0.07 | 0.06 | 0.08 | 0.08 | 0.07 |
| RRT 0.82 | | 0.05 | 0.08 | | | | |
| RRT 1.51 | | | | 0.05 | | | |
| Total Impurity/degradation product | 0.4 | 0.8 | 1.4 | 2.0 | 0.4 | 0.8 | 1.2 |

For the packaging configuration stability studies of the compound of Formula (Ia), a sample of the compound was placed in a double polyethylene bag and placed in a high density polyethylene plastic bottle under controlled conditions at either (i) 25° C. and 60% relative humidity (RH), or (ii) 40° C. and 75% RH. The total impurity of the sample was measured at (i) time=0, 1, 3 and 6 months, or (ii) time=0, 4 days and 2 weeks for the conditions at 25° C./60% RH and 40° C./75% RH, respectively. The LC conditions were as follows:

Mobile Phases

Mobile phase A: 0.1% trifluoroacetic acid in water

Mobile phase B: 0.1% trifluoroacetic acid in acetonitrile

Operating Parameters

| Sample | Mobile phase A (%) | Mobile phase B (%) |
|---|---|---|
| The compound of Formula (Ia) | 0.1% TFA in water | 0.1% TFA in acetonitrile |

Column: ACQUITY UPLCR CSH C18 130 Å, 1.7 μm, 2.1 mm×150 mm

Flow rate: 0.5 mL/min

Detection: 260 nm

Column temperature: 50° C.

| Gradient Table | | |
|---|---|---|
| Time (min) | Mobile phase A | Mobile phase B |
| 0.0 | 99 | 1 |
| 0.6 | 99 | 1 |
| 10.6 | 84 | 16 |
| 12.4 | 84 | 16 |
| 25.0 | 71 | 29 |
| 26.0 | 5 | 95 |
| 27.0 | 99 | 1 |

As shown in Table 6, the total degradation products observed for the Compound of Formula (Ia) under the 25° C. at 60% RH condition is 2.0% after 6 months. Similarly, the total degradation products observed for Compound of Formula (Ia) under the 40° C. at 75% RH condition is 1.2% after 2 weeks.

Additional packaging configuration stability studies of Formula I Form II (Table 7) and the compound of Formula (Ia) (Table 8) were conducted.

As summarized in Table 7, a sample of Formula I Form II was placed in an amber glass jar or in a double polyethylene bag in a high density polyethylene plastic bottle (HDPE bottle) under controlled storage environments at: (i) −20° C.; (ii) 25° C. and 60% relative humidity (RH); or (iii) 40° C. and 75% relative humidity (RH). The total impurity of the sample was measured at time=0, 4, or 9 weeks using liquid chromatography (LC). The LC conditions were as follows.

Mobile Phases
Mobile phase A: 0.2% trifluoroacetic acid in water
Mobile phase B: 0.2% trifluoroacetic acid in acetonitrile
Operating Parameters

| Sample | Mobile phase A (%) | Mobile phase B (%) |
|---|---|---|
| Formula I Form II | 0.2% TFA in water | 0.2% TFA in acetonitrile |

Column: ACQUITY UPLC® CSH C18 130 Å, 1.7 μm, 2.1 mm×150 mm
Flow rate: 0.5 mL/min
Detection: 260 nm
Column temperature: 50° C.

| Gradient Table | | |
|---|---|---|
| Time (min) | Mobile phase A | Mobile phase B |
| 0.0 | 100 | 0 |
| 0.6 | 100 | 0 |
| 10.6 | 84 | 16 |
| 12.4 | 84 | 16 |
| 25.0 | 71 | 29 |
| 26.0 | 5 | 95 |
| 27.0 | 100 | 0 |
| 30.0 | 100 | 0 |

TABLE 7

Packaging Configuration Chemical Stability Data for Formula I Form II

| Time (wks) | Stability Condition | Storage Configuration | Formula I Form II (Purity by % AN) | Total Impurities/ Degradation products (% AN) | The compound of Formula (VI) (%) | Unspecified impurities (% AN) RRT 0.34 (%) | RRT 0.61 (%) | RRT 0.82 (%) | XRPD | Water Content | Appearance |
|---|---|---|---|---|---|---|---|---|---|---|---|
| 0 | −20° C. | Bulk in Amber Glass Jar | 99.6 | 0.4 | 0.29 | 0.15 | | tr | Crystalline | 0.04 | Off-white solid |
| 4 | −20° C. | Double PE in HDPE Bottle | 99.6 | 0.4 | 0.27 | 0.15 | | tr | Crystalline | 0.04 | Off-white solid |
| 9 | 25° C./ 60% RH | Double PE in HDPE Bottle | 99.6 | 0.4 | 0.21 | 0.15 | tr | tr | Crystalline | 0.08 | Off-white solid |
| 9 | 40° C./ 75% RH | Double PE in HDPE Bottle | 99.6 | 0.4 | 0.21 | 0.14 | tr | tr | Crystalline | 0.06 | Off-white solid | tr = trace amount (0.03-0.05%);
Double PE = a double polyethylene bag;
HDPE Bottle = high density polyethylene plastic bottle
% AN = Area percentage of the individual peak in the chromatogram relative to the total amount of chromatographic peaks in the chromatogram Table 7 depicts the percentage degradation of Formula I Form II. As can be seen, Formula I Form II does not experience significant chemical degradation under the packaging conditions examined in Table 7 (i.e., up to 9 weeks).

For the packaging configuration stability studies of the compound of Formula (Ia), a sample of the compound was placed in a double polyethylene bag in a high density polyethylene plastic bottle under controlled conditions at either (i) −20° C.; (ii) 5° C.; or (iii) 25° C. and 60% relative humidity (RH). As shown in Table 8 the total impurity of the sample was measured at time=0, 1 month, and 3 months using liquid chromatography (LC). The LC conditions were as follows.

Mobile Phases
Mobile phase A: 0.1% trifluoroacetic acid in water
Mobile phase B: 0.1% trifluoroacetic acid in acetonitrile
Operating parameters

| Sample | Mobile phase A (%) | Mobile phase B (%) |
|---|---|---|
| The compound of Formula (Ia) | 0.1% TFA in water | 0.1% TFA in acetonitrile |

Column: ACQUITY UPLC® CSH C18 130 Å, 1.7 µm, 2.1 mm×150 mm
Flow rate: 0.5 mL/min
Detection: 260 nm
Column temperature: 50° C.

TABLE 8

Packaging Configuration Chemical Stability Data for the Compound of Formula (Ia)

| Sample & Conditions* | | −20° C. | | | 5° C. | | | 25° C./60% RH | | |
|---|---|---|---|---|---|---|---|---|---|---|
| | | T = 0 | 1 Mo | 3 Mo | T = 0 | 1 Mo | 3 Mo | T = 0 | 1 Mo | 3 Mo |
| Purity of Compound of Formula Ia (% AN) | | | | | | | | | | |
| 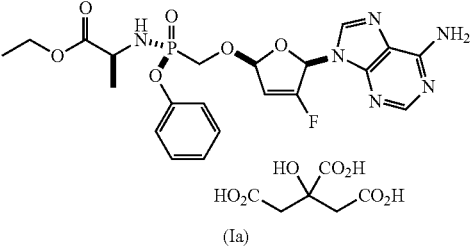 (Ia) | | 99.6 | 99.5 | 99.5 | 99.6 | 99.5 | 99.4 | 99.6 | 99.2 | 98.6 |
| Degradation products (% AN) | | | | | | | | | | |
| 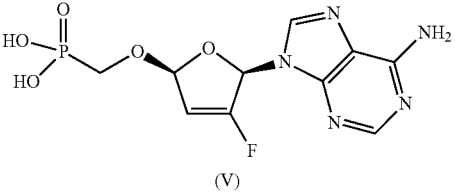 (V) | | 0.09 | 0.08 | 0.07 | 0.09 | 0.09 | 0.11 | 0.09 | 0.20 | 0.39 |
| 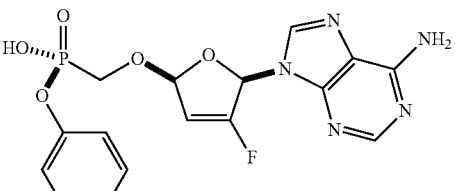 (VI) | | 0.09 | 0.11 | 0.13 | 0.09 | 0.12 | 0.13 | 0.09 | 0.21 | 0.44 |
| 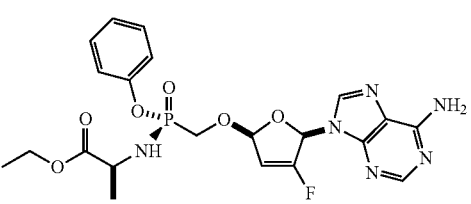 (VII) | | | | | | | | | | |
| Unknown Impurities/Degradation Products** (% AN) | | | | | | | | | | |
| RRT 0.13 | | | | | | 0.08 | | | 0.11 | 0.20 |
| RRT 0.38 | | | 0.14 | 0.16 | 0.17 | 0.14 | 0.16 | 0.16 | 0.14 | 0.16 | 0.16 |

TABLE 8-continued

Packaging Configuration Chemical Stability Data for the Compound of Formula (Ia)

| Sample & Conditions* | −20° C. | | | 5° C. | | | 25° C./60% RH | | |
|---|---|---|---|---|---|---|---|---|---|
| | T = 0 | 1 Mo | 3 Mo | T = 0 | 1 Mo | 3 Mo | T = 0 | 1 Mo | 3 Mo |
| RRT 0.42 | | | | | | | | | 0.06 |
| RRT 0.61 | 0.08 | 0.07 | 0.08 | 0.08 | 0.08 | 0.07 | 0.08 | 0.07 | 0.07 |
| RRT 0.82 | | 0.05 | 0.06 | | 0.05 | | | 0.05 | 0.08 |
| RRT 1.51 | | | | | 0.05 | | | | 0.05 |
| Total Impurity/degradation product | 0.4 | 0.5 | 0.5 | 0.4 | 0.5 | 0.6 | 0.4 | 0.8 | 1.4 |
| Water Content (%) | | | | | | | | | |
| | 0.16 | 0.18 | 0.13 | 0.16 | 0.17 | 0.14 | 0.16 | 0.18 | 0.17 |
| Appearance | | | | | | | | | |
| | Conf | Conf | Conf | Conf | Conf | Conf | Conf | Conf | Conf |
| XRPD | | | | | | | | | |
| | Crys | Crys | Crys | Crys | Crys | Crys | Crys | Crys | Crys |

\* = Samples were placed in a double polyethylene bag in a high density polyethylene plastic bottle
\*\* = Structure of the degradation product or impurity has not been proposed or confirmed by further characterization
RRT = Relative retention time of the individual impurity to the compound of Formula I in the chromatogram
% AN = area percentage of chromatographic peak relative to the compound of Formula I in the chromatogram
Conf = white to off-white to light brown solid
Crys = Crystalline As shown in Tables 7 and 8, the Compound of Formula (Ia) experiences chemical degradation under the packaging conditions examined while Formula I Form II does not. For example, both the compound of Formula (Ia) and Formula I Form II were placed in a double polyethylene bag in a high density polyethylene plastic bottle and subjected to 25° C. at 60% RH. After 9 weeks, Formula I Form II exhibited a 99.6 purity by % AN. As for the compound of Formula (Ia), it exhibited a 99.2 purity by % AN after 1 month and a 98.6 purity by % AN after 3 months.

Solubility Studies

A. Sample Preparation

1N Hydrochloric acid and 1N sodium hydroxide were added to filtered water to generate aqueous solutions with pH values ranging between 3 and 7. The aqueous solutions were then transferred to centrifuge tubes and an excess amount of either Formula I Form I or Formula I Form II was added. The mixture was briefly sonicated for about 10 seconds and then transferred to a shaker. The samples were shaken for about 35 h at room temperature at 1,400 rpm.

B. Sample Analysis

The samples were centrifuged for about 10 minutes and the pH of the supernatant was measured. The samples were diluted 200× using a 1:1 mixture of water and acetonitrile. The samples were analyzed using Ultra Performance Liquid Chromatography (UPLC) to determine concentration. Residual solids were analyzed by powder X-Ray diffraction and it was confirmed that there was no form change during the course of the experiment.

C. Results

As shown in Table 6 and FIG. 24, Formula I Form I and Formula I Form II exhibit a similar pH solubility profile. This data indicates that Formula I Form II should have comparable pharmacokinetics (PK) as Formula I Form I.

TABLE 6

Intrinsic Solubility of Formula I Form I and Formula I Form II
Intrinsic Solubility

| Formula I Form I | Formula I Form II |
|---|---|
| 6.0 mg/mL (pH 6.1) | 4.4 mg/mL (pH 5.9) |

Competitive Slurry Studies

Formula I Form I (about 5.2 g) in isopropyl acetate (about 26 mL) was stirred with about 20 mg of Formula I Form II at 20° C. for 24 hours. The slurry was then heated to 50° C. for 4 h, when wetcake analysis showed complete conversion of the slurry to Formula I Form II. The slurry was cooled to room temperature, stirred for 2 h, and filtered to give about 4.2 g Formula I Form II. This study demonstrates that Formula I Form II is thermodynamically more stable than Formula I Form I.

Exposure Studies

Figure 25B:
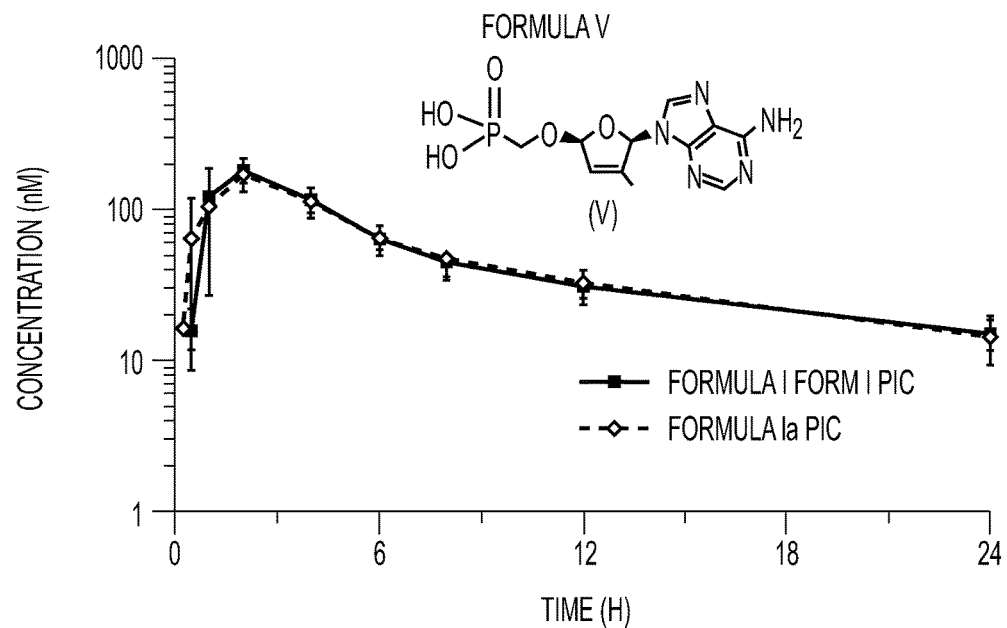

Exposure studies were conducted in fasted dogs (n=4) that were pre-treated with pentagastrin. As shown in FIG. 25 and Table 7, comparable exposure was achieved for Formula I Form I and the compound of Formula (Ia).

TABLE 7

Exposure of Formula I Form I and the Compound of Formula (Ia) in Pentagastrin Pre-treated, Fasted Dogs

| Dose | Analyte | PK Parameter | The Compound of Formula (Ia) | Formula I Form I |
|---|---|---|---|---|
| 10 mg | Formula I | Mean $AUC_{last}$ (nM*hr) (SD) | 49.0 (12.7) | 44.3 (23.8) |
| | | Mean $C_{max}$ (nM) (SD) | 87.2 (38.3) | 83.2 (46.2) |

TABLE 7-continued

Exposure of Formula I Form I and the Compound of Formula (Ia) in Pentagastrin Pre-treated, Fasted Dogs

| Dose | Analyte | PK Parameter | The Compound of Formula (Ia) | Formula I Form I |
|---|---|---|---|---|
| | 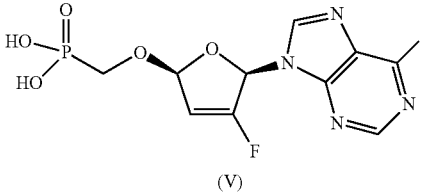 (V) | Mean $AUC_{last}$ (nM*hr) (SD) | 1200 (254) | 1190 (223) |
| | | Mean $AUC_{inf}$ (nM*hr) (SD) | 1400 (349) | 1420 (256) |
| | | Mean $C_{max}$ (nM) (SD) | 172 (44.7) | 183 (31.1) |

*Dosed as 1:1 API: pregelatinized starch ("PGS") Powder in Capsule (PIC) to N = 4 dogs (fasted, pentagastrin pre-treated)

Each of the references including all patents, patent applications and publications cited in the present application is incorporated herein by reference in its entirety, as if each of them is individually incorporated. Further, it would be appreciated that, in the above teaching of invention, the skilled in the art could make certain changes or modifications to the invention, and these equivalents would still be within the scope of the invention defined by the appended claims of the application. Each of the references including all patents, patent applications and publications cited in the present application is incorporated herein by reference in its entirety, as if each of them is individually incorporated. Further, it would be appreciated that, in the above teaching of invention, the skilled in the art could make certain changes or modifications to the invention, and these equivalents would still be within the scope of the invention defined by the appended claims of the application.

What is claimed:

1. A crystalline form of ethyl ((S)-((((2R,5R)-5-(6-amino-9H-purin-9-yl)-4-fluoro-2,5-dihydrofuran-2-yl)oxy)methyl)(phenoxy)phosphoryl)-L-alaninate, wherein the crystalline form is Formula I Form I.

2. The crystalline form of claim 1, characterized by an X-ray powder diffraction pattern having peaks at 7.7°, 11.2°, and 15.2° 2θ±0.2° 2θ.

3. The crystalline form of claim 2, wherein the X-ray powder diffraction pattern has further peaks at 18.5°, 20.3°, and 21.4° 2θ±0.2° 2θ.

4. The crystalline form of claim 3, wherein the X-ray powder diffraction pattern has a further peak at 24.6° 2θ±0.2° 2θ.

5. The crystalline form of claim 1, characterized by an X-ray powder diffraction pattern substantially as shown in FIG. 1.

6. The crystalline form of claim 1, characterized by differential scanning calorimetry thermogram substantially as shown in FIG. 2.

7. The crystalline form of claim 1, characterized by thermogravimetric analysis thermogram substantially as shown in FIG. 3.

8. The crystalline form of claim 1, characterized by a dynamic vapor sorption isotherm substantially as shown in FIG. 4.

9. A pharmaceutical composition comprising a therapeutically effective amount of a form of claim 1 and a pharmaceutically acceptable excipient.

10. The pharmaceutical composition of claim 9, further comprising one to three additional therapeutic agents.

11. The pharmaceutical composition of claim 10, wherein at least one of the additional therapeutic agents is active against HIV.

12. The pharmaceutical composition of claim 11, wherein the pharmaceutical composition is in a unit dosage form.

13. The pharmaceutical composition of claim 12, wherein the unit dosage form is a tablet.

14. A method of inhibiting or relieving a virus infection in a human, the method comprising administering to the human in need thereof a therapeutically effective amount of the crystalline form of claim 1, wherein the virus infection is caused by HIV.

* * * * *

UNITED STATES PATENT AND TRADEMARK OFFICE
CERTIFICATE OF CORRECTION

PATENT NO. : 10,851,125 B2
APPLICATION NO. : 16/049441
DATED : December 1, 2020
INVENTOR(S) : Olga Viktorovna Lapina, Bing Shi and Silas Wang Page 1 of 1

It is certified that error appears in the above-identified patent and that said Letters Patent is hereby corrected as shown below:

On the Title Page

Column 1, (Title (54)) Line 5, delete "PHOSPHORYL(-L-" and insert -- PHOSPHORYL)-L- --, Column 2, (Other Publications) Lines 1-2, delete "www.healthline.corn/" and insert -- www.healthline.com/ --, In the Specification Column 1, Line 4, delete "PHOSPHORYL(-L-" and insert -- PHOSPHORYL)-L- --.

Signed and Sealed this
Seventeenth Day of August, 2021

Drew Hirshfeld
*Performing the Functions and Duties of the
Under Secretary of Commerce for Intellectual Property and
Director of the United States Patent and Trademark Office*